US012191034B2

(12) United States Patent
Wahezi

(10) Patent No.: US 12,191,034 B2
(45) Date of Patent: Jan. 7, 2025

(54) NEUROMODULATION WAVEFORM WATERMARKING AND PRESCRIBING

(71) Applicant: Sayed Emal Wahezi, New Rochelle, NY (US)

(72) Inventor: Sayed Emal Wahezi, New Rochelle, NY (US)

( * ) Notice: Subject to any disclaimer, the term of this patent is extended or adjusted under 35 U.S.C. 154(b) by 0 days.

(21) Appl. No.: 18/605,638

(22) Filed: Mar. 14, 2024

(65) Prior Publication Data

US 2024/0331858 A1 Oct. 3, 2024

Related U.S. Application Data

(63) Continuation-in-part of application No. 18/229,743, filed on Aug. 3, 2023, now Pat. No. 11,964,153.
(Continued)

(51) Int. Cl.
*G16H 40/67* (2018.01)
*A61N 1/36* (2006.01)
(Continued)

(52) U.S. Cl.
CPC ......... *G16H 40/67* (2018.01); *A61N 1/36021* (2013.01); *A61N 1/3603* (2017.08);
(Continued)

(58) Field of Classification Search
CPC ........ G16H 40/67; G16H 10/60; G16H 20/40; A61N 1/36021; A61N 1/3603; A61N 1/36062; A61N 1/36071; A61N 1/36139
See application file for complete search history.

(56) References Cited

U.S. PATENT DOCUMENTS

| 5,961,467 A | 10/1999 | Shimazu et al. |
| 6,923,770 B2 | 8/2005 | Narimatsu |

(Continued)

FOREIGN PATENT DOCUMENTS

| AU | 2013306411 B2 * | 6/2016 | ........... A61B 5/0036 |
| CN | 106512208 A | 3/2017 | |

(Continued)

OTHER PUBLICATIONS

Peng et al., "Mechanisms and Applications of Neuromodulation Using Surface Acoustic Waves—A Mini-Review", Frontiers in Neuroscience, vol. 15, Article 629056, Jan. 2021, 10 pages.
(Continued)

*Primary Examiner* — Sheetal R Paulson
(74) *Attorney, Agent, or Firm* — HOLLOWELL PATENT GROUP; Kelly J. Hollwell

(57) ABSTRACT

Disclosed apparatus and associated methods relate to collecting signal data sampled using an input electrode contacting a patient while a neuromodulation device (NMD) applies a neuromodulation waveform using an output electrode contacting the patient, identifying characteristics of the applied neuromodulation waveform determined as a function of the collected signal data, and generating a notification if the applied neuromodulation waveform matches any known predetermined neuromodulation waveform, based on the identified characteristics. The applied neuromodulation waveform may include waveform identification data. The waveform identification data may be a watermark added by the NMD. Identification data may be encoded by varying amplitude or timing of the applied neuromodulation waveform or by modulating a carrier wave added to the applied neuromodulation waveform. An implementation may advantageously detect use of proprietary neuromodulation waveforms in real time, permitting automatic invoicing and
(Continued)

treatment protocol conformance verification triggered by usage detection and increasing access to effective neuromodulation waveforms.

28 Claims, 24 Drawing Sheets

Related U.S. Application Data

(60) Provisional application No. 63/456,806, filed on Apr. 3, 2023.

(51) Int. Cl.
*G16H 10/60* (2018.01)
*G16H 20/40* (2018.01)

(52) U.S. Cl.
CPC ..... *A61N 1/36062* (2017.08); *A61N 1/36071* (2013.01); *A61N 1/36139* (2013.01); *G16H 10/60* (2018.01); *G16H 20/40* (2018.01)

(56) References Cited

U.S. PATENT DOCUMENTS

| | | | |
|---|---|---|---|
| 7,192,402 | B2 | 3/2007 | Amano et al. |
| 7,483,747 | B2 | 1/2009 | Gliner et al. |
| 7,489,966 | B2 | 2/2009 | Leinders et al. |
| 8,099,164 | B2 | 1/2012 | Gillberg et al. |
| 8,244,360 | B2 | 8/2012 | Heruth et al. |
| 8,380,318 | B2 | 2/2013 | Kishawi et al. |
| 8,473,063 | B2 | 6/2013 | Gupta et al. |
| 8,612,018 | B2 | 12/2013 | Gillbe |
| 8,773,239 | B2 | 7/2014 | Phillips et al. |
| 8,862,214 | B2 | 10/2014 | Ghodrati |
| 9,199,089 | B2 | 12/2015 | Perryman et al. |
| 9,492,667 | B1 | 11/2016 | Kent et al. |
| 9,504,832 | B2 | 11/2016 | Lubbus et al. |
| 9,737,717 | B2 | 8/2017 | Moffitt et al. |
| 10,667,747 | B2 | 6/2020 | Annoni et al. |
| 10,758,732 | B1 * | 9/2020 | Heldman ........... A61N 1/37235 |
| 10,905,894 | B2 | 2/2021 | Karpf |
| 10,940,311 | B2 * | 3/2021 | Gozani .............. A61N 1/36021 |
| 11,154,710 | B2 | 10/2021 | Belson et al. |
| 11,170,793 | B2 | 11/2021 | Jin et al. |
| 11,623,092 | B2 | 4/2023 | Peyman et al. |
| 11,854,682 | B2 | 12/2023 | Lin et al. |
| 2004/0186386 | A1 | 9/2004 | Kolluri et al. |
| 2016/0038048 | A1 | 2/2016 | Ting et al. |
| 2016/0287110 | A1 | 10/2016 | Morris et al. |
| 2017/0003046 | A1 | 1/2017 | Gould |
| 2017/0095670 | A1 * | 4/2017 | Ghaffari ................ A61M 21/02 |
| 2017/0157410 | A1 * | 6/2017 | Moffitt ................... G16H 70/20 |
| 2017/0304636 | A1 | 10/2017 | Steinke et al. |
| 2017/0359339 | A1 * | 12/2017 | Hevizi .............. H04M 1/72406 |
| 2019/0065731 | A1 * | 2/2019 | Brocious ............. H04L 63/0838 |
| 2019/0111255 | A1 * | 4/2019 | Errico ....................... A61N 2/02 |
| 2020/0384270 | A1 * | 12/2020 | Doan ................. A61N 1/37247 |
| 2021/0299446 | A1 | 9/2021 | Errico et al. |
| 2022/0096822 | A1 | 3/2022 | Schepis et al. |
| 2022/0203107 | A1 | 6/2022 | Nobles et al. |
| 2023/0060761 | A1 | 3/2023 | Doan |
| 2023/0121038 | A1 | 4/2023 | John et al. |

FOREIGN PATENT DOCUMENTS

| | | | |
|---|---|---|---|
| EP | 3747507 | B1 | 11/2023 |
| WO | 8707511 | A2 | 12/1987 |

OTHER PUBLICATIONS

Ploner et al., "Brain Rhythms of Pain", Trends in Cognitive Sciences, Feb. 2017, vol. 21, No. 2 http://dx.doi.org/10.1016/j.tics.2016.12.001.

Potas et al., "Waveform Similarity Analysis: A Simple Template Comparing Approach for Detecting and Quantifying Noisy Evoked Compound Action Potentials", PLOS One | DOI:10.1371/journal.pone.0136992 Sep. 1, 2015, 18 pages.

Pouromran et al., "Exploration of physiological sensors, features, andmachine learning models for pain intensity estimation", PLOS One | https://doi.org/10.1371/journal.pone.0254108 Jul. 9, 2021, 17 pages.

Quintana et al., "Considerations in the assessment of heart rate variability in biobehavioral research", Frontiers in Neuroscience, vol. 5, Article 805, Jul. 2014, 10 pages.

Rojas et al., "A systematic review of neurophysiological sensing for the assessment of acute pain", Digital Medicine (2023) 6:76 ; https://doi.org/10.1038/s41746-023-00810-1.

Rojas et al., "Multimodal physiological sensing for the assessment of acute pain", Frontiers in Pain Research, Jun. 19, 2023, 11 pages.

Sacco et al., "The Relationship Between Blood Pressure and Pain", The Journal of Clinical Hypertension vol. 15, No. 8, Aug. 2013, pp. 600-605.

Sebastiao et al., "Analysis of Physiological Responses during Pain Induction", Sensors 2022, 22, 9276. https://doi.org/10.3390/s22239276.

Tennant, "Treat the Pain . . . Save a Heart", MedCentral, vol. 10, Issue 8, Feb. 25, 2011. 6 pages.

Tousignant-Laflamme et al., "Establishing a Link Between Heart Rate and Pain in Healthy Subjects: A Gender Effect", The Journal of Pain, vol. 6, No. 6, Jun. 2005: pp. 341-347.

Trautmann et al., "Design, Calibration, and Evaluation of Real-Time Waveform Matching on an FPGA-based Digitizer at 10 GS/s", ACM Transactions on Reconfigurable Technology and Systems vol. 17Issue 2Article No. 24pp. 1-28.

Trautmann et al., "Real-Time Waveform Matching with a Digitizer at 10 GS/s", 2022 32st International Conference on Field-Programmable Logic and Applications, 8 pages.

Verrills et al., "A review of spinal cord stimulation systems for chronic pain", Journal of Pain Research 2016:9 481-492.

Wahezi et al., "Current Waveforms in Spinal Cord Stimulation and Their Impact on the Future of Neuromodulation: A Scoping Review", Neuromodulation: Technology at the Neural Interface vol. 27, Issue 1, Jan. 2024, pp. 47-58.

Wang, "5 Basics of EEG 101: Data Collection, Processing & Analysis", Best Practice, Apr. 20, 2021, 11 pages.

Yang et al., "Continuous Pain Assessment Using Ensemble Feature Selection from Wearable Sensor Data", Proceedings (IEEE Int Conf Bioinformatics Biomed). Nov. 2019 ; 2019: 569-576. doi:10.1109/bibm47256.2019.8983282.

Yao, "A brief tutorial of the Waveform Matched Filter Technique", Georgia Tech, Feb. 21, 2016, 14 pages.

Yoshida et al., "Analgesia nociception index and high frequency variability index: promising indicators of relative parasympathetic tone", Journal of Anesthesia (2023) 37:130-137, https://doi.org/10.1007/s00540-022-03126-8.

Yu et al., "To tailor the conical beam by using planar superstrate", Electronics Letters, vol. 57, No. 1, Jan. 2021, pp. 1-44.

Claron, et al., "The Supplementary Eye Field Tracks Cognitive Efforts," bioRxiv The preprint server for Biology, Cold Spring Harbor Laboratory, Jan. 25, 2021, 22 pages, doi: https://doi.org/10.1101/2021.01.14.426722.

Abbott, "Proclaim™ XR SCS System and Proclaim™ DRG Therapy, Patient Controller App User Guide", 2020, 28 pages.

Abdullayev et al., "Analgesia Nociception Index: assessment of acute postoperative pain", Rev Bras Anestesiol., 2019, 69(4), pp. 396-402.

Baliki et al., "Chronic Pain and the Emotional Brain: Specific Brain Activity Associated with Spontaneous Fluctuations of Intensity of Chronic Back Pain", The Journal of Neuroscience, Nov. 22, 2006 • 26(47):12165-12173.

Boston Scientific, "Vercise Genus Deep Brain Stimulation System", 2023, 4 pages.

Butson, "Computational Models of Neuromodulation", International Review of Neurobiology, vol. 107, 2012 ISSN 0074-7742.

(56) References Cited

OTHER PUBLICATIONS

Chanques et al., "Analgesia nociception index for the assessment of pain in critically ill patients: a diagnostic accuracy study", British Journal of Anaesthesia, 119 (4): 812-20 (2017).
Culaclii et al., "A Biomimetic, SoC-Based Neural Stimulator for Novel Arbitrary-Waveform Stimulation Protocols", Frontiers in Neuroscience, vol. 15, Jul. 2021, pp. 1-17.
Dayoub et al., "Does Pain Lead to Tachycardia? Revisiting the Association Between Self-reported Pain and Heart Rate in a National Sample of Urgent Emergency Department Visits", Mayo Clin Proc. Aug. 2015 ; 90(8): 1165-1166.
Dinsmoor et al., "Using evoked compound action potentials to quantify differential neural activation with burst and conventional, 40 Hz spinal cord stimulation in ovines", Pain Reports, vol. 7, 2022, pp. 1-10.
Erdy et al., "Preliminary Intraoperative Validation of the Nociception Level Index", Anesthesiology, vol. 125, No. 1, Jul. 2016, pp. 193-203.
Ferguson et al., "Wireless communication with implanted medical devices using the conductive properties of the body", Expert Rev Med Devices, vol. 8, No. 4, 2011, pp. 427-433.
Forte et al., "Heart Rate Variability and Pain: A Systematic Review", Brain Sci. vol. 12, 2022, 25 pages.
Heathers, Everything Hertz: methodological issues in short-term frequency-domain HRV:, Frontiers in Physiology, vol. 5, Article 177, May 2014, 15 pages.
Heros et al., "Objective wearable measures and subjective questionnaires for predicting response to neurostimulation in people with chronic pain", Bioelectronic Medicine, vol. 9, No. 13, 2023, 13 pages.
Kardan et al., "Supplementary materials for: Distinguishing cognitive effort and working memory load using scale-invariance and alpha suppression in EEG", vol. 211, May 2020, 116622.
Kim et al., "Pain Assessment Using the Analgesia Nociception Index (ANI) in Patients Undergoing General Anesthesia: A Systematic Review and Meta-Analysis", J. Pers. Med. 2023, 13, 1461.
Kimszal, "Can Pain Cause High Blood Pressure?", Verywell Health, May 7, 2023, 6 pages.
Korving et al., "Physiological Measures of Acute and Chronic Pain within Different Subject Groups: A Systematic Review", Pain Research and Management vol. 2020, Article ID 9249465, 10 pages.
Kriek et al., "Preferred frequencies and waveforms for spinal cord stimulation in patients with complex regional pain syndrome: A multicentre, double-blind, randomized and placebo-controlled crossover trial", Eur J Pain 21 (2017) 507-519.
Physical Computing, Lesson 2: Comparing Signals (Time Domain), Mar. 12, 2024, 1 page.
Ledowski et al., "Analgesia nociception index: evaluation as a new parameter for acute postoperative pain", British Journal of Anaesthesia 111 (4): 627-9 (2013).
Li et al., "Focal Mechanism Determination Using High Frequency Waveform Matching and Its Application to Small Magnitude Induced Earthquakes", Geophysical Journal International, vol. 184, Issue 3, Mar. 2011, pp. 1261-1274, https://doi.org/10.1111/j.1365-246X.2010.04903.x.
Ma et al., "Template matching for simple waveforms with low signa-lto-noise ratio and its application to icequake detection", Earthq Sci (2020)33: 256-263.
Martini et al., "Ability of the Nociception Level, a Multiparameter Composite of Autonomic Signals, to Detect Noxious Stimuli during Propofol-Remifentanil Anesthesia", Anesthesiology, vol. 123, No. 3, Sep. 2015, pp. 524-534.
Medasense, "Introducing the NOL® (Nociception Level) Index Algorithm A Technical Overview", 2022, 11 pages.
Meijer et al., "Reduced postoperative pain using Nociception Level-guided fentanyl dosing during sevoflurane anaesthesia: a randomised controlled trial", British Journal of Anaesthesia, 125 (6): 1070e1078 (2020).
Mirza et al., "Closed-Loop Implantable Therapeutic Neuromodulation Systems Based on Neurochemical Monitoring", Frontiers in Neuroscience, vol. 13, Article 808, Aug. 2019, pp. 1-18.
Naranjo-Hernandez, "Sensor Technologies to Manage the Physiological Traits of Chronic Pain: A Review", Sensors 2020, 20, 365; doi:10.3390/s20020365.
Nelson et al., "Wireless Technologies for Implantable Devices", Sensors (Basel), vol. 20 (16) Aug. 2020, 27 pages.
Nijhuis et al., "First Report on Real-World Outcomes with Evoked Compound Action Potential (ECAP)-Controlled Closed-Loop Spinal Cord Stimulation for Treatment of Chronic Pain", Pain Ther (2023) 12:1221-1233.
O'Leary et al., "NURIP: Neural Interface Processor for Brain-State Classification and Programmable-Waveform Neurostimulation", IEEE Journal of Solid-State Circuits, 2018, 13 pages.
Osborne, "Scientists Decode Brain Waves Linked to Chronic Pain", Smithsonianmag.com, May 24, 2023, 4 pages.
Parker et al., "Evoked Compound Action Potentials Reveal Spinal Cord Dorsal Column Neuroanatomy", Basic Research, vol. 23, issue 1, Jan. 2020, pp. 82-95.
Patterson et al., "Objective wearable measures correlate with self-reported chronic pain levels in people with spinal cord stimulation systems", npj Digital Medicine (2023) 6:146 ; https://doi.org/10.1038/s41746-023-00892-x.

* cited by examiner

NEUROMODULATION WAVEFORM WATERMARKING AND PRESCRIBING

CROSS-REFERENCE TO RELATED APPLICATIONS

This application is a continuation-in-part of U.S. application Ser. No. 18/229,743, titled "Adaptive Pain Syndrome Management," filed by Sayed Emal Wahezi, on Aug. 3, 2023, which claims the benefit of U.S. Provisional Application No. 63/456,806, titled "OPEN LABEL SPINAL CORD STIMULATION IMPLANTABLE PULSE GENERATOR," filed by Sayed Emal Wahezi, on Apr. 3, 2023, and this application incorporates the entire contents of the above-referenced applications herein by reference.

TECHNICAL FIELD

The present disclosure generally relates to the field of pain syndrome management by spinal cord stimulation (SCS) using a pulse generator.

BACKGROUND

Neuromodulation refers to regulating nervous system activity through the delivery of a stimulus, such as electrical stimulation or pharmaceutical agents directly to a target area in the body of a patient. Spinal cord stimulation (SCS) is a form of neuromodulation, involving delivery of electrical energy using one or more waveforms to the spinal cord to alter the sensation of pain. Various predetermined commercially available waveforms may be used to alter sensation of pain. One or more waveforms may be selected for use depending upon the clinical effectiveness of the waveforms to alter the sensation of pain. Altering pain sensation may be achieved through an implantable pulse generator (IPG) surgically placed under the skin and electrically connected to the spinal cord via one or more leads.

One challenge in using SCS to treat chronic pain syndromes is the potential of the pain syndrome to develop tolerance to neuromodulation over time. Pain syndrome tolerance to neuromodulation waveforms is a phenomenon where the patient's pain syndrome becomes less responsive to one or more programmed stimulation parameters prescribed by a physician. Pain syndrome tolerance to a neuromodulation waveform may lead to a decrease in the effectiveness of the treatment. For example, the patient may not experience effective pain relief after the pain syndrome develops tolerance to a specific neuromodulation waveform.

In some cases of pain syndrome tolerance to neuromodulation, a waveform that was effective to relieve pain for a patient in the past may fail in current treatment to relieve pain. The loss of pain relief effect from one or more neuromodulation waveforms may be permanent for the patient. Even increasing the intensity of neuromodulation waveforms that previously relieved pain for the patient may fail to achieve effective pain relief if the patient's pain syndrome develops tolerance to the originally prescribed neuromodulation waveforms. Using a combination of different waveforms, frequencies, and intensities of neuromodulation may help improve pain relief and reduce the pain syndrome's development of tolerance to the neuromodulation.

Selecting and adjusting neuromodulation waveforms to improve pain relief and reduce the pain syndrome's development of tolerance to neuromodulation is a trial-and-error process. Such selection and adjustment of neuromodulation waveforms may require multiple visits to a clinic for adjustments by the physician or a clinician. Applying a different waveform recommended by the physician may require surgical explanation (removal) of an Implantable Pulse Generator (IPG) from a patient and implantation of a different IPG configured to apply SCS using another recommended waveform. This can be time-consuming and inconvenient for the patient and the clinician. The patient and physician may expend significant time and effort, and the patient may experience unnecessary pain, while trying different waveforms, frequencies, and intensities of stimulation to improve pain relief and reduce development of pain syndrome tolerance to neuromodulation waveforms. Changing IPGs is an expensive process as well; patients and insurances are burdened by the cost of replacing the device.

SUMMARY

Disclosed apparatus and associated methods relate to collecting signal data sampled using an input electrode contacting a patient while a neuromodulation device (NMD) applies a neuromodulation waveform using an output electrode contacting the patient, identifying characteristics of the applied neuromodulation waveform determined as a function of the collected signal data, and generating a notification if the applied neuromodulation waveform matches any known predetermined neuromodulation waveform, based on the identified characteristics. The applied neuromodulation waveform may include waveform identification data. The waveform identification data may be a watermark added by the NMD. Identification data may be encoded by varying amplitude or timing of the applied neuromodulation waveform or by modulating a carrier wave added to the applied neuromodulation waveform. An implementation may advantageously detect use of proprietary neuromodulation waveforms in real time, permitting automatic invoicing and treatment protocol conformance verification triggered by usage detection and increasing access to effective neuromodulation waveforms.

An exemplary neuromodulation device may be configured to treat a pain syndrome based on applying a prescribed waveform to a patient, while measuring patient physiological parameters in a feedback loop using sensors and triggering a change of the prescribed waveform to an adapted waveform, in response to detecting a change in the tolerance of the pain syndrome to the prescribed waveform. The neuromodulation device may be, for example, a Spinal Cord Stimulation Implantable Pulse Generator (SCS IPG). The SCS IPG may be configured to receive a digital indication to apply the prescribed waveform to the patient using output electrodes until a predetermined time while measuring signal characteristics of the applied waveform using input electrodes. The SCS IPG may compare the measured signal characteristics to signal characteristics of a predetermined waveform to determine if the applied waveform matches the predetermined waveform and send an indication the predetermined waveform is in use.

The above-described and other features and advantages realized through the techniques of the present disclosure will be better appreciated and understood with reference to the following detailed description, drawings, and appended claims. Additional features and advantages are realized through the techniques of the present invention. Other embodiments and aspects of the invention are described in detail herein and are considered a part of the claimed invention.

BRIEF DESCRIPTION OF THE DRAWINGS

The subject matter that is regarded as the invention is particularly pointed out and distinctly claimed in the claims at the conclusion of the specification. FIGS. 16-30 are new and FIGS. 1A-15 were previously disclosed. The foregoing and other objects, features, and advantages of the invention are apparent from the following detailed description of exemplary embodiments of the present invention taken in conjunction with the accompanying drawings in which:

FIG. 16 depicts an exemplary neuromodulation waveform watermarking and prescribing system configured to collect signal data sampled using an input electrode contacting a patient while a neuromodulation device (NMD) applies a neuromodulation waveform using an output electrode contacting the patient, identify signal characteristics of the applied neuromodulation waveform determined as a function of the collected signal data, and generate a notification if the applied neuromodulation waveform matches any known predetermined neuromodulation waveform, based on the identified signal characteristics.

FIG. 17 depicts a structural block diagram of an exemplary waveform prescription deployment server configured to receive a digital prescription to apply a prescribed neuromodulation waveform to a patient using a neuromodulation device, request biometric patient authentication by a computing device associated with the neuromodulation device and in response to receiving an indication of successful patient authentication, activating the neuromodulation device to apply the prescribed neuromodulation waveform to the patient, based on sending to the neuromodulation device a time-based one-time-password generated from a shared secret key distributed during a registration phase.

FIG. 18 depicts a structural block diagram of an exemplary waveform identification server configured to receive collected signal data, identify signal characteristics or an embedded watermark in an applied neuromodulation waveform determined as a function of the collected signal data, and generate a notification if the applied neuromodulation waveform or watermark matches any known predetermined neuromodulation waveform or watermark, based on the identified signal characteristics.

FIG. 19 depicts a structural block diagram of an exemplary discrete collection device configured to collect signal data sampled using an input electrode contacting a patient while a separate neuromodulation device (NMD) applies a neuromodulation waveform using an output electrode contacting the patient.

FIG. 20 depicts a process flow of an exemplary waveform prescription deployment process to receive a digital prescription for a neuromodulation device to apply a prescribed neuromodulation waveform to a patient, request biometric patient authentication by a computing device associated with the neuromodulation device and in response to receiving an indication of successful patient authentication, activating the neuromodulation device to apply the prescribed neuromodulation waveform to the patient, based on sending to the neuromodulation device a time-based one-time-password generated from a shared secret distributed during a registration phase.

FIG. 21 depicts a process flow of an exemplary waveform identification process to receive collected signal data, identify signal characteristics or an embedded watermark in an applied neuromodulation waveform determined as a function of the collected signal data, and generate a notification if the applied neuromodulation waveform or watermark matches any known predetermined neuromodulation waveform or watermark, based on the identified signal characteristics.

FIG. 22 depicts a process flow of an exemplary neuromodulation treatment management process to receive from a waveform identification server an indication that a known predetermined neuromodulation waveform is in use by a neuromodulation device treating a patient, authenticate the patient based on biometric input, generate a security token derived from the successful patient authentication and a shared secret, send the security token to a waveform prescription deployment server with a request for approval to continue treating the patient using the known predetermined neuromodulation waveform and in response to receiving the approval from the waveform prescription deployment server, activating the neuromodulation device to continue applying the prescribed neuromodulation waveform to the patient, based on sending to the neuromodulation device a time-based one-time-password generated from the shared secret distributed during a registration phase.

FIG. 23 depicts an exemplary burst neuromodulation waveform.

FIG. 24 depicts an exemplary tonic neuromodulation waveform.

FIG. 25 depicts an exemplary watermarked burst neuromodulation waveform with watermark data encoded by frequency modulation (FM).

FIG. 26 depicts an exemplary watermarked tonic neuromodulation waveform with watermark data encoded by frequency modulation (FM).

FIG. 27 depicts an exemplary watermarked burst neuromodulation waveform with watermark data encoded by amplitude modulation (AM).

FIG. 28 depicts an exemplary watermarked tonic neuromodulation waveform with watermark data encoded by amplitude modulation (AM).

The detailed description explains exemplary embodiments of the present invention, together with advantages and features, by way of example with reference to the drawings, in which similar numbers refer to similar parts throughout the drawings. The flow diagrams depicted herein are just examples. There may be many variations to these diagrams, or the steps (or operations) described therein without departing from the spirit of the invention. For instance, the steps may be performed in a differing order, or steps may be added, deleted, or modified. All these variations are considered to be within the scope of the claimed invention.

Like reference symbols in the various drawings indicate like elements.

DETAILED DESCRIPTION

While the specification concludes with claims defining the features of the invention that are regarded as novel, it is believed that the invention will be better understood from a consideration of the description of exemplary embodiments in conjunction with drawings. It is of course to be understood that the embodiments described herein are merely exemplary of the invention, which can be embodied in various forms. Therefore, specific structural and functional details disclosed in relation to the exemplary embodiments described herein are not to be interpreted as limiting, but merely as a representative basis for teaching one skilled in the art to variously employ the present invention in virtually any appropriate form, and it will be apparent to those skilled in the art that the present invention may be practiced without these specific details. Further, the terms and phrases used herein are not intended to be limiting but rather to provide an understandable description of the invention.

Figure 1A:
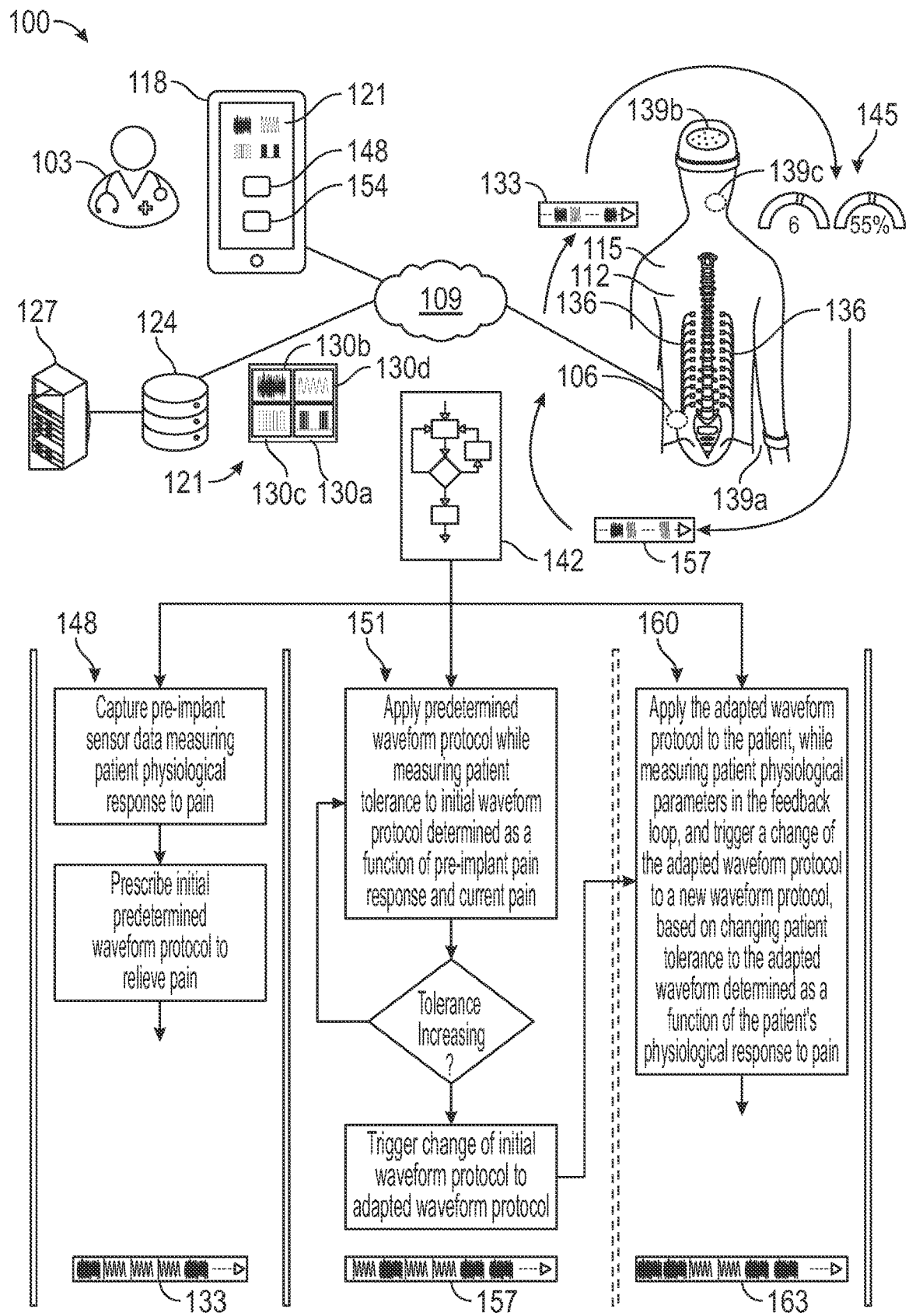
FIGS. 1A-1B depict illustrative operational scenarios wherein a doctor uses an exemplary Open Label Spinal Cord Stimulation (SCS) Implantable Pulse Generator (IPG) configured to apply a predetermined waveform protocol to a patient to treat a pain syndrome, while measuring patient physiological parameters in a feedback loop using sensors and triggering a change of the predetermined waveform protocol to an adapted waveform protocol, in response to detecting a change in the tolerance of the pain syndrome to the predetermined waveform protocol.
Figure 1B:
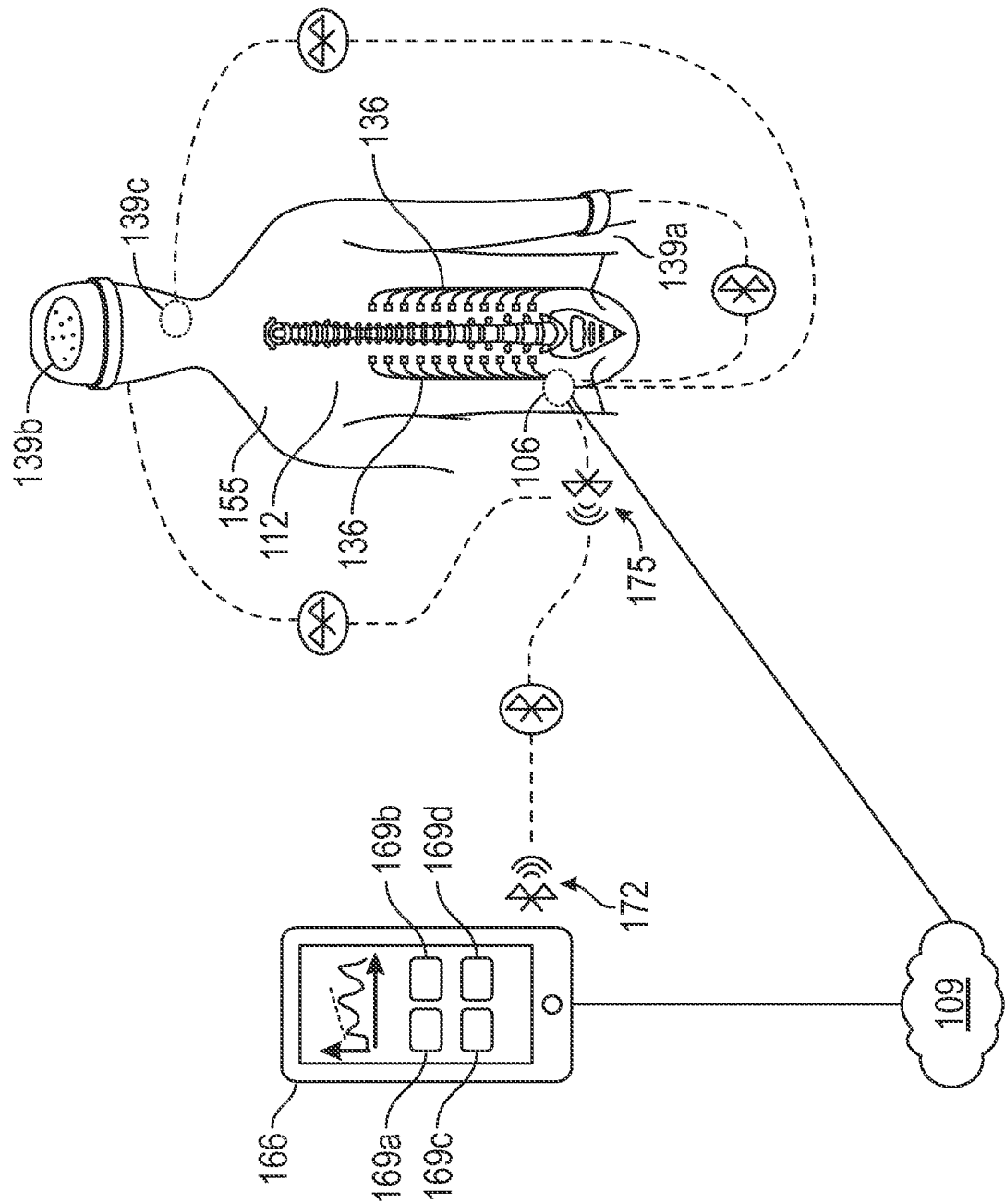

FIGS. 1A-1B depict illustrative operational scenarios wherein a doctor uses an exemplary Open Label Spinal Cord Stimulation (SCS) Implantable Pulse Generator (IPG) configured to apply a predetermined waveform protocol to a patient to treat a pain syndrome, while measuring patient physiological parameters in a feedback loop using sensors and triggering a change of the predetermined waveform protocol to an adapted waveform protocol, in response to detecting a change in the tolerance of the pain syndrome to the predetermined waveform protocol. In the exemplary neuromodulation episode 100 depicted by FIG. 1A, the doctor 103 uses the exemplary Implantable Pulse Generator (IPG) 106 via the network cloud 109 to treat the spinal cord 112 of the patient 115. In the depicted implementation the doctor 103 uses the mobile device 118 to access a library of individually available predetermined waveforms 121. The mobile device 118 is configured with an application structured to permit the doctor 103 to prescribe a selection of the individually available predetermined waveforms 121 stored in the waveform database 124. The waveform authentication and access authorization server 127 is configured to digitally authenticate each waveform of the individually available predetermined waveforms 121.

For example, the waveform authentication and access authorization server 127 is configured to digitally certify each waveform of the individually available predetermined waveforms 121 is a known waveform having specific signal characteristics. In the present disclosure a predetermined waveform or predetermined waveform protocol may be synonymous with and interchangeably referred to as a known waveform or known waveform protocol. The individually available predetermined waveforms 121 may comprise one or more licensed waveforms. The waveform authentication and access authorization server 127 is configured to authorize the IPG 106 to use any of the individually available predetermined waveforms 121 prescribed by doctor 103. The waveform authentication and access authorization server 127 may provide a digital authorization indication to the IPG 106 authorizing the IPG 106 to use one or more of the individually available predetermined waveforms 121.

For example, the digital authorization indication from the waveform authentication and access authorization server 127 to the IPG 106 may authorize the IPG 106 to download and use one or more of the individually available predetermined waveforms 121 prescribed by the doctor 103 to treat the patient 115. The IPG 106 may be configured by the doctor 103 to use one or more of the individually available predetermined waveforms 121 for a period of time governed by a digital prescription digitally signed by the doctor. In another example, the IPG 106 may be configured to apply one or more waveforms prescribed by the doctor 103 until a prescription expiration time. The IPG 106 may revert from applying a prescribed waveform to applying a default waveform or default combination of waveforms when a prescription expires.

In the depicted implementation, the individually available predetermined waveforms 121 stored in the waveform database 124 comprise the exemplary licensed waveforms 130a, 130b, 130c and 130d. In the depicted implementation the waveforms 130a, 130b, 130c and 130d are non-limiting illustrative example waveforms. The individually available predetermined waveforms 121 stored in the waveform database 124 may comprise any waveform. In the depicted implementation, the doctor 103 prescribes the initial predetermined waveform protocol 133 to relieve patient 115 pain. In the depicted implementation, the initial predetermined waveform protocol 133 comprises the individual licensed waveform 130a and the individual licensed waveform 130b. The mobile device 118 configures the IPG 106 to download the prescribed predetermined waveform protocol 133. The IPG 106 is configured to use the initial predetermined waveform protocol 133 to energize the electrodes 136 for treating the patient 115 spinal cord 112.

In the depicted implementation, the IPG 106 applies the initial predetermined waveform protocol 133 based on cycling or alternating the individual licensed waveform 130a and the individual licensed waveform 130b in a pattern specifically prescribed in a user interface by the doctor 103. In the depicted scenario the patient 115 has a pain syndrome 134 comprising one or more condition causing pain. The patient 115 pain syndrome 134 may develop tolerance 135 to one or more waveform over time. In an illustrative example, patient 115 may not experience effective pain relief after the pain syndrome 134 develops tolerance 135 to a waveform. Pain syndrome 134 tolerance 135 to the predetermined waveform protocol 133 may increase with time, causing the patient 115 to experience increasing pain as the waveform protocol 133 effectiveness declines. The specific cycling or alternating pattern prescribed may be prescribed by the doctor 103 to relieve the patient 115 pain while preventing the patient 115 pain syndrome 134 from developing tolerance 135 to an individual waveform or a predetermined waveform protocol. The IPG 106 may be configured to download and run predetermined waveforms in algorithmically determined waveform protocols. The IPG 106 may run the predetermined waveforms individually or in combination, and/or in series or parallel.

In the depicted implementation, the IPG 106 is configured to measure patient 115 physiological parameters 146 based on sensor data 145 in the feedback loop 143 and trigger a modification of the predetermined waveform protocol 133 to an adapted waveform protocol 157, based on tolerance 135 of the pain syndrome 134 to the predetermined waveform protocol 133. In the depicted implementation, tolerance 135 of the pain syndrome 134 to the predetermined waveform protocol 133 is determined in the feedback loop 143 as a function of the physiological parameters. The depicted IPG 106 is configured to determine the patient 115 physiological parameters based on sensor data.

For example, the IPG 106 is configured to receive heart rate (HR), heart rate variability (HRV), RR Interval (RR) and body temperature measurements from sensors 139 configured in wrist band 139a. The IPG 106 is configured to measure changes in brain activity (for example to monitor REM sleep) using the hat 139b configured with EEG sensors and the vagal and hypoglossal sleep sensor/stimulator 139c. The IPG 106 may be configured with sensors 139 (for example an accelerometer or magnetometer) measuring parameters related to physical activity (for example resting or walking) or body position (for example lying down sitting).

The IPG 106 may also be configured to autonomously change waveforms or sequences of waveforms based on measuring specific changes in patient physiology based on the sensor data 145. The IPG 106 may be configured to autonomously change waveforms or waveform signal characteristics, such as for example, waveform frequency, amplitude, power or duty cycle depending on physiologic parameters 146 that indicate increased pain. The IPG 106 may physiologically interact bidirectionally with the patient 115. For example, the IPG 106 may be configured to receive information from the sensors 139 to change spinal cord activity and deliver information to the EEG and sleep sensors to alter sleep and provide extracranial therapy. In the depicted implementation, the IPG 106 is configured with the waveform protocol prescription engine (WPPE) 142. In the illustrated implementation the WPPE 142 applies the predetermined waveform protocol 133 to the patient 115, while measuring the physiological response of the patient 115 to pain based on the sensor data 145. In the depicted implementation, the WPPE 142 may detect a change in the patient 115 physiological response to pain while measuring patient 115 physiological parameters 145 in the feedback loop 143. In the depicted implementation the WPPE 142 may determine the detected change in the patient 115 physiological response to pain indicates the efficacy of the predetermined waveform protocol 133 to relieve pain has decreased as result of increased patient 115 pain syndrome 134 tolerance 135 to the predetermined waveform protocol 133. In another illustrative example, the WPPE 142 may determine the patient 115 pain syndrome 134 tolerance 135 has increased relative to preset, pre-implantation patient 115 physiological data. The pre-implantation patient 115 physiological data may be captured during the neuromodulation trial procedure 148 initiated by the doctor 103 using the trial 148 button configured in the mobile device 118.

During the exemplary neuromodulation trial procedure 148 the IPG 106 may be configured to capture pre-implant sensor data measuring the patient 115 physiological response to pain while applying one or more prescribed waveform to the patient 115 as a baseline or reference pain response for the patient 115. The doctor 103 may prescribe the initial predetermined waveform protocol 133 to relieve pain for the patient 115, based on the neuromodulation trial procedure 148. The reference pain response for the patient 115 measured using the pre-implant sensor data correlates with the initial efficacy of the prescribed waveform applied while the reference pain response was captured. In an illustrative example the IPG 106 may be configured with the pre-implantation patient 115 physiological data corresponding to the baseline or reference physiological response to pain for the patient 115.

In the depicted implementation, the doctor 103 may initiate the neuromodulation treatment 151 procedure using the treat 154 button configured in the mobile device 118. During the exemplary neuromodulation treatment procedure 151 the WPPE 142 applies the predetermined waveform protocol 133 while measuring patient 115 pain syndrome 134 tolerance 135 to the waveform determined as a function of pre-implant reference pain response and current pain response. In a feedback loop the WPPE 142 performs a test to determine if the patient 115 pain syndrome 134 tolerance 135 to the predetermined waveform protocol 133 has increased (that is, a decrease in efficacy of the prescribed waveform 133 to relieve pain in the patient 115) corresponding with an increase in the patient 115 physiological response to pain measured using the sensor data 145. In the depicted example the increased patient 115 pain syndrome 134 tolerance 135 to the predetermined waveform protocol 133 triggers WPPE 142 to change the predetermined waveform protocol 133 to the adapted waveform protocol 157. In the depicted implementation, the WPPE 142 continues long term neuromodulation treatment 160 applying the adapted waveform protocol 157 to the patient 115 while measuring patient physiological parameters 146 in the feedback loop 143. The WPPE 142 triggers a change of the adapted waveform protocol 157 to the modified treatment waveform protocol 163 based on changing patient 115 pain syndrome 134 tolerance 135 to the adapted waveform protocol 157 determined as a function of the patient 115 physiological response to pain measured using the sensor data 145.

In FIG. 1B, is a schematic illustration of sensors and effectors 139a,b,c configured for bidirectional information flow with the SCS IPG 106 to change spinal cord 112 activity with the effectors 139 and mitigate a pain crisis based on adjusting the stimulation form the effector in response to sensor information indicating the pain crisis. The method may further comprise: receiving sensor information 145 comprising the physiological response of the patient 115 to pain from at least one sensor, using the SCS IPG 106 processor 200; comparing the received sensor information 145 from at least one sensor to reference sensor information comprising the physiological response of the patient 115 captured when the patient 115 was not experiencing a pain crisis, to determine if the patient is experiencing a pain crisis based on the comparison, using the SCS IPG 106 processor 200; in response to determining the patient 115 is experiencing a pain crisis, activating at least one effector 139 configured to change spinal cord 112 activity based on providing external stimulation to the patient 115, using the SCS IPG 106 processor 200; and adjusting the external stimulation to the patient 115 to mitigate the pain crisis, using the SCS IPG 106 processor 200.

In one embodiment, the SCS IPG 106 has a direct connection to the spinal cord 112 with an IPG capable of pairing with different sensors. In one embodiment, a wristband 139a, digital EEG hat 139b and/or vagal stimulator 139c may be communicatively paired with the SCS IPG 106 and a mobile device 166 using the BLUETOOTH links 172 and 175. The mobile device 166 may be configured with a mobile app designed to monitor patient physiological parameters such as, for example, blood pressure, oxygen tension, heart rate and RR interval. For example the patient's measured blood pressure, oxygen tension, heart rate and RR interval may be presented to the patient using displays 169a,b,c,d configured in the mobile app hosted by the mobile device 166. The SCS IPG 106 or the mobile device 166 may correlate an increase in heart rate with a change in oxygen tension measured by the sensors. This detected change in pain response may be detected and recorded by the SCS IPG 106 or the mobile device 166 based on sensor data received from the wristband device and/or other sensors. In an illustrative example, the SCS IPG 106 or the mobile device 166 may be configured to provide a response to the change in pain response such as but not limited to an acupressure treatment using the wristband device and/or music or other content triggered in the mobile app to calm the patient. This wrist wearable device may also be used as a monitoring device to record moment-to-moment changes such as when a patient becomes very anxious in response to pain or PTSD. The wrist wearable device may also provide biofeedback. as a type of cognitive behavioral therapy whereby a patient can see their heart rate and their oxygen tension and other physiological parameters on the mobile app screen. In one embodiment, a sensor device may not be wearable, but may be external to the IPG and configured as the vagal nerve stimulator 139c. In this embodiment, the devices may interface with all of these other devices, and the vagal nerve stimulator.

Figure 2:
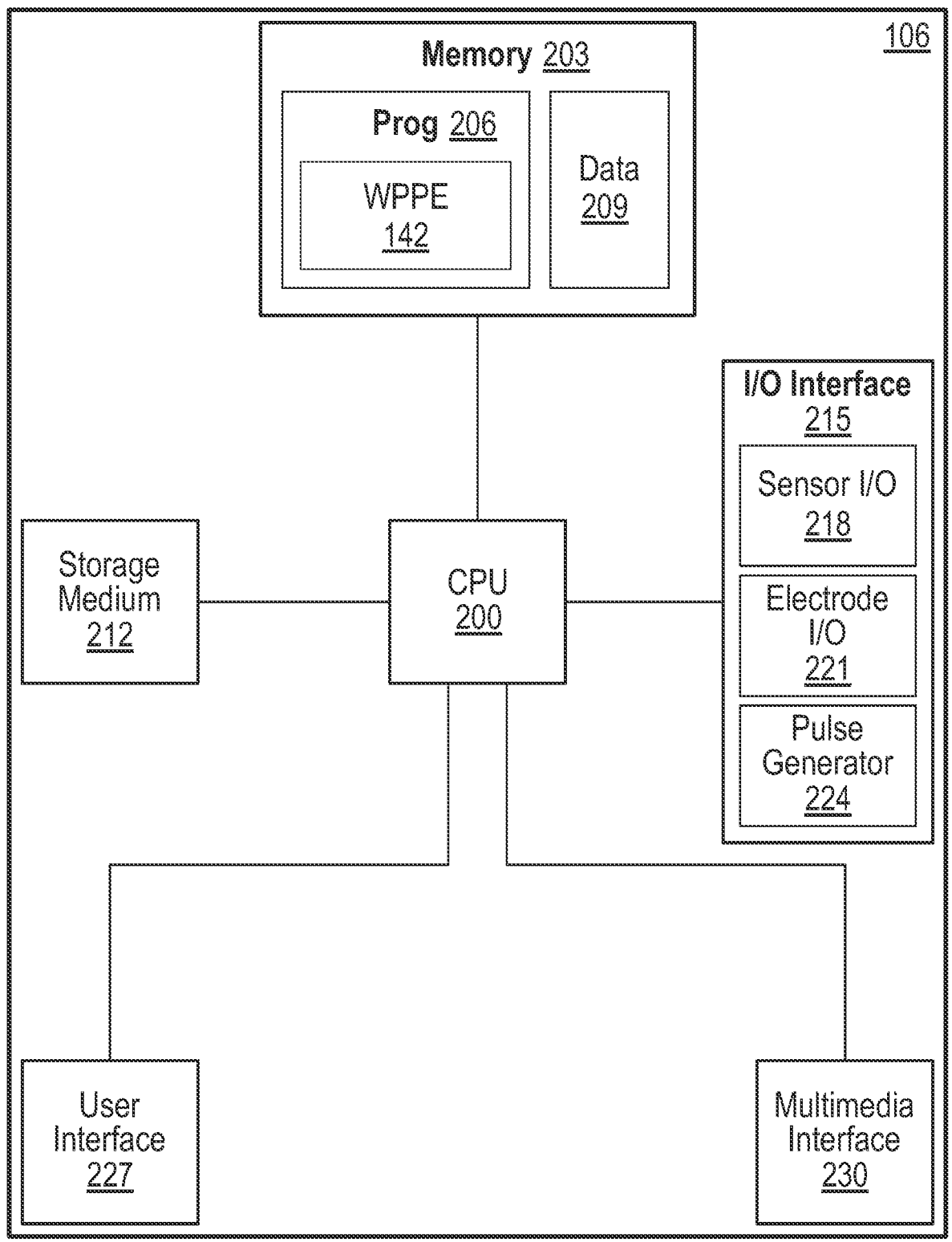
FIG. 2 depicts a block diagram of an exemplary Open Label SCS IPG hosting an exemplary waveform protocol prescription engine (WPPE) configured to apply a predetermined waveform protocol to a patient to treat a pain syndrome, while measuring patient physiological parameters in a feedback loop using sensors and trigger a change of the predetermined waveform protocol to an adapted waveform protocol, in response to detecting a change in the tolerance of the pain syndrome to the predetermined waveform protocol.

FIG. 2 depicts a block diagram of an exemplary Open Label SCS IPG hosting an exemplary waveform protocol prescription engine (WPPE) configured to apply a predetermined waveform protocol to a patient to treat a pain syndrome, while measuring patient physiological parameters in a feedback loop using sensors and trigger a change of the predetermined waveform protocol to an adapted waveform protocol, in response to detecting a change in the tolerance of the pain syndrome to the predetermined waveform protocol. In FIG. 2, the block diagram of the exemplary SCS IPG 106 includes the CPU (processor) 200 and the memory 203. In the depicted implementation, the processor 200 is in electrical communication with the memory 203. The processor 200 may be operably coupled with one or more memory 203 via a communication network. In the depicted implementation the memory 203 includes the program memory 206 and the data memory 209. The depicted program memory 206 includes processor-executable program instructions implementing WPPE 142. In some embodiments, the illustrated program memory 206 may include processor-executable program instructions configured to implement an OS (Operating System). In various embodiments, the OS may include processor executable program instructions configured to implement various operations when executed by the processor 200. In some embodiments, the OS may be omitted. In some embodiments, the illustrated program memory 206 may include processor-executable program instructions configured to implement various Application Software. In various embodiments, the Application Software may include processor executable program instructions configured to implement various operations when executed by the processor 200. In some embodiments, the Application Software may be omitted. In the depicted embodiment, the processor 200 is communicatively and operably coupled with the storage medium 212. The storage medium 212 may be configured to implement various data storage and data retrieval operations for the processor 200 such as for example, read/write, read/only or non-volatile storage and retrieval. In the depicted embodiment, the processor 200 is communicatively and operably coupled with the I/O (Input/Output) interface 215. In the depicted embodiment, the I/O interface 215 includes a network interface. In various implementations, the network interface may be a wireless network interface. In some designs, the network interface may be a Wi-Fi interface. In some embodiments, the network interface may be a BLUETOOTH interface. In an illustrative example, the SCS IPG 106 may include more than one network interface. In some designs, the network interface may be a wireline interface. In some designs, the network interface may be omitted. In the depicted implementation the I/O interface 215 includes the sensor I/O interface 218. The sensor I/O interface 218 may be configured to receive sensor information from one or more sensor configured to measure one or more physiological parameters. The sensor information may be received by the I/O interface 218 using one or more wired or wireless interface. The sensor I/O interface 218 may be configured to send information to one or more effector configured to provide physical stimulation to a patient. The information sent to the one or more effectors from the I/O interface 218 may control one or more parameter of the stimulation for example, the rate, intensity, frequency or time period of the physical stimulation provided by the one or more effector.

In the depicted implementation, the processor 200 is operably coupled with the sensor I/O interface 218. In the depicted implementation the I/O interface 215 includes the electrode I/O interface 221. The electrode I/O interface 221 may be configured to energize one or more electrode operably coupled with the electrode I/O interface 221. The one or more electrodes may be grouped into one or more sets of individual electrodes which may be energized with the same and/or distinct and separate waveforms at the same time as configured by the processor 200.

The electrode I/O interface 221 may be configured to receive input energy form one or more electrodes operably coupled with the I/O interface 221. The input energy from the one or more electrodes may be used by the processor 200 to measure energy applied with the SCS IPG 106 by one or more waveform. In the depicted implementation, the processor 200 is operably coupled with the electrode I/O interface 221. In the depicted implementation the I/O interface 215 includes the pulse generator 224. The pulse generator 224 may be configured to generate any arbitrary waveform to be applied using the electrode I/O interface 221. The electrode I/O interface 221 may include a digital-to-analog converter configured to convert a neuromodulation waveform signal stored in digital form into electrical output energy to one or more output electrodes electrically connected to the electrode I/O interface 221. The digital-to-analog resolution may be configurable by the processor 200. The electrode I/O interface 221 may include one or more filters configurable by the processor 200 as a reconstruction filter to remove frequencies above the Nyquist limit from output waveforms applied to the patient. The electrode I/O interface 221 may include one or more amplifiers with gain configurable by the processor 200. For example the processor 200 may configure the gain of one or more amplifiers to adjust the output amplitude of one or more waveforms applied to the patient.

In the depicted implementation, the processor 200 is operably coupled with the pulse generator 224. In the depicted embodiment, the processor 200 is communicatively and operably coupled with the user interface 227. In various implementations, the user interface 227 may be adapted to receive input from a user or send output to a user. In some embodiments, the user interface 227 may be adapted to an input-only or output-only user interface mode. In various implementations, the user interface 227 may include an imaging display. In some embodiments, the user interface 227 may include an audio interface. In some designs, the audio interface may include an audio input. In various designs, the audio interface may include an audio output. In some implementations, the user interface 227 may be touch-sensitive. The user interface 227 may be configured to permit graphical waveform or signal input drawn using a stylus or a user's finger, in contact with a touch-sensitive surface. In some designs, the SCS IPG 106 may include an accelerometer operably coupled with the processor 200. In various embodiments, the SCS IPG 106 may include a GPS module operably coupled with the processor 200. In an illustrative example, the SCS IPG 106 may include a magnetometer operably coupled with the processor 200. In some embodiments, the user interface 227 may include an input sensor array. In various implementations, the input sensor array may include one or more imaging sensor. In various designs, the input sensor array may include one or more audio transducer. In some implementations, the input sensor array may include a radio-frequency detector. In an illustrative example, the input sensor array may include an ultrasonic audio transducer. In some embodiments, the input sensor array may include electrical signal sensing subsystems or modules configurable by the processor 200 to be adapted to implement operations, such as for example, providing signal input capability, signal output capability, signal sampling, spectral analysis, correlation, autocorrelation, Fourier transforms, buffering, filtering operations including adjusting frequency response and attenuation characteristics of spatial domain and frequency domain filters, signal or waveform recognition, pattern recognition, or anomaly detection. In various implementations, the depicted memory 203 may contain processor executable program instruction modules configurable by the processor 200 to be adapted to implement operations, such as for example, providing signal input capability, signal output capability, signal sampling, spectral analysis, correlation, autocorrelation, Fourier transforms, buffering, filtering operations including adjusting frequency response and attenuation characteristics of spatial domain and frequency domain filters, signal or waveform recognition, pattern recognition, or anomaly detection. In some embodiments, the input sensor array may include audio sensing subsystems or modules configurable by the processor 200 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection. In various implementations, the depicted memory 203 may contain processor executable program instruction modules configurable by the processor 200 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection. In the depicted embodiment, the processor 200 is communicatively and operably coupled with the multimedia interface 230. In the illustrated embodiment, the multimedia interface 230 includes interfaces adapted to input and output of audio, video, and image data. In some embodiments, the multimedia interface 230 may include one or more still image camera or video camera. In various designs, the multimedia interface 230 may include one or more microphone. In some implementations, the multimedia interface 230 may include a wireless communication means configured to operably and communicatively couple the multimedia interface 230 with a multimedia data source or sink external to the SCS IPG 106. In various designs, the multimedia interface 230 may include interfaces adapted to send, receive, or process encoded audio or video. In various embodiments, the multimedia interface 230 may include one or more video, image, or audio encoder. In various designs, the multimedia interface 230 may include one or more video, image, or audio decoder. In various implementations, the multimedia interface 230 may include interfaces adapted to send, receive, or process one or more multimedia stream. In various implementations, the multimedia interface 230 may include a GPU. In some embodiments, the multimedia interface 230 may be omitted. The multimedia interface 230 may be implemented in a mobile device operably coupled with the processor 200. For example, the multimedia interface 230 may be configured in the doctor 103 mobile device 118 depicted at least by FIG. 1A. The multimedia interface 230 may be configured in the patient 115 mobile device 166 depicted at least by FIG. 1B. Useful examples of the illustrated SCS IPG 106 include, but are not limited to, personal computers, servers, tablet PCs, smartphones, or other computing devices. In some embodiments, multiple SCS IPG 106 devices may be operably linked to form a computer network in a manner as to distribute and share one or more resources, such as clustered computing devices and server banks/farms. In some embodiments, an exemplary SCS IPG 106 design may be realized in a distributed implementation. An SCS IPG 106 design may be partitioned between a client device, such as, for example, a phone, and, a more powerful server system with greater resources, such as for example, computation, memory or storage capacity. In various designs, a SCS IPG 106 partition hosted on a PC or mobile device may choose to delegate some parts of computation, such as, for example, machine learning or deep learning, to a host server. In some embodiments, a client device partition may delegate computation-intensive tasks to a host server to take advantage of a more powerful processor, or to offload excess work. In an illustrative example, some devices may be configured with a mobile chip including an engine adapted to implement specialized processing, such as, for example, neural networks, machine learning, artificial intelligence, image recognition, audio processing, or digital signal processing. In some embodiments, such an engine adapted to specialized processing may have sufficient processing power to implement some features. However, in some embodiments, an exemplary SCS IPG 106 may be configured to operate on a device with less processing power, such as, for example, various gaming consoles, which may not have sufficient processor power, or a suitable CPU architecture, to adequately support SCS IPG 106. Various embodiment designs configured to operate on a such a device with reduced processor power may work in conjunction with a more powerful server system.

FIGS. 3A-3F together depict various views of exemplary waveform protocol configuration, editing and prescribing graphical user interfaces. The SCS IPG 106 processor 200 may configure the pulse generator 224 (depicted at least by FIG. 2) to energize electrodes 136 (depicted at least by FIG. 1A) with one or more waveform configured or selected using interfaces such as depicted by any of FIGS. 3A-3F.

Figure 3A:
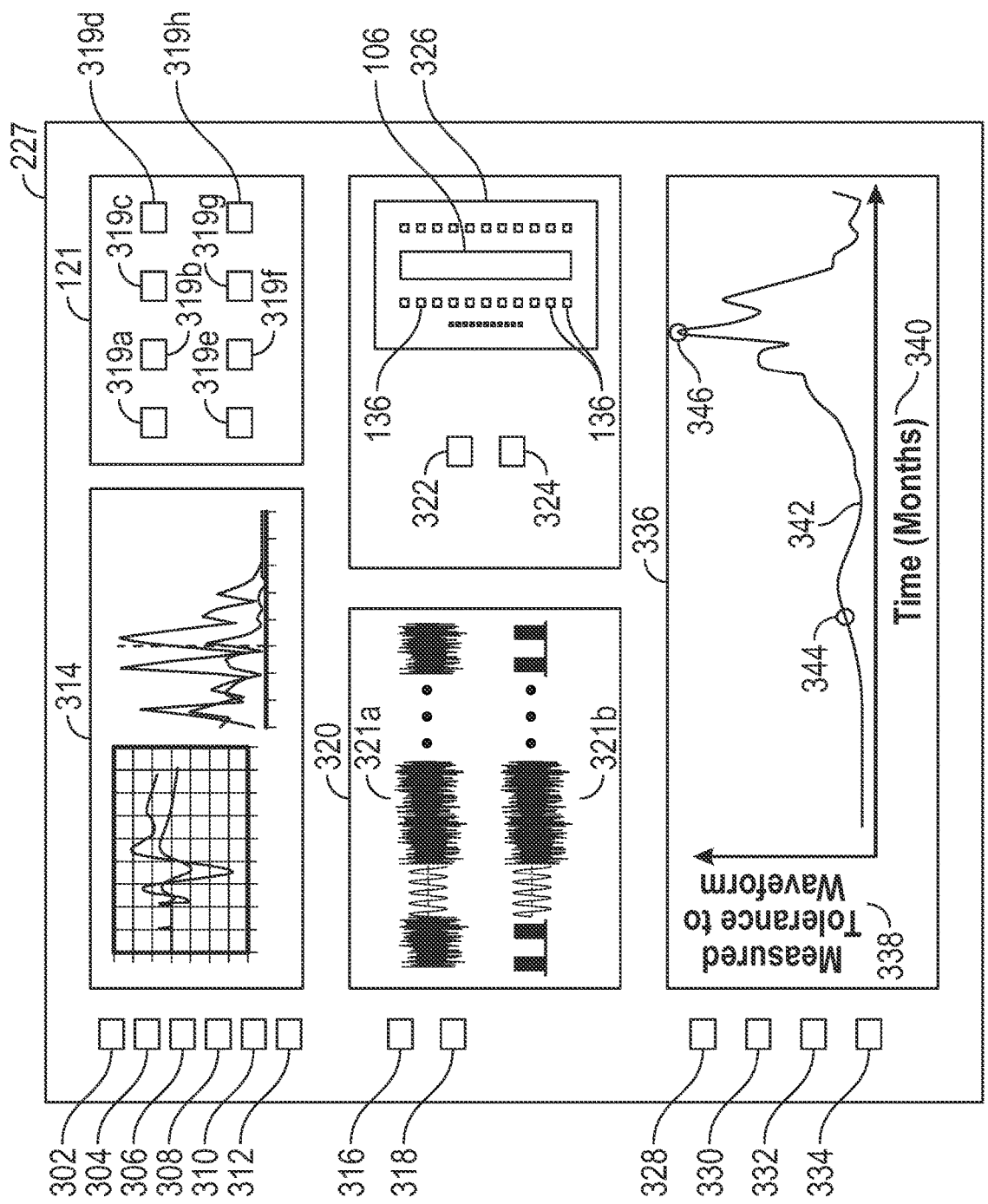
FIGS. 3A-3F together depict various views of exemplary waveform protocol configuration and prescribing graphical user interfaces.

FIG. 3A shows the exemplary user interface 227 configured for waveform and waveform protocol customization, configuration and prescribing. The exemplary graphical waveform customization interface 314 provides the configuration buttons 302, 304, 306, 308, 310, and 312 permitting a user to modify or configure respective waveform parameters such as, frequency, amplitude, running time, waveform selection, prescription expiration time, and duty cycle. The waveform parameters modified or configured by the depicted configuration buttons may be programmed by the SCS IPG 106 processor 200.

In FIG. 3A, the waveform selection buttons 319*a,b,c,d,e,f,g,h* are configured to select individual waveforms or waveform protocols from the waveform library 121 for application by the SCS IPG 106. In the implementation implemented by FIG. 3A the waveform protocol selection and configuration interface 320 is configured to permit a user to customize waveform protocols formed from individual waveforms selected from the waveform library 121. In the depicted implementation, the exemplary waveform protocols 321*a* and 321*b* have been customized from individual waveforms and stored in the SCS IPG 106. The SCS IPG 106 may be configured to apply the waveform protocols 321*a* and 321*b* using the custom waveform protocol selection buttons 316 and 318. For example, the waveform protocol selection and configuration interface 320 may be configured to retrieve individual waveforms from the waveform library 121. The individual waveforms or waveform protocols to be retrieved from the waveform library 121 may be selected for customization or configuration in a waveform protocol using the waveform selection buttons 319*a,b,c,d,e,f,g,h*. The selected waveforms may be arranged by clicking, dragging and dropping the selected waveforms in the waveform protocol selection and configuration interface 320 to compose a customized waveform protocol. For example, a waveform protocol may be formed from individual waveforms based on dragging/dropping individual waveforms into a particular pattern to form a cycling sequence of alternating distinct waveforms in the protocol selection and configuration interface 320. In an illustrative example each individual waveform in a customized waveform protocol may be configured with an on time and off time, a start time in the sequence, an end time in the sequence, and an ordinal position in the sequence, using the waveform protocol selection and configuration interface 320.

In FIG. 3A, the exemplary electrode input/output (I/O) programming interface 326 is configured to permit programming individual electrodes as input or output and assign particular waveforms and/or waveform protocols to particular output electrodes. In the depicted implementation the electrode I/O programming interface 326 may be configured to operate in conjunction with the waveform protocol selection and configuration interface 320 to permit assigning waveforms and/or waveform protocols to individual electrodes. For example the user may tap or click one or more electrode 136 displayed in the electrode I/O programming interface 326 to select multiple electrodes. In the depicted implementation the output activator 322 assigns selected electrodes to an output set to be energized with one or more waveform. In the depicted implementation the input activator 324 assigns selected electrodes to an input set for measuring received energy from one or more waveform applied to the patient. The user may select a waveform or waveform protocol in the waveform protocol selection and configuration interface 320 and assign the selected waveform or waveform protocol to the selected or grouped electrodes. In an illustrative example the SCS IPG 106 processor 200 may configure the pulse generator 224 to energize the selected or grouped electrodes with the assigned waveforms or waveform protocols. An exemplary physical IPG electrode I/O interface configurable using the electrode I/O programming interface 326 is described with reference to FIG. 11.

In FIG. 3A, the exemplary pain syndrome tolerance graphical user interface 336 is configured to present the measured pain syndrome tolerance 135 as a function of time 340. In the depicted implementation the measured pain syndrome tolerance 135 position on the dependent axis 338 represents the change in the tolerance 135 of a patient 115 pain syndrome 134 to a particular waveform or waveform protocol over time. The tolerance 135 of a patient 115 pain syndrome 134 to a particular waveform or waveform protocol at the particular time may be determined as a function of pre-implant trial phase data comprising patient 115 physiological response to pain and the patient 115 current physiological response to pain in a subsequent treatment phase. The SCS IPG 106 processor 200 may compare the pre-implant trial phase patient 115 physiological response to pain and the patient 115 current physiological response to pain to determine the tolerance 135 of the pain syndrome 134 to the particular waveform. The patient physiological response to pain is based on data from sensors configured to measure patient physiological parameters such as for example, heart rate, blood pressure, RR interval, brain waves (EEG), or oxygen tension, in the trial phase and a subsequent treatment phase. For example, the tolerance 135 of the pain syndrome 134 to a particular waveform or waveform protocol may correlate with the pain relief effect of the particular waveform or waveform protocol measured in the trial phase. In the depicted pain syndrome tolerance graphical user interface 336 the measured pain syndrome tolerance 135 as a function of time 340 is a difference between the patient physiological response to pain for a particular waveform measured in the trial phase and the current patient physiological response to pain measured during a subsequent treatment phase by the SCS IPG 106 processor 200 in the feedback loop 143. In the depicted implementation, the reference tolerance 342 is the tolerance 135 of the pain syndrome 134 established in the trial phase for the particular waveform or waveform protocol. In the depicted implementation the trigger tolerance 344 is a threshold tolerance trigger value set by the doctor 103 to trigger a change of the predetermined waveform protocol 133 to an adapted waveform protocol 157, in response to detecting the tolerance 135 of the pain syndrome 134 to the predetermined waveform protocol 133 reached the trigger point 344.

In an illustrative example, the pain syndrome tolerance 135 to a particular waveform is a difference between the patient 115 physiological response to pain for a particular waveform measured in a trial phase and a current patient physiological response to pain measured in the feedback loop during a treatment phase. A reference pain response for patient 115 is established in a pre-implant trial procedure using sensor data measuring the patient 115 physiological response to pain while applying one or more prescribed waveform to patient 115. Just after the end of the trial phase the pain syndrome tolerance 135 to a particular waveform as a function of time may be close to zero (FIG. 3A). The pain syndrome tolerance to a particular waveform as a function of time may be close to zero because just after the end of the trial phase, the reference physiological response to pain measured in the trial phase may be the same as or close to the current patient physiological response to pain measured in the feedback loop during a treatment phase, such that the difference just after the end of the trial phase may be small (i.e., comparing the reference physiological response to itself results in a difference of zero). Over time, the pain syndrome may develop tolerance to the waveform and the patient may not experience effective pain relief with the particular waveform. For example, as the pain syndrome develops tolerance to the particular waveform over time, the patient will experience decreasing pain relief from the particular waveform resulting in increasing pain and increasing patient physiological response to pain measured using the sensor data. As the patient's physiological response to pain increases, the difference between the patient physiological response to pain for the particular waveform measured in the trial phase and the current patient physiological response to pain measured in the feedback loop during the treatment phase (i.e., the pain syndrome tolerance to the particular waveform as a function of time) increases (FIG. 3A). In the feedback loop the WPPE 142 performs a test to determine if the patient 115 pain syndrome 134 tolerance 135 to the predetermined waveform protocol 133 has increased (that is, a decrease in effect of the prescribed waveform 133 to relieve pain in the patient 115) corresponding with an increase in the patient 115 physiological response to pain measured using the sensor data 145. In an illustrative example the processor 200 may determine the pain syndrome tolerance to the particular waveform as a function of time based on subtracting the patient physiological response to pain for a particular waveform measured in a trial phase from a current patient physiological response to pain measured in the feedback loop during a treatment phase. The processor 200 may determine a statistical measure of the patient physiological response to pain for a particular waveform measured in a trial phase. The processor 200 may determine a statistical measure of the patient physiological response to pain for the same particular waveform measured during a treatment phase. The statistical measure may be an average, mean, median or any other statistic. The statistical measure may be determined as a function of time. The time may be any period of time, such as days, hours, or minutes. For example, the statistical measure may be a time average. In an illustrative example, the processor 200 may subtract a time-average of heart rate over an eight-hour period during the trial phase from a heart rate over an eight-hour period at any time during the treatment phase, to determine the pain syndrome tolerance to the particular waveform as a function of time. For example, the processor 200 may subtract heart rate measured in the trial phase from heart rate measured in the feedback loop during the treatment phase to obtain the pain syndrome tolerance to the particular waveform (FIG. 3A). In a case of processing sensor data representing patient physical parameters that are not single scalar values (such as for example blood pressure having a systolic and a diastolic value), one of the values may be used, or a difference may be taken in the trial and treatment phases and the differences used by subtraction as discussed above to determine the pain syndrome tolerance to the particular waveform as a function of time. In some designs the processor 200 may determine the pain syndrome tolerance to the particular waveform using combinations of patient physical parameters known by those of ordinary skill to increase or decrease with increasing or decreasing pain. The device may trigger a change of the predetermined waveform protocol 133 to an adapted waveform protocol 157, in response to detecting the tolerance 135 of the pain syndrome 134 to the predetermined waveform protocol 133 reaches a trigger point 344. The trigger point may be set by the treating physician through the user interface.

Figure 3B:
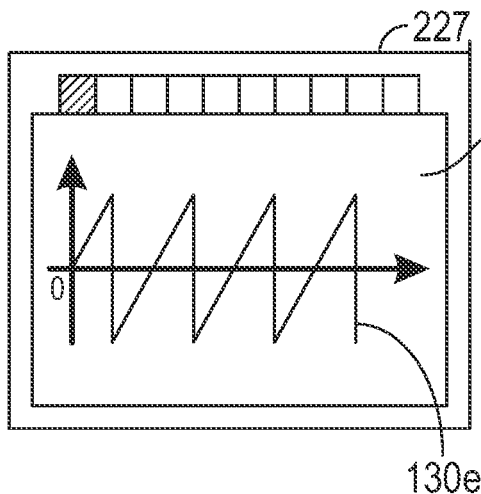
Figure 3C:
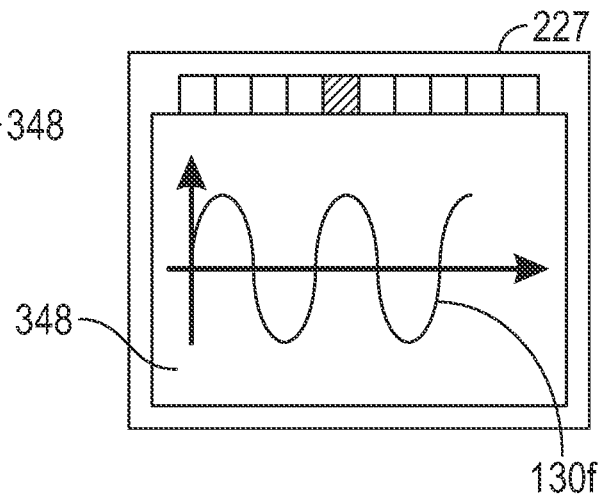
Figure 3D:
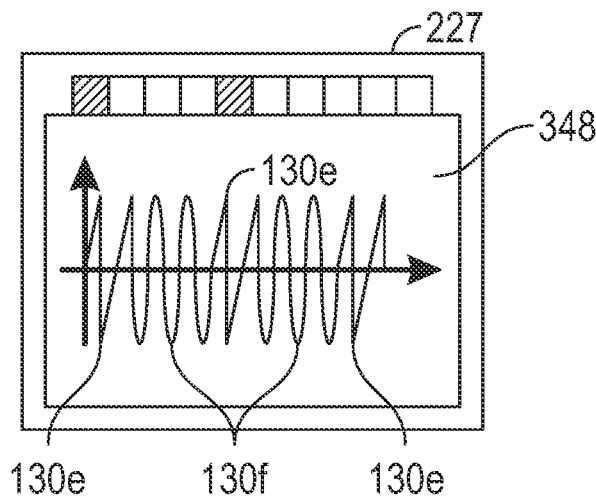
Figure 3E:
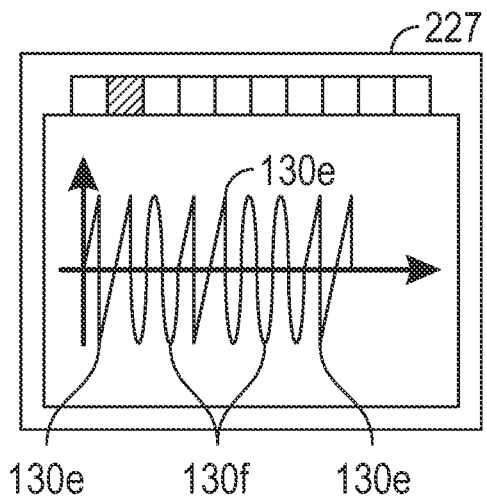
Figure 3F:
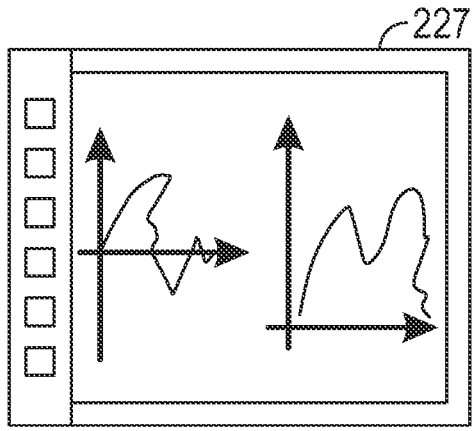

FIGS. 3B-3E are exemplary waveform configuration and selection interfaces. The waveform configuration and selection interface 346 includes the row of waveform selection tabs 348. In FIG. 3B the exemplary waveform 130*e* has been selected by tab 350 for application by the SCS IPG 106. In FIG. 3C the exemplary waveform 130*e* has been selected by tab 354 for application by the SCS IPG 106. In FIG. 3D the exemplary waveform 130*e* and waveform 130*f* have been selected by tabs 358 and 360 respectively, from the row of waveform selection tabs 356. In FIG. 3D the exemplary waveform 130*c* and waveform 130*f* have been configured in an exemplary customized waveform protocol comprising two waveforms. selected by tabs 358 and 360 respectively, from the row of waveform selection tabs 356. In FIG. 3E the exemplary waveform protocol configured in FIG. 3D has been stored in the SCS IPG 106 for section with the custom waveform protocol section tab 364 in the row of tabs 362. FIG. 3F shows a waveform customization and editing interface configured to permit a user to create and modify existing and new waveforms. In FIG. 3F the waveform customization and editing interface 356 is configured for customizing and editing the waveforms 368 and 370. The configuration buttons 372*a*, 372*b*, and 372*c* permit a user to modify parameters of the waveform 368 such as, frequency, amplitude, running time, prescription, expiration time, and duty cycle respectively. The configuration buttons 372*d*, 372*c*, and 372*f* permit a user to modify parameters of the waveform 370 such as frequency, amplitude, running time, waveform selection, prescription expiration time, and duty cycle respectively.

The tabs may be tapped/clicked by a user for selecting a particular predetermined waveform as shown in FIGS. 3B and 3C or for selecting a predetermined waveform protocol as shown in FIGS. 3D and 3E. The waveforms and waveform protocols may be loaded by the SCS IPG 106 processor 200 from the waveform library 121 shown in FIG. 1A. The individual waveforms might be, e.g., burst or contour waveforms selected by tapping different tabs. FIG. 3B shows the exemplary predetermined waveform 130e selected by the leftmost tab 350. FIG. 3C shows the predetermined waveform 130f selected by the tab fourth from the Left. FIG. 3D shows a waveform protocol consisting of the predetermined waveforms 130e and 130f selected by the leftmost tab and the tab fourth from the Left. FIG. 3E shows the waveform protocol of FIG. 3D stored as a predetermined protocol and selected by the tab second from the left. In FIG. 3E the tabs select predetermined waveform protocols each consisting of multiple waveforms. FIG. 3F is a waveform protocol editor display for customizing and creating waveform protocols. In FIG. 3F, the user can edit predetermined protocols and create/customize new protocols (e.g., run a first waveform for a first time, run a second waveform for a second time).

Figure 5:
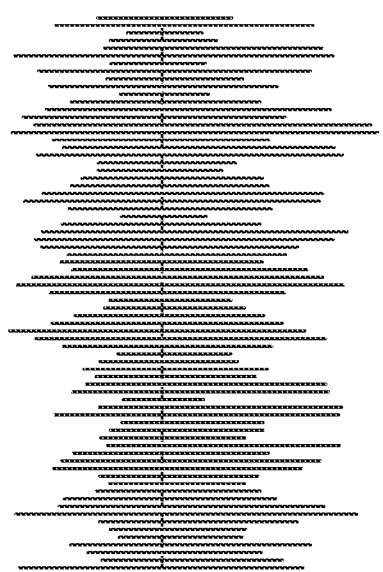
FIGS. 4-7 depict exemplary predetermined waveforms.
Figure 7:
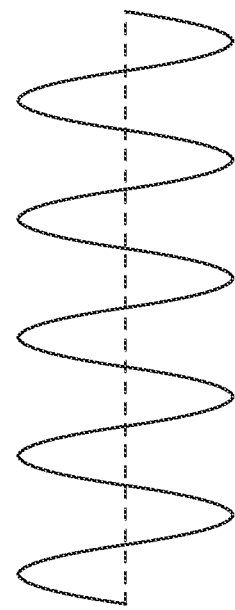
Figure 4:
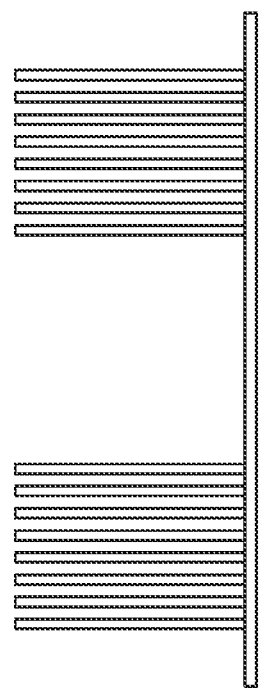
Figure 6:
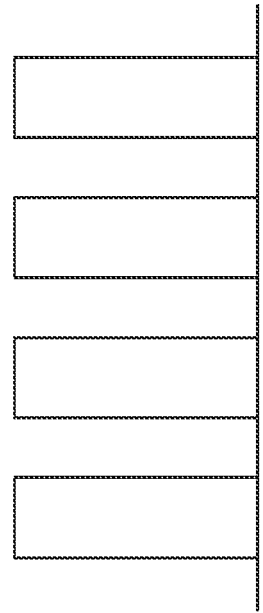

FIGS. 4-7 depict exemplary predetermined waveforms. FIG. 4 shows the exemplary waveform 130a shown in FIG. 1A. FIG. 5 shows the exemplary waveform 130b shown in FIG. 1A. FIG. 6 shows the exemplary waveform 130c shown in FIG. 1A. FIG. 7 shows the exemplary waveform 130d shown in FIG. 1A. The exemplary waveforms 130a,b,c,d are retrievably stored in the waveform library 121 shown in FIG. 1A. The depicted waveforms 130a,b,c,d are illustrative examples. The waveforms 130a,b,c,d may be any waveform retrievably stored in the waveform library 121 shown in FIG. 1A. In illustrative examples, the SCS IPG 106 may be configured to apply any waveform or waveform protocol including waveform types known in the art such as but not limited to, burst, contour, spike, High Frequency and Ultra High Frequency.

Figure 8:
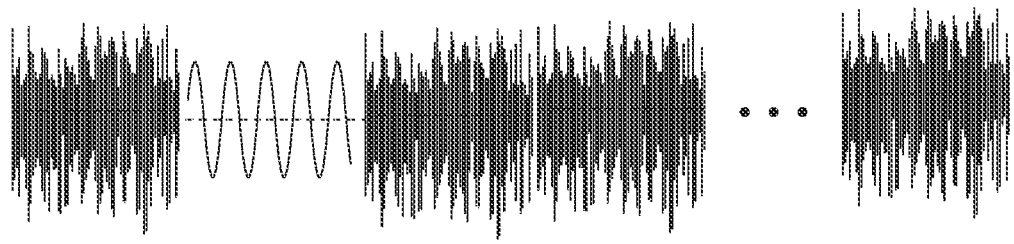
FIGS. 8-9 depict exemplary waveform protocols.
Figure 9:
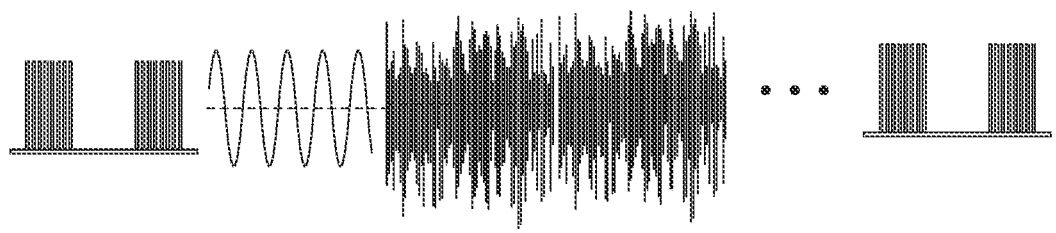

FIGS. 8-9 depict exemplary waveform protocols. In FIG. 8, the exemplary waveform protocol 800 includes the exemplary waveforms 130a and 130b. In the depicted example, the waveform protocol 800 comprises a cycling pattern of alternating waveforms including the waveforms 130a, 130b, 130a and 130a applied by the SCS IPG 106 in the depicted sequence. The waveform sequence of the waveform protocol 800 depicted in FIG. 8 repeats. The waveform sequence of the waveform protocol 800 may be configured to repeat using the SCS IPG 106 until a predetermined expiration time. The waveform protocol 800 may comprise any waveform configured by the SCS IPG 106. In the depicted example the individual waveforms of the exemplary waveform protocol 800 are applied by the SCS IPG 106 in series using the same set of electrodes.

In FIG. 9, the exemplary waveform protocol 900 includes the exemplary waveforms 130a, 130b and 130c. In the depicted example, the waveform protocol 900 comprises a cycling pattern of alternating waveforms including the waveforms 130c, 130b, 130a and 130a applied by the SCS IPG 106 in the depicted sequence. The waveform sequence of the waveform protocol 900 depicted in FIG. 9 repeats. The waveform sequence of the waveform protocol 900 may be configured to repeat using the SCS IPG 106 until a predetermined expiration time. The waveform protocol 900 may comprise any waveform configured by the SCS IPG 106. In the depicted example the individual waveforms of the exemplary waveform protocol 900 are applied by the SCS IPG 106 in series using the same set of electrodes.

Figure 10:
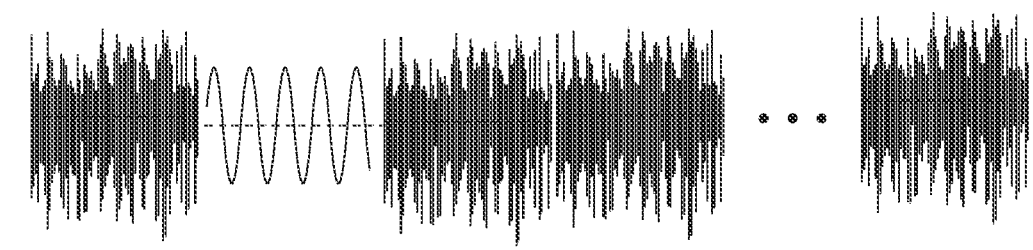
FIG. 10 depicts an example of running two exemplary waveform protocols in parallel using multiple electrode sets.

FIG. 10 depicts an example of running two exemplary waveform protocols in parallel using multiple electrode sets. In FIG. 10, the exemplary waveform protocol 1000 is applied by the SCS IPG 106 using one set of electrodes in electrical connection with one portion of the spinal cord of the patient. The exemplary waveform protocol 1005 is applied by the SCS IPG 106 using a different set of electrodes in electrical connection with a different portion of the spinal cord of the patient. The waveform protocols 1000 and 1005 are applied to the patient spinal cord at the same time in parallel using different sets of electrodes.

Figure 11:
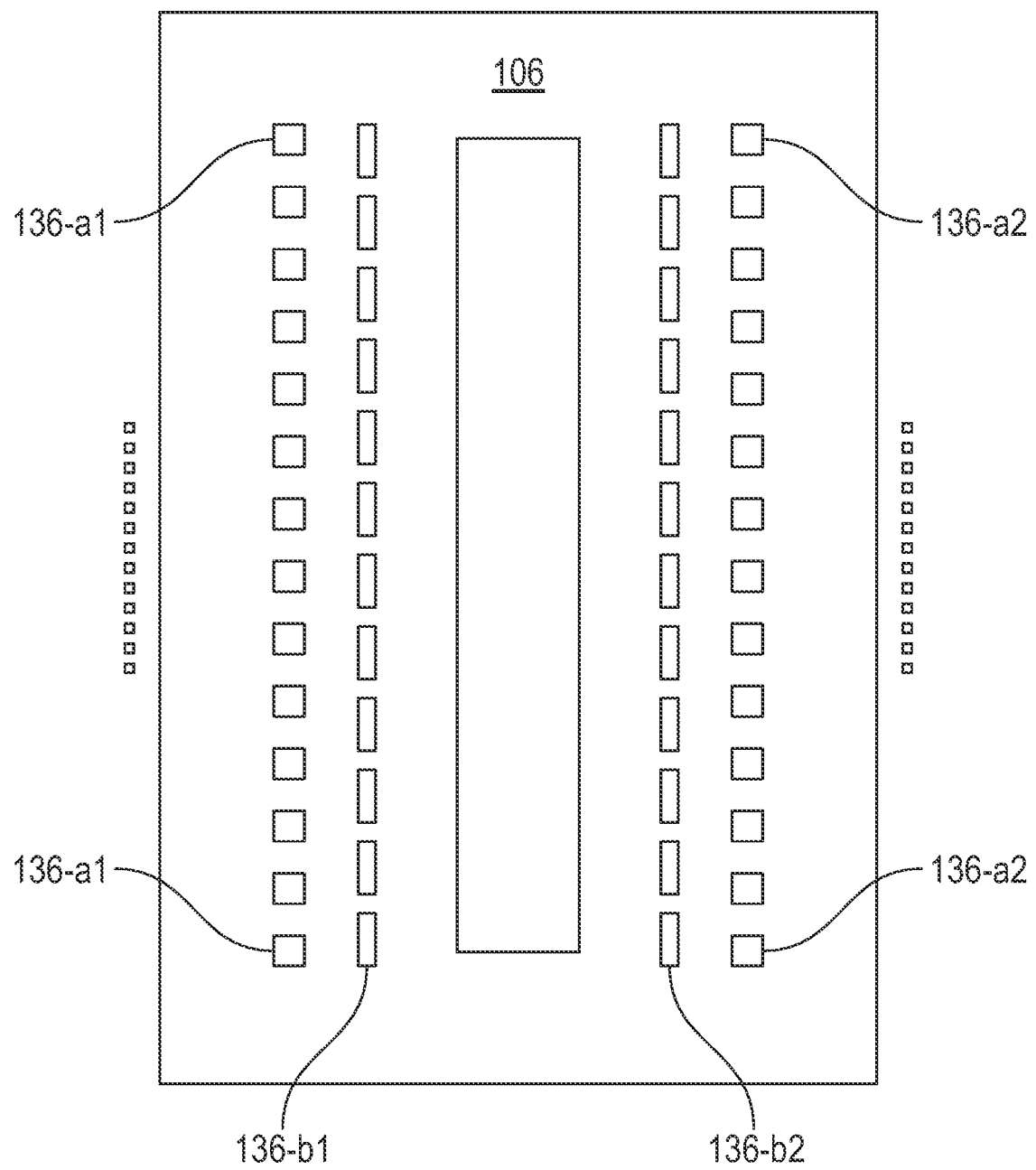
FIG. 11 depicts an exemplary IPG electrode input/output (I/O) interface configured to operate multiple electrode sets.

FIG. 11 depicts an exemplary IPG electrode input/output (I/O) interface configured to operate multiple electrode sets. The IPG electrode I/O interface depicted in FIG. 11 may be implemented in the electrode I/O interface 221 depicted in, at least, FIG. 2. FIG. 11 shows exemplary waveform energy output connections configured in groups 136-a1 and 136-a2, and exemplary waveform energy input connections configured in groups 136-b1 and 136-b2. The waveform energy input connections 136-a1 and 136-a2 may be configured by the SCS IPG 106 processor 200 in subgroups of one or more electrodes. The SCS IPG 106 processor 200 may configure one or more energy output connection from groups 136-a1 and 136-a2 to apply any waveform or group of waveforms in series or parallel. The SCS IPG 106 processor 200 may configure one or more energy input connections from groups 136-b1 and 136-b2 to measure applied waveform energy using one or more electrodes.

Figure 12:
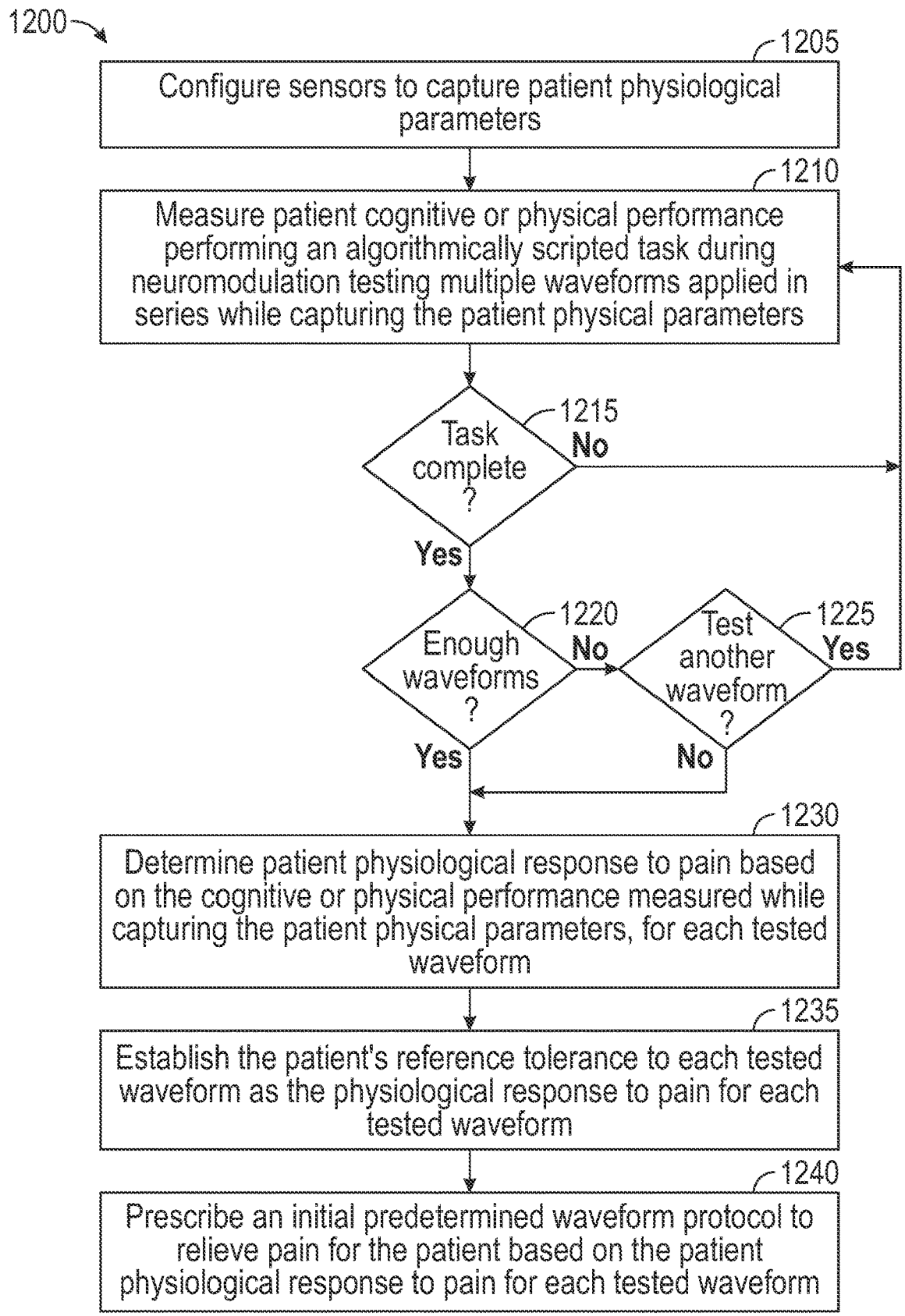
FIG. 12 depicts a process flow of an exemplary waveform protocol prescription engine (WPPE) establishing a reference pain syndrome tolerance to each waveform of a plurality of tested waveforms based on patient physiological or reported response to pain and measured patient task performance for each tested waveform in a trial phase.

FIG. 12 depicts a process flow of an exemplary waveform protocol prescription engine (WPPE) establishing a reference pain syndrome tolerance to each waveform of a plurality of tested waveforms based on patient physiological response to pain and measured patient task performance for each tested waveform in a trial phase.

The method 1200 depicted in FIG. 12 is given from the perspective of the WPPE 142 implemented via processor-executable program instructions executing on the SCS IPG 106 processor 200, depicted in FIG. 2. In the illustrated embodiment, the WPPE 142 executes as program instructions on the processor 200 configured in the WPPE 142 host SCS IPG 106, depicted in at least FIGS. 1A-B and FIG. 2. In some embodiments, the WPPE 142 may execute as a cloud service communicatively and operatively coupled with system services, hardware resources, or software elements local to and/or external to the SCS IPG 106.

The depicted method 1200 begins at step 1205 with the processor 200 configuring sensors to capture patient physiological parameters.

Then, the method continues at step 1210 with the processor 200 measuring patient cognitive or physical performance in an algorithmically scripted task during neuromodulation, testing multiple waveforms applied in series while capturing the patient physical parameters.

At step 1215 the processor 200 performs a test to determine if the algorithmically scripted task performed by the patient has been completed. Upon a determination by the processor 200 the algorithmically scripted task performed by the patient has been completed, the method continues at step 1220. Upon a determination by the processor 200 the algorithmically scripted task performed by the patient has not been completed, the method continues at step 1210.

At step 1220 the processor 200 performs a test to determine if enough waveforms have been tested in the trial phase. For example, the processor may compare the number of waveforms tested to a threshold number of waveforms to be tested. The threshold number of waveforms to be tested may be configured in a user interface, for example. Upon a determination by the processor 200 at step 1220 enough waveforms have been tested, the method continues at step 1230. Upon a determination by the processor 200 at step 1220 enough waveforms have not been tested, the method continues at step 1225.

At step 1225 the processor 200 performs a test to determine if another waveform is to be tested. Upon a determination by the processor 200 at step 1225 another waveform is to be tested the method continues at step 1210, otherwise the method continues at step 1230.

At step 1230 the processor 200 determines patient physiological response to pain and the cognitive or physical performance measured while capturing the patient physical parameters, for each tested waveform, and the method continues at step 1235.

At step 1235 the processor establishes a reference pain syndrome tolerance to each tested waveform based on patient physiological response to pain and the performance for each tested waveform, and the method continues at step 1240.

At step 1240 the processor 200 prescribes an initial waveform protocol to relieve pain for the patient based on the reference pain syndrome tolerance established for each tested waveform.

In some implementations the method may repeat.

Figure 13:
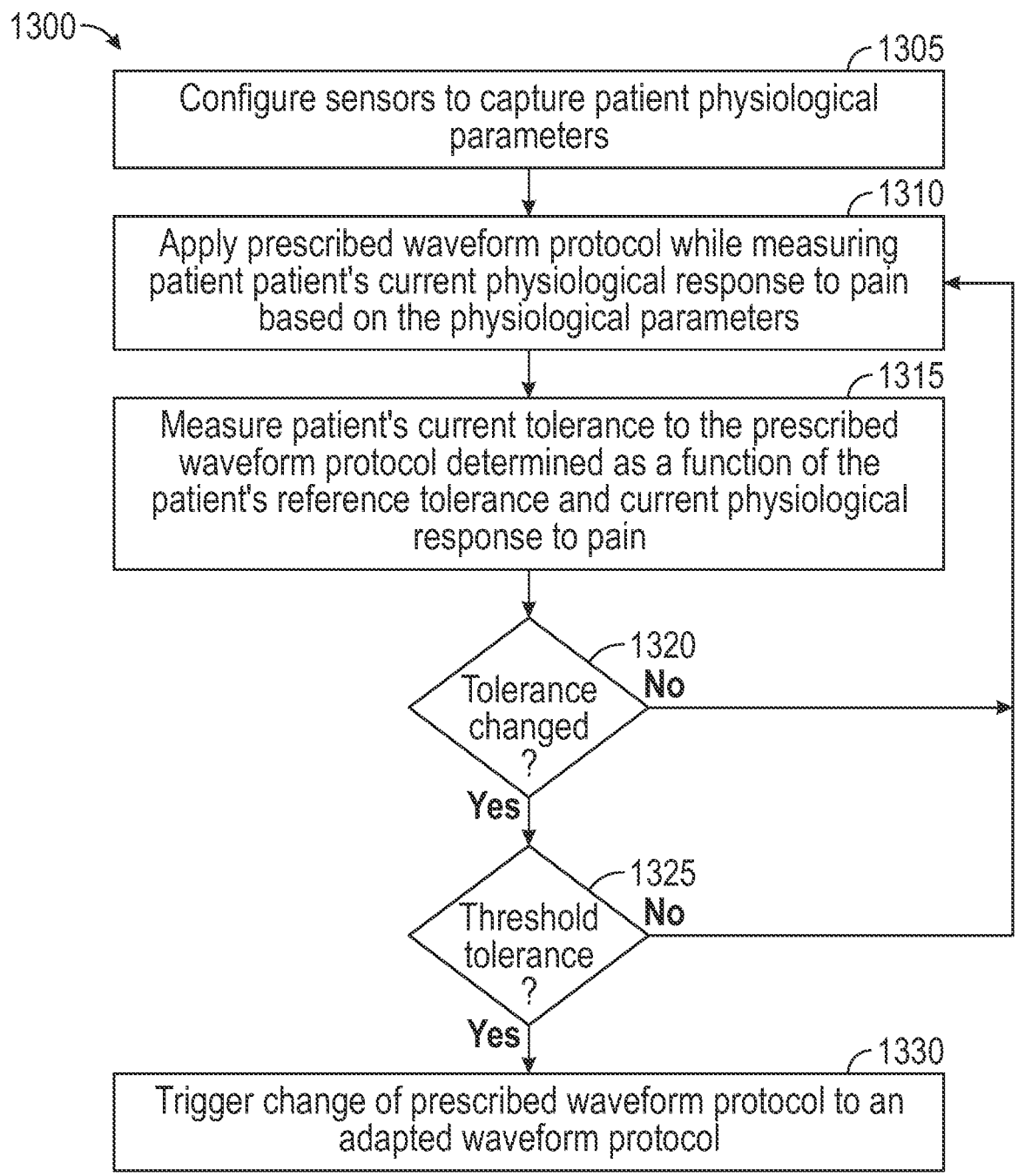
FIG. 13 depicts a process flow of an exemplary waveform protocol prescription engine applying a prescribed predetermined waveform protocol to a patient while measuring the patient's current physiological response to pain, measuring a current tolerance of the pain syndrome to the prescribed predetermined waveform protocol determined as a function of the patient's reference physiological response to pain established in a trial phase and the patient's current physiological response to pain, and in response to determining the tolerance of the pain syndrome to the prescribed predetermined waveform protocol changed by at least a predetermined minimum tolerance threshold difference, triggering a change of the prescribed predetermined waveform protocol to an adapted waveform protocol.

FIG. 13 depicts a process flow of an exemplary waveform protocol prescription engine applying a prescribed predetermined waveform protocol to a patient while measuring the patient's current physiological response to pain, measuring a current tolerance of the pain syndrome to the prescribed predetermined waveform protocol determined as a function of the patient's reference physiological response to pain established in a trial phase and the patient's current physiological response to pain, and in response to determining the tolerance of the pain syndrome to the prescribed predetermined waveform protocol changed by at least a predetermined minimum tolerance threshold difference, triggering a change of the prescribed predetermined waveform protocol to an adapted waveform protocol.

The method 1300 depicted in FIG. 13 is given from the perspective of the WPPE 142 implemented via processor-executable program instructions executing on the SCS IPG 106 processor 200, depicted in FIG. 2. In the illustrated embodiment, the WPPE 142 executes as program instructions on the processor 200 configured in the WPPE 142 host SCS IPG 106, depicted in at least FIGS. 1A-B and FIG. 2. In some embodiments, the WPPE 142 may execute as a cloud service communicatively and operatively coupled with system services, hardware resources, or software elements local to and/or external to the SCS IPG 106.

The depicted method 1300 begins at step 1305 with the processor 200 configuring sensors to capture patient physiological parameters.

Then, the method continues at step 1310 with the processor 200 applying a prescribed waveform protocol while measuring patient's current physiological response to pain based on physiological parameters captured by the sensors.

While measuring the patient's current physiological response to pain based on physiological parameters captured by the sensors at step 1315, the processor 200 measures the current tolerance of the pain syndrome to the prescribed waveform protocol determined as a function of the patient's reference physiological response and current physiological response.

At step 1320 the processor 200 performs a test to determine if the tolerance of the pain syndrome to the prescribed waveform protocol changed, based on comparing the patient's current physiological response to pain based on physiological parameters captured by the sensors at step 1315 with the patient's reference physiological response established during a trial phase. Upon a determination by the processor 200 at step 1320 the tolerance of the pain syndrome to the prescribed waveform protocol changed, the method continues at step 1325. Upon a determination by the processor 200 at step 1320 the tolerance of the pain syndrome to the prescribed waveform protocol did not change, the method continues at step 1310.

At step 1325 the processor 200 performs a test to determine if the pain syndrome tolerance change detected by the processor 200 at step 1320 satisfies at least a predetermined threshold difference. Upon a determination by the processor 200 at step 1325 the pain syndrome tolerance change satisfies at least the predetermined threshold difference, the method continues at step 1330, otherwise the method continues at step 1310.

At step 1330, the change in pain syndrome tolerance detected by the processor 200 triggers the processor 200 to change the prescribed waveform protocol to an adapted waveform protocol.

In some embodiments the method may repeat.

Figure 14:
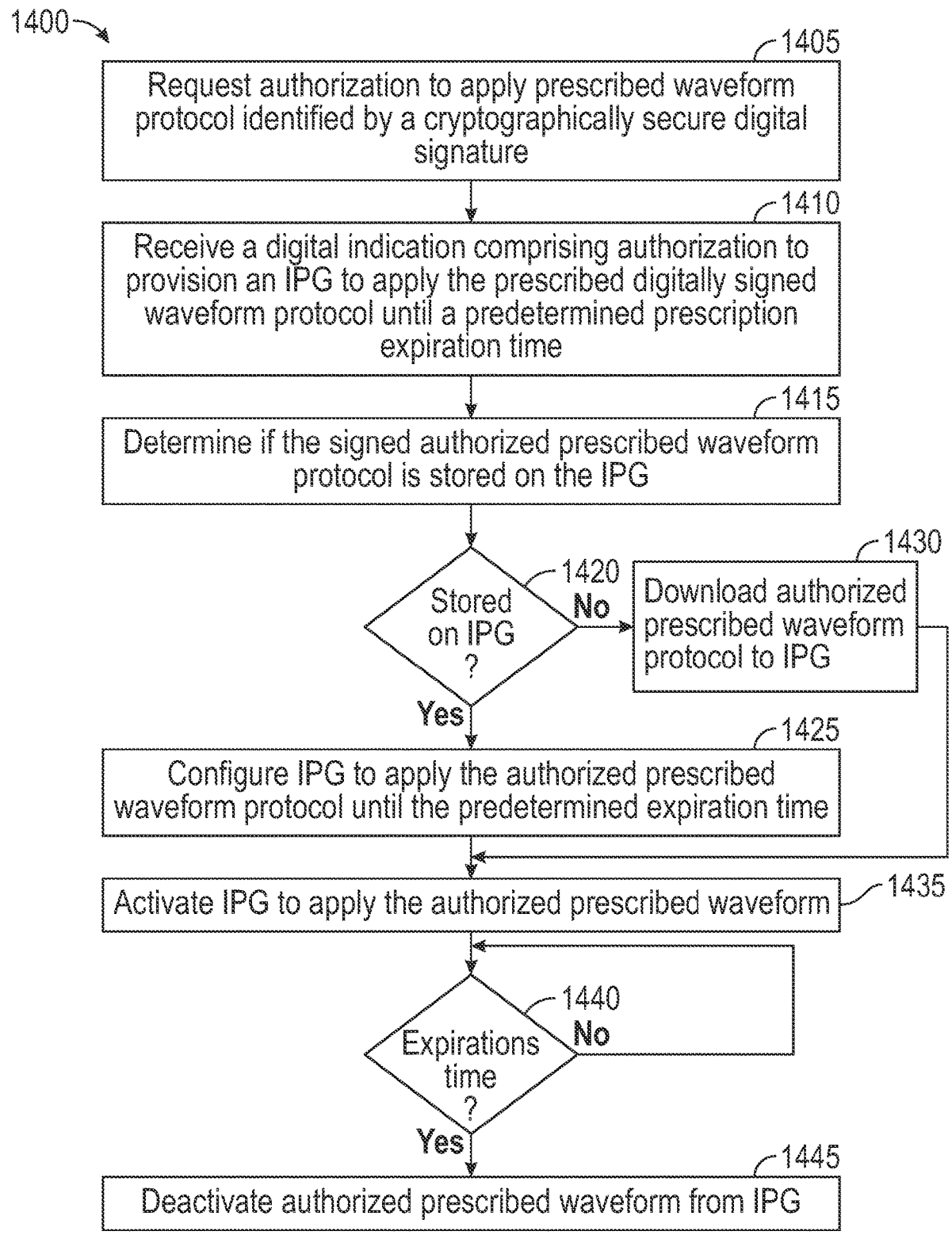
FIG. 14 depicts a process flow of an exemplary waveform protocol prescription engine executing an illustrative scenario obtaining authorization to apply a prescribed predetermined waveform protocol to a patient.

FIG. 14 depicts a process flow of an exemplary waveform protocol prescription engine executing an illustrative scenario obtaining authorization to apply a prescribed predetermined waveform protocol to a patient.

The method 1400 depicted in FIG. 14 is given from the perspective of the WPPE 142 implemented via processor-executable program instructions executing on the SCS IPG 106 processor 200, depicted in FIG. 2. In the illustrated embodiment, the WPPE 142 executes as program instructions on the processor 200 configured in the WPPE 142 host SCS IPG 106, depicted in at least FIGS. 1A-B and FIG. 2. In some embodiments, the WPPE 142 may execute as a cloud service communicatively and operatively coupled with system services, hardware resources, or software elements local to and/or external to the SCS IPG 106.

The depicted method 1400 begins at step 1405 with the processor 200 requesting authorization to apply a prescribed waveform protocol identified by a cryptographically secure digital signature. The processor 200 may request the authorization from a server configured to dispense authorizations for prescribing and applying predetermined or licensed waveforms. The processor 200 may request authorization to apply a waveform or waveform protocol selected in a user interface by a doctor. Then, the method continues at step 1410.

At step 1410 the processor 200 receives a digital indication comprising authorization to provision an IPG to apply the prescribed digitally signed waveform protocol until a predetermined prescription expiration time. Then, the method continues at step 1415.

At step 1415 the processor 200 determines if the signed authorized prescribed waveform protocol is stored on the IPG. Then, the method continues at step 1420.

At step 1420 the processor 200 performs a test based on the determination at step 1415, to determine if the signed authorized prescribed waveform protocol should be downloaded to the IPG. Upon a determination by the processor 200 at step 1420 the signed authorized prescribed waveform protocol is stored on the IPG, the method continues at step 1425. Upon a determination by the processor 200 at step 1420 the signed authorized prescribed waveform protocol is not stored on the IPG, the method continues at step 1430.

At step 1430 the processor 200 downloads the signed authorized prescribed waveform protocol to the IPG. Then, the method continues at step 1435.

At step 1425 the processor 200 configures the IPG to apply the authorized prescribed IPG waveform protocol until the predetermined expiration time. Then, the method continues at step 1435.

At step 1435 the processor 200 activates the IPG to apply the authorized prescribed waveform protocol. At step 1435 the processor may configure the IPG with the predetermined expiration time if the waveform was not previously stored on the IPG. Then the method continues at step 1440.

At step 1440 while applying the authorized prescribed waveform protocol the processor 200 performs a test to determine if the predetermined expiration time has been satisfied. Upon a determination by the processor 200 at step 1440 the predetermined expiration time has not been satisfied, the method continues at step 1440. Upon a determination by the processor 200 at step 1440 the predetermined expiration time has been satisfied, the method continues at step 1445.

At step 1445, the processor 200 deactivates the authorized prescribed waveform protocol from the IPG to stop applying the waveform protocol to the patient.

In some embodiments the method may repeat.

Figure 15:
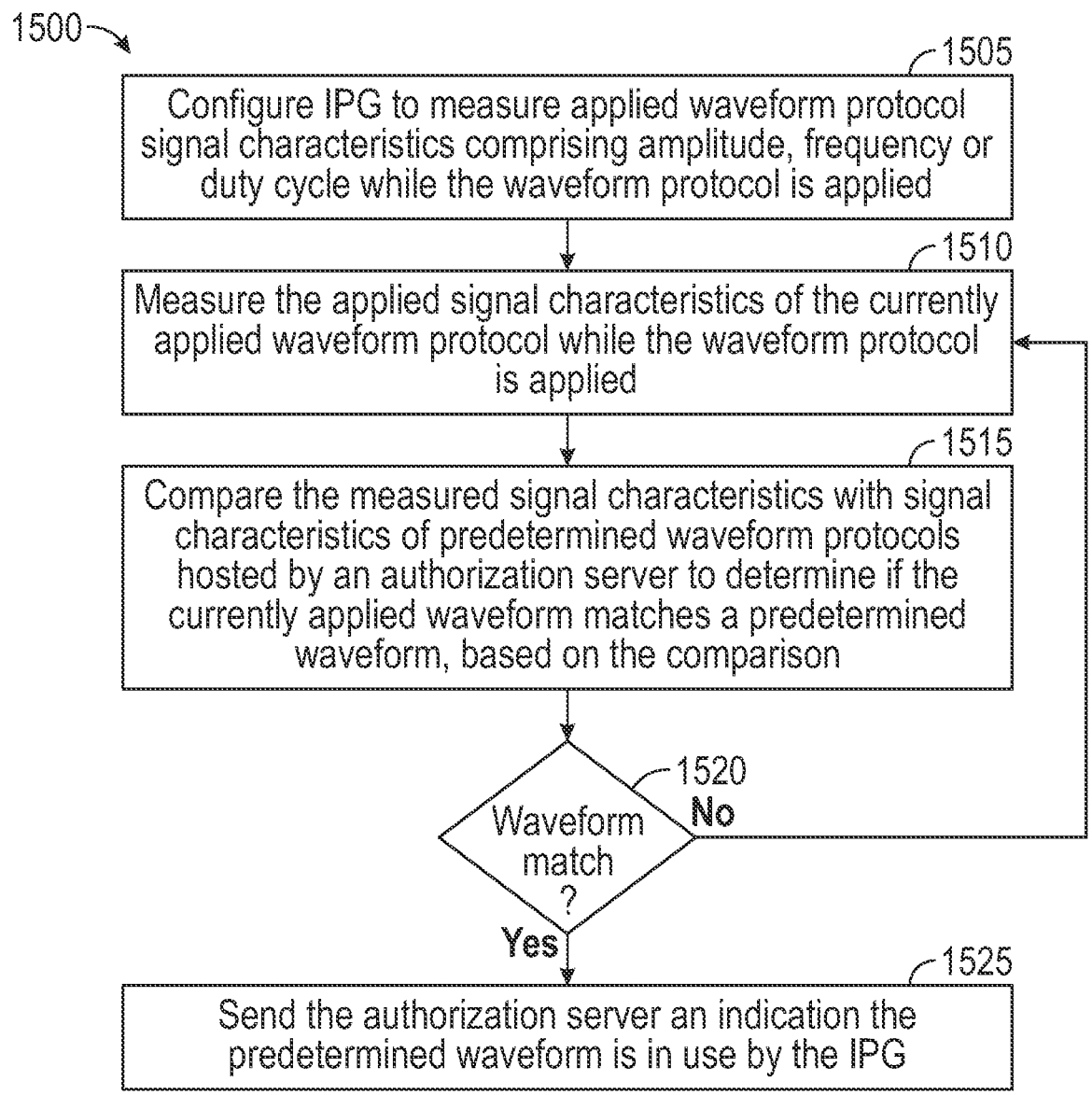
FIG. 15 depicts a process flow of an exemplary waveform protocol prescription engine executing an illustrative scenario detecting use of a predetermined waveform protocol based on measured signal characteristics.

FIG. 15 depicts a process flow of an exemplary waveform protocol prescription engine executing an illustrative scenario detecting use of a predetermined waveform protocol based on measured signal characteristics.

The method 1500 depicted in FIG. 15 is given from the perspective of the WPPE 142 implemented via processor-executable program instructions executing on the SCS IPG 106 processor 200, depicted in FIG. 2. In the illustrated embodiment, the WPPE 142 executes as program instructions on the processor 200 configured in the WPPE 142 host SCS IPG 106, depicted in at least FIGS. 1A-B and FIG. 2. In some embodiments, the WPPE 142 may execute as a cloud service communicatively and operatively coupled with system services, hardware resources, or software elements local to and/or external to the SCS IPG 106.

The depicted method 1500 begins at step 1505 with the processor 200 configuring the IPG to measure applied waveform protocol signal characteristics comprising amplitude, frequency or duty cycle while the waveform protocol is applied. Then, the method continues at step 1510.

At step 1510 the processor 200 measures the applied signal characteristics of the currently applied waveform protocol while the waveform protocol is applied. Then, the method continues at step 1515.

At step 1515 the processor 200 compares the measured signal characteristics with signal characteristics of predetermined waveform protocols hosted by an authorization server to determine if the currently applied waveform matches a predetermined waveform, based on the comparison. Then, the method continues at step 1520.

At step 1520 the processor 200 performs a test to determine if the processor 200 should send an indication a predetermined waveform or waveform protocol is in use by the IPG, based on the comparison performed by the processor 200 at step 1515.

At step 1525, upon a determination by the processor 200 at step 1520 the processor 200 should send an indication a predetermined waveform is in use by the IPG, the processor 200 sends the authorization server an indication the predetermined waveform is in use by the IPG. An SCS IPG implementation configured to detect a predetermined waveform or waveform protocol in use may be able to prevent the non-permissive/unauthorized usage of proprietary waveforms.

In some embodiments the method may repeat.

Figure 16:
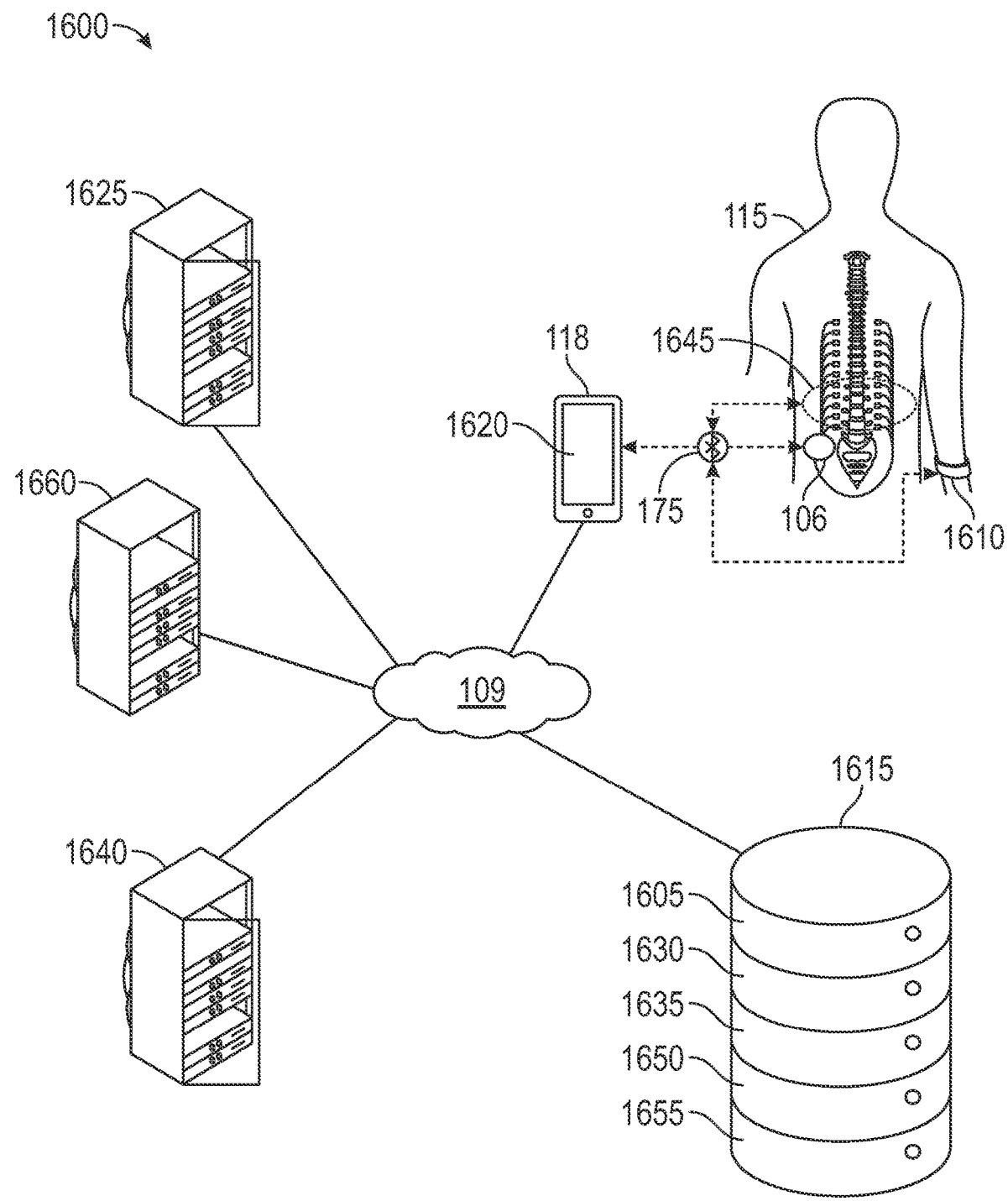

FIG. 16 depicts an exemplary neuromodulation waveform watermarking and prescribing system configured to collect signal data sampled using an input electrode contacting a patient while a neuromodulation device (NMD) applies a neuromodulation waveform using an output electrode contacting the patient, identify signal characteristics of the applied neuromodulation waveform determined as a function of the collected signal data, and generate a notification if the applied neuromodulation waveform matches any known predetermined neuromodulation waveform, based on the identified signal characteristics.

In FIG. 16 the exemplary neuromodulation waveform watermarking and prescribing system 1600 is configured to treat a pain syndrome in patient 115. A doctor may prescribe one or more prescription neuromodulation waveforms 1605 to treat the pain syndrome. The prescription neuromodulation waveforms 1605 may be applied to the patient 115 by a neuromodulation device (NMD). The NMD may be the implantable pulse generator (IPG) 106. The IPG 106 may be implanted into the patient 115. The NMD may be the wearable pulse generator (WPG) 1610. The WPG 1610 is configured in a patient-wearable device with circuitry and software substantially the same as the implantable IPG 106. The prescription neuromodulation waveforms 1605 may be applied to the patient 115 by the WPG 1610. The prescription neuromodulation waveforms 1605 may be loaded from the data store 1615 into the IPG 106 or the WPG 1610.

In the depicted implementation, the mobile device 118 is operably coupled with the network cloud 109. The mobile device 118 may be configured with a mobile app 1620. The mobile app 1620 may be configured to permit the doctor to prescribe the one or more prescription neuromodulation waveforms 1605. The mobile app 1620 may be configured to permit a clinical expert to program and configure the NMD. The mobile app 1620 may be configured to permit the patient 115 to manage treatment by the NMD. In the depicted implementation, the waveform prescription deployment server 1625 is operably coupled with the network cloud 109, The waveform prescription deployment server 1625 may activate the IPG 106 or the WPG 1610 to apply the one or more prescription neuromodulation waveforms 1605 to the patient 115.

The IPG 106 or the WPG 1610 may be configured to sample energy from one or more waveforms applied to the patient 115. The IPG 106 or the WPG 1610 may sample energy from the one or more waveforms while the one or more waveforms are applied to the patient 115. The IPG 106 or the WPG 1610 may sample energy from the one or more waveforms by sampling the waveform energy with a processor configured in the IPG 106 or the WPG 1610. The processor configured in the IPG 106 or the WPG 1610 may sample the waveform energy through input electrodes in electrical communication with the spinal cord of the patient 115.

The one or more waveforms applied to the patient 115 may be one or more prescription neuromodulation waveforms 1605. The one or more prescription neuromodulation waveforms 1605 may be known predetermined waveforms. The IPG 106 or the WPG 1610 may compare measured waveform signal parameters or characteristics to waveform signal parameters 1630 of known predetermined waveforms to determine if any known predetermined waveform is in use by the IPG 106 or WPG 1610. The IPG 106 or WPG 1610 may use one or more digital signal processing (DSP) algorithms 1635 to analyze the measured waveform signal parameters 1630, to determine if any known predetermined waveform is in use by the IPG 106 or WPG 1610.

The IPG 106 or WPG 1610 may be configured to sample and collect the waveform signals and apply the DSP algorithms 1635 to the waveform signal samples. In the depicted implementation, the waveform identification server 1640 is operably coupled with the network cloud 109. The IPG 106 or WPG 1610 may be configured to sample and collect the waveform signals and send the samples or detected signal parameters or characteristics to the waveform identification server 1640. The waveform identification server 1640 may apply one or more DSP algorithms 1635 to the waveform signal samples or detected signal parameters or characteristics received by the waveform identification server 1640 from the IPG 106 or WPG 1610. In the depicted implementation, the IPG 106, the WPG 1610 and the discrete collection device 1645 are operably coupled with the mobile device 118 via the communication link 175. The IPG 106, the WPG 1610 and/or the discrete collection device 1645 may be operably coupled with the network cloud 109 via one or more communication link. The discrete collection device is configured to collect sampled waveform data without capability to apply waveform energy to a patient. The discrete collection device 1645 is described in more detail with reference to FIG. 19. In the depicted implementation, the communication link 175 is a BLUETOOTH link. The communication link 175 may be any type of communication link. The discrete collection device 1645 may sample and collect the waveform signals. The discrete collection device 1645 may send signal samples to the mobile device 118 or the waveform identification server 1640 for analysis or waveform identification.

The IPG 106 or WPG 1610 may be configured to add at least one identifying signal to a waveform being applied to the patient 115. The identifying signal may be a digital watermark. The digital watermark may be for example, a binary sequence encoded in a waveform being applied to the patient 115. The IPG 106 and the WPG 1610 may be configured to use at least one watermark embedding algorithm 1650 to embed or encode waveform identifying data in one or more prescription neuromodulation waveforms 1605. The IPG 106, the WPG 1610 and/or the waveform identification server 1640 may be configured to use one or more watermark detection algorithm 1655 to extract or decode identifying data including watermark data embedded or encoded in one or more prescription neuromodulation waveforms 1605.

In the depicted implementation, the waveform prescription authorization server 1660 is operably coupled with the network cloud 109. The waveform prescription authorization server 1660 includes a processor, a network communication interface and a memory retaining processor executable program instructions configured that when executed by the processor, the program instructions cause the waveform prescription authorization server 1660 to perform operations. In the implementation depicted by FIG. 16, the waveform prescription authorization server 1660 is configured with a database comprising prescription neuromodulation waveforms, a patient 115 population and an indication in the database of which prescription neuromodulation waveforms are approved for use by each patient 115 in the patient 115 population. Approval by the waveform prescription authorization server 1660 may be determined using the database, based on medical need or insurance coverage to use a particular prescription neuromodulation waveform. A waveform prescription authorization server 1660 implementation may be configured to receive a request for an approval for the patient 115 to use a particular prescription waveform, determine if the particular prescription waveform is listed in the database as approved for the patient 115 and respond with an approval or denial, depending on the determination. In an illustrative example the waveform prescription authorization server 1660 may be configured for receiving requests from the prescription deployment server 1625 to approve the NMD to use or continue using prescription neuromodulation waveforms; determining if the request is approved, based on health plan coverage for the prescription and returning a decision to the prescription deployment server 1625. The prescription deployment server 1625 may forward the decision to the NMD or the device associated with the NMD. If the request is approved, the prescription deployment server 1625 may send a prescription activation data package to the NMD or the computing device associated with the NMD. An implementation of the waveform prescription authorization server 1660 may be hosted by the waveform prescription deployment server 1625 when joining authorization decisions and medical decisions would be advantageous. An implementation of the waveform prescription authorization server 1660 may be hosted on a separate computing platform (that is, using a separate memory address space accessed by separate processors and a different network interface) from the waveform prescription deployment server 1625, to divide authorization decisions from medical decisions. An exemplary neuromodulation waveform watermarking and prescribing system 1600 may be implemented using virtual private network (VPN) configurations to restrict the NMD or the computing device associated with the NMD from communicating directly with the waveform prescription authorization server 1660. In such an implementation the waveform prescription authorization server 1660 and waveform prescription deployment server 1625 may be connected via a VPN with distinct security credentials not shared with the NMD or the computing device associated with the NMD. Both the waveform prescription authorization server 1660 and waveform prescription deployment server 1625 may be multi-homed, with at least one network interface configured in the VPN and one interface not configured in the VPN. In some implementations the waveform prescription deployment server 1625 may host a VPN configured with security credentials derived from a shared secret key generated by the waveform prescription deployment server 1625 during an NMD registration phase. In such an implementation the NMD or the computing device associated with the NMD may join the VPN hosted by the waveform prescription deployment server 1625, based on the shared secret, however the waveform prescription authorization server 1660 would not have the shared secret and would be restricted from joining this VPN.

Figure 17:
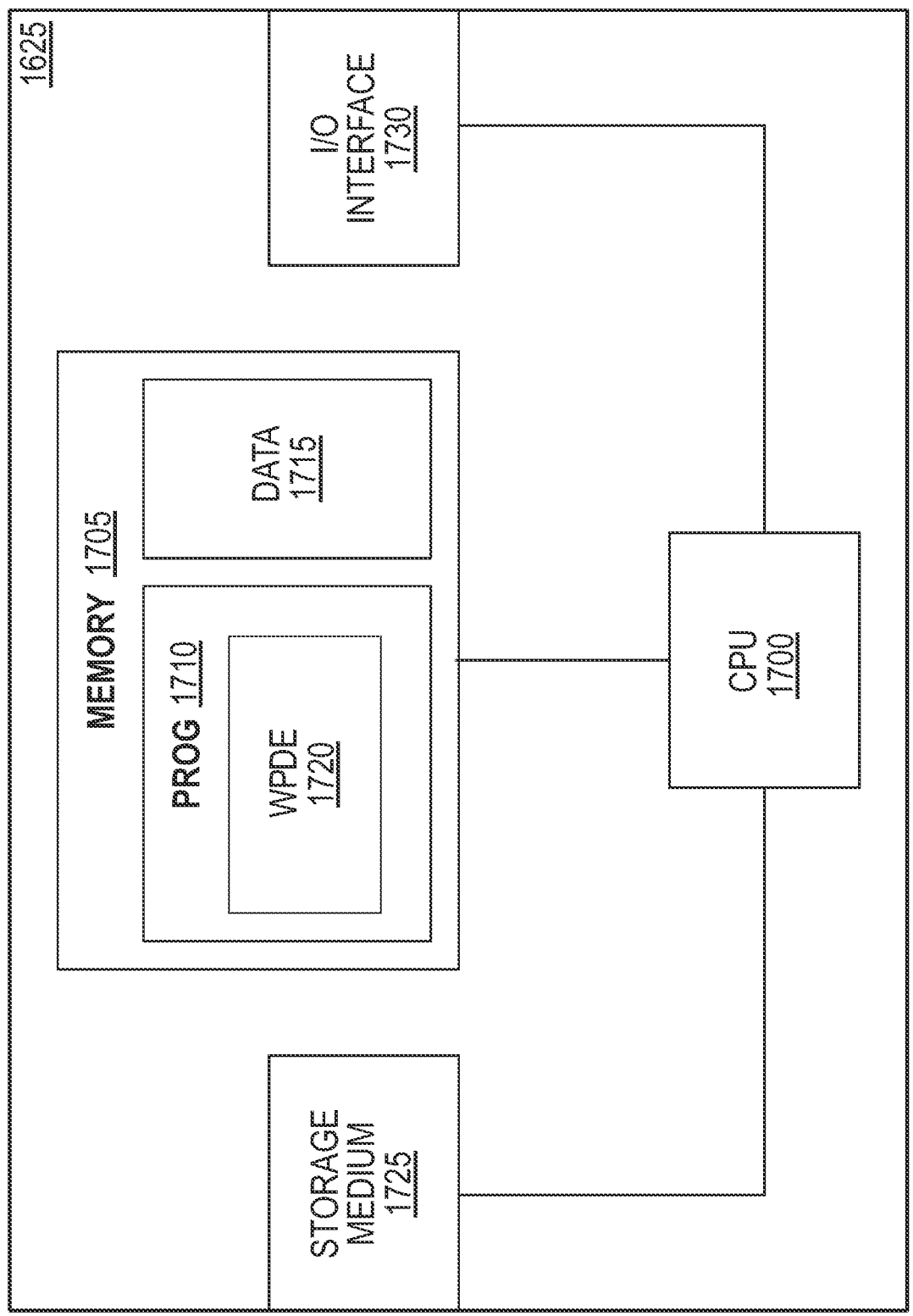

FIG. 17 depicts a structural block diagram of an exemplary waveform prescription deployment server configured to receive a digital prescription to apply a prescribed neuromodulation waveform to a patient using a neuromodulation device, request biometric patient authentication by a computing device associated with the neuromodulation device and in response to receiving an indication of successful patient authentication, activating the neuromodulation device to apply the prescribed neuromodulation waveform to the patient, based on sending to the neuromodulation device a time-based one-time-password generated from a shared secret key distributed during a registration phase.

In the implementation depicted by FIG. 17, the exemplary waveform prescription deployment server 1625 includes the CPU (processor) 1700 and the memory 1705. In the depicted implementation, the processor 1700 is in electrical communication with the memory 1705. The processor 1700 may be operably coupled with one or more memory 1705 via a communication network. In the depicted implementation, the memory 1705 includes the program memory 1710 and the data memory 1715. The depicted program memory 1710 includes processor-executable program instructions implementing the waveform prescription deployment engine (WPDE) 1720. The illustrated program memory 1710 may include processor-executable program instructions configured to implement an OS (Operating System). In various embodiments, the OS may include processor executable program instructions configured to implement various operations when executed by the processor 1700. The OS may be omitted. The illustrated program memory 1710 may include processor-executable program instructions configured to implement various Application Software. The Application Software may include processor executable program instructions configured to implement various operations when executed by the processor 1700. The Application Software may be omitted.

In the depicted embodiment, the processor 1700 is communicatively and operably coupled with the storage medium 1725. The storage medium 1725 may be configured to implement various data storage and data retrieval operations for the processor 1700 such as for example, read/write, read/only or non-volatile storage and retrieval. In the depicted embodiment, the processor 1700 is communicatively and operably coupled with the I/O (Input/Output) interface 1730. In the depicted embodiment, the I/O interface 1730 includes a network communication interface. In various implementations, the network communication interface may be a wireless network interface. In some designs, the network interface may be a Wi-Fi interface. In some embodiments, the network interface may be a BLUETOOTH interface. In an illustrative example, the waveform prescription deployment server 1625 may include more than one network interface. The network interface may be a wireline interface. The network interface may be omitted.

The depicted memory 1705 may contain processor executable program instruction modules and data configurable by the processor 1700 to be adapted to provide neuromodulation waveform signal input capability, neuromodulation waveform signal output capability, neuromodulation waveform sampling, digital signal processing (DSP) algorithms, spectral waveform analysis, correlation, autocorrelation, Fourier transforms, sample buffering, modulation, demodulation, error correction, encryption, decryption, encryption key generation, encryption key management, biometric template generation, biometric input authentication, waveform signal filtering operations including adjusting frequency response and attenuation characteristics of temporal domain and frequency domain filters, waveform pattern recognition, waveform template matching, waveform artifact template generation, waveform artifact template matching, and/or anomaly detection.

Useful examples of the illustrated waveform prescription deployment server 1625 may include, but are not limited to, personal computers, servers, tablet PCs, smartphones, or other computing devices. In some embodiments, multiple waveform prescription deployment server 1625 devices may be operably linked to form a computer network in a manner as to distribute and share one or more resources, such as clustered computing devices and server banks/farms. In some embodiments, an exemplary waveform prescription deployment server 1625 design may be realized in a distributed implementation. A waveform prescription deployment server 1625 design may be partitioned between a client device, such as, for example, a phone, and a more powerful server system with greater resources, such as for example, computation, memory or storage capacity. In various designs, a waveform prescription deployment server 1625 partition hosted on a PC or mobile device may choose to delegate some parts of computation, such as, for example, machine learning or deep learning, to a host server. In some embodiments, a client device partition may delegate computation-intensive tasks to a host server to take advantage of a more powerful processor, or to offload excess work.

In an illustrative example, some devices may be configured with a mobile chip including an engine adapted to implement specialized processing, such as, for example, neural networks, machine learning, artificial intelligence, image recognition, audio processing, or digital signal processing. In some embodiments, such an engine adapted to specialized processing may have sufficient processing power to implement some features. However, in some embodiments, an exemplary waveform prescription deployment server 1625 may be configured to operate on a device with less processing power, such as, for example, various gaming consoles, which may not have sufficient processor power, or a suitable CPU architecture, to adequately support waveform prescription deployment server 1625. Various embodiment designs configured to operate on such a device with reduced processor power may work in conjunction with a more powerful server system.

Figure 18:
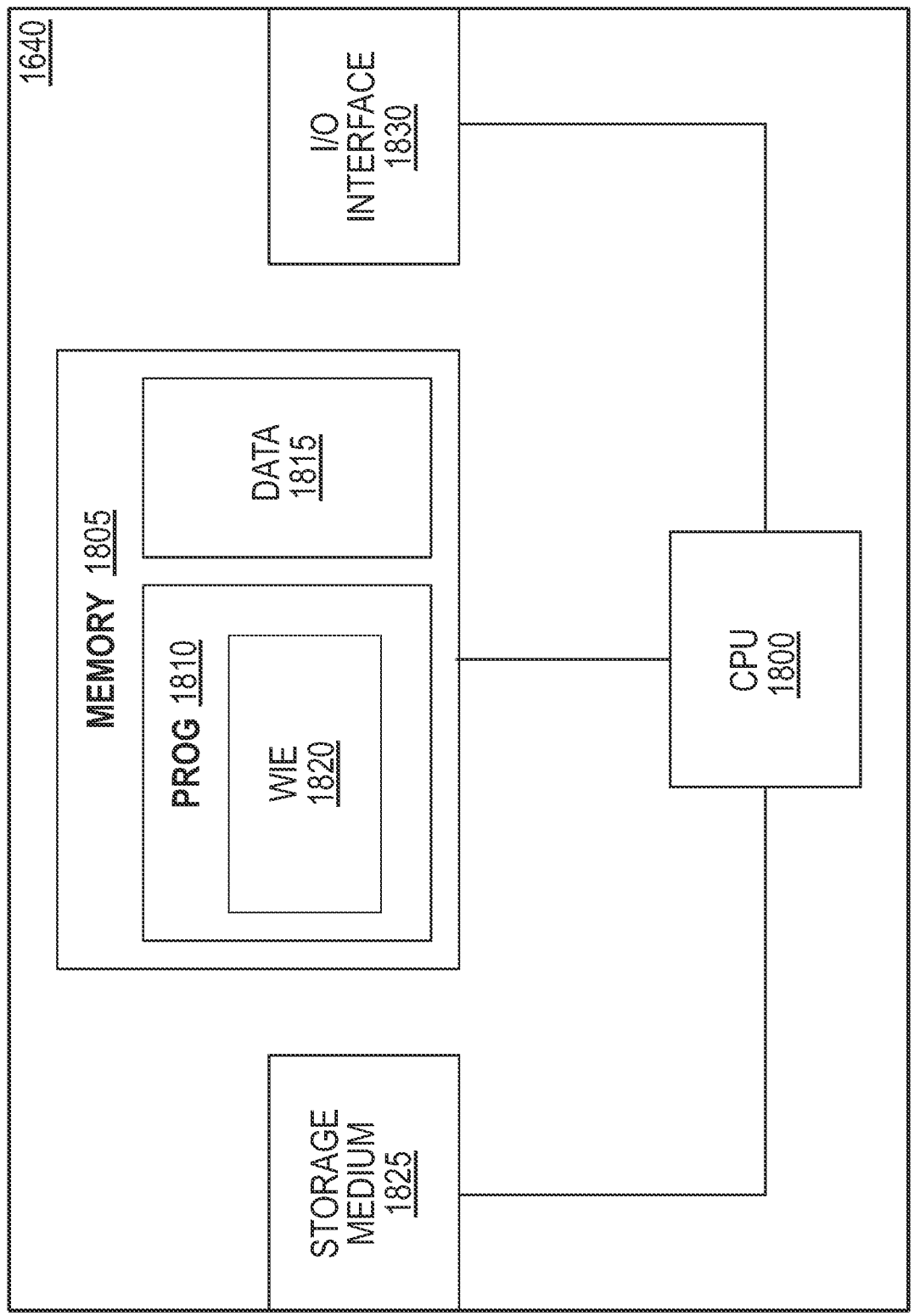

FIG. 18 depicts a structural block diagram of an exemplary waveform identification server configured to receive collected signal data, identify signal characteristics or an embedded watermark in an applied neuromodulation waveform determined as a function of the collected signal data, and generate a notification if the applied neuromodulation waveform or watermark matches any known predetermined neuromodulation waveform or watermark, based on the identified signal characteristics.

In the implementation depicted by FIG. 18, the exemplary waveform identification server 1640 includes the CPU (processor) 1800 and the memory 1805. In the depicted implementation, the processor 1800 is in electrical communication with the memory 1805. The processor 1800 may be operably coupled with one or more memory 1805 via a communication network. In the depicted implementation, the memory 1805 includes the program memory 1810 and the data memory 1815. The depicted program memory 1810 includes processor-executable program instructions implementing the waveform identification engine (WIE) 1820. The illustrated program memory 1810 may include processor-executable program instructions configured to implement an OS (Operating System). In various embodiments, the OS may include processor executable program instructions configured to implement various operations when executed by the processor 1800. The OS may be omitted. The illustrated program memory 1810 may include processor-executable program instructions configured to implement various Application Software. The Application Software may include processor executable program instructions configured to implement various operations when executed by the processor 1800. The Application Software may be omitted.

In the depicted embodiment, the processor 1800 is communicatively and operably coupled with the storage medium 1825. The storage medium 1825 may be configured to implement various data storage and data retrieval operations for the processor 1800 such as for example, read/write, read/only or non-volatile storage and retrieval. In the depicted embodiment, the processor 1800 is communicatively and operably coupled with the I/O (Input/Output) interface 1830. In the depicted embodiment, the I/O interface 1830 includes a network communication interface. In various implementations, the network communication interface may be a wireless network interface. In some designs, the network interface may be a Wi-Fi interface. In some embodiments, the network interface may be a BLUETOOTH interface. In an illustrative example, the waveform identification server 1640 may include more than one network interface. The network interface may be a wireline interface. The network interface may be omitted.

The depicted memory 1805 may contain processor executable program instruction modules and data configurable by the processor 1800 to be adapted to provide neuromodulation waveform signal input capability, neuromodulation waveform signal output capability, neuromodulation waveform sampling, digital signal processing (DSP) algorithms, spectral waveform analysis, correlation, autocorrelation, Fourier transforms, sample buffering, modulation, demodulation, error correction, encryption, decryption, encryption key generation, encryption key management, biometric template generation, biometric input authentication, waveform signal filtering operations including adjusting frequency response and attenuation characteristics of temporal domain and frequency domain filters, waveform pattern recognition, waveform template matching, waveform artifact template generation, waveform artifact template matching, and/or anomaly detection.

Useful examples of the illustrated waveform identification server 1640 may include, but are not limited to, personal computers, servers, tablet PCs, smartphones, or other computing devices. In some embodiments, multiple waveform identification server 1640 devices may be operably linked to form a computer network in a manner as to distribute and share one or more resources, such as clustered computing devices and server banks/farms. In some embodiments, an exemplary waveform identification server 1640 design may be realized in a distributed implementation. A waveform identification server 1640 design may be partitioned between a client device, such as, for example, a phone, and a more powerful server system with greater resources, such as for example, computation, memory or storage capacity. In various designs, a waveform identification server 1640 partition hosted on a PC or mobile device may choose to delegate some parts of computation, such as, for example, machine learning or deep learning, to a host server. In some embodiments, a client device partition may delegate computation-intensive tasks to a host server to take advantage of a more powerful processor, or to offload excess work.

In an illustrative example, some devices may be configured with a mobile chip including an engine adapted to implement specialized processing, such as, for example, neural networks, machine learning, artificial intelligence, image recognition, audio processing, or digital signal processing. In some embodiments, such an engine adapted to specialized processing may have sufficient processing power to implement some features. However, in some embodiments, an exemplary waveform identification server 1640 may be configured to operate on a device with less processing power, such as, for example, various gaming consoles, which may not have sufficient processor power, or a suitable CPU architecture, to adequately support waveform identification server 1640. Various embodiment designs configured to operate on such a device with reduced processor power may work in conjunction with a more powerful server system.

Figure 19:
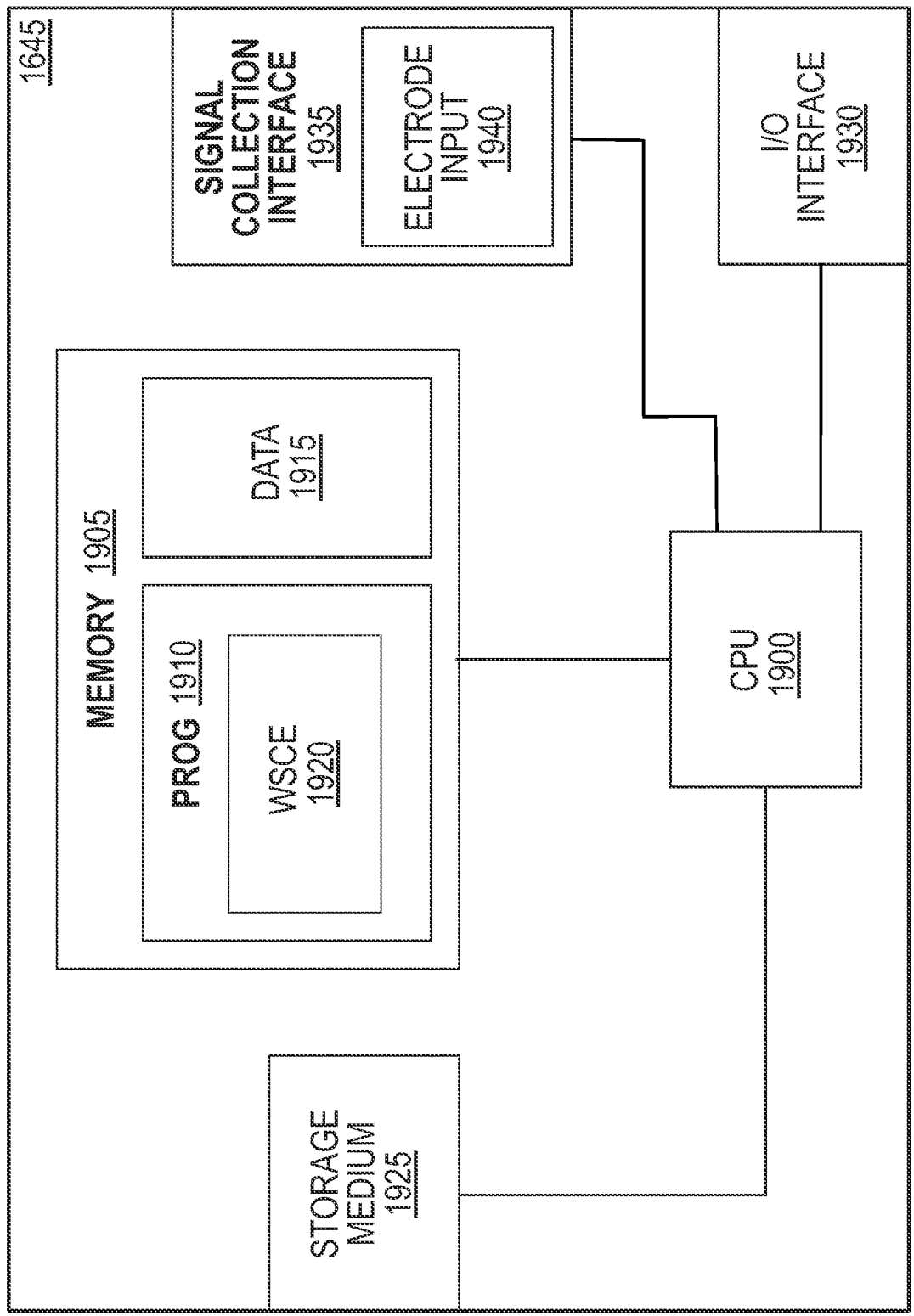

FIG. 19 depicts a structural block diagram of an exemplary discrete collection device configured to collect signal data sampled using an input electrode contacting a patient while a separate neuromodulation device (NMD) applies a neuromodulation waveform using an output electrode contacting the patient.

In the implementation depicted by FIG. 19, the discrete collection device 1645 includes the CPU (processor) 1900 and the memory 1905. In the depicted implementation, the processor 1900 is in electrical communication with the memory 1905. The processor 1900 may be operably coupled with one or more memory 1905 via a communication network. In the depicted implementation, the memory 1905 includes the program memory 1910 and the data memory 1915. The depicted program memory 1910 includes processor-executable program instructions implementing the waveform signal collection engine (WSCE) 1920. The WSCE 1920 governs discrete collection device 1645 operations comprising sampling waveform energy using input electrodes in contact with a patient body, collecting the samples, and forwarding the collected samples to a waveform identification server or a computing device associated with an NMD. The illustrated program memory 1910 may include processor-executable program instructions configured to implement an OS (Operating System). In various embodiments, the OS may include processor executable program instructions configured to implement various operations when executed by the processor 1900. The OS may be omitted. The illustrated program memory 1910 may include processor-executable program instructions configured to implement various Application Software. The Application Software may include processor executable program instructions configured to implement various operations when executed by the processor 1900. The Application Software may be omitted.

In the depicted embodiment, the processor 1900 is communicatively and operably coupled with the storage medium 1925. The storage medium 1925 may be configured to implement various data storage and data retrieval operations for the processor 1900 such as for example, read/write, read/only or non-volatile storage and retrieval. In the depicted embodiment, the processor 1900 is communicatively and operably coupled with the I/O (Input/Output) interface 1930. In the depicted embodiment, the I/O interface 1930 includes a network communication interface. In various implementations, the network communication interface may be a wireless network interface. In some designs, the network interface may be a Wi-Fi interface. In some embodiments, the network interface may be a BLUETOOTH interface. In an illustrative example, the discrete collection device 1645 may include more than one network interface. The network interface may be a wireline interface. The network interface may be omitted.

In the depicted embodiment, the processor 1900 is communicatively and operably coupled with the signal collection interface 1935. In the depicted implementation, the signal collection interface 1935 includes the electrode input interface 1940. The signal collection interface 1935 may be configured by the processor 1900 to implement various signal collection operations for the processor 1900 such as for example, sampling neuromodulation waveform signals using one or more electrode in electrical communication with the electrode input interface 1940. The one or more electrode in electrical communication with the electrode input interface 1940 may be a sense electrode. The signal collection interface 1935 may be configured to receive input energy from the one or more electrode. The one or more electrodes may be configured to be in contact with a patient body to receive electrical input energy from the patient body. The electrical input energy from the one or more electrodes may be used by the processor 1900 to measure energy applied to the patient by a neuromodulation device. The electrical input energy from the one or more electrodes may be used by the processor 1900 to measure energy originating from the patient body such as for example, an electrically evoked compound action potential (ECAP).

The signal collection interface 1935 may include an analog-to-digital converter configured to convert electrical input energy from one or more sense electrode connected to the electrode input interface 1940 into digital form for use by the processor 1900. The analog-to-digital converter resolution and sampling rate may be configurable by the processor 1900. The signal collection interface 1935 may include one or more filters configurable by the processor 1900 to selectively remove and/or pass certain frequencies from the input energy. For example, the signal collection interface may include a low pass filter configurable by the processor as an anti-aliasing filter. For example, the anti-aliasing filter may have a pass band configurable by the processor 1900 to reject input frequencies above half the sampling rate of the analog-to-digital converter. The signal collection interface 1935 may include impedance matching circuitry. The impedance matching circuitry may be configurable by the processor 1900 to match electrode input impedance with the impedance of the patient's body. Matching electrode input impedance with the impedance of the patient's body may permit efficiently receiving signal energy from a waveform applied to the patient's body, achieving more accurate measurement as a result of mitigating signal loss that might result from impedance mismatch.

The depicted memory 1905 may contain processor executable program instruction modules and data configurable by the processor 1900 to be adapted to provide neuromodulation waveform signal input capability, neuromodulation waveform signal output capability, neuromodulation waveform sampling, digital signal processing (DSP) algorithms, spectral waveform analysis, correlation, autocorrelation, Fourier transforms, sample buffering, modulation, demodulation, error correction, encryption, decryption, encryption key generation, encryption key management, biometric template generation, biometric input authentication, waveform signal filtering operations including adjusting frequency response and attenuation characteristics of temporal domain and frequency domain filters, waveform pattern recognition, waveform template matching, waveform artifact template generation, waveform artifact template matching, and/or anomaly detection.

Useful examples of the illustrated discrete collection device 1645 may include, but are not limited to, personal computers, servers, tablet PCs, smartphones, or other computing devices. In some embodiments, multiple discrete collection device 1645 devices may be operably linked to form a computer network in a manner as to distribute and share one or more resources, such as clustered computing devices and server banks/farms. In some embodiments, an exemplary discrete collection device 1645 design may be realized in a distributed implementation. A discrete collection device 1645 design may be partitioned between a client device, such as, for example, a phone, and a more powerful server system with greater resources, such as for example, computation, memory or storage capacity. In various designs, a discrete collection device 1645 partition hosted on a PC or mobile device may choose to delegate some parts of computation, such as, for example, machine learning or deep learning, to a host server. In some embodiments, a client device partition may delegate computation-intensive tasks to a host server to take advantage of a more powerful processor, or to offload excess work.

In an illustrative example, some devices may be configured with a mobile chip including an engine adapted to implement specialized processing, such as, for example, neural networks, machine learning, artificial intelligence, image recognition, audio processing, or digital signal processing. In some embodiments, such an engine adapted to specialized processing may have sufficient processing power to implement some features. However, in some embodiments, an exemplary discrete collection device 1645 may be configured to operate on a device with less processing power, such as, for example, various gaming consoles, which may not have sufficient processor power, or a suitable CPU architecture, to adequately support discrete collection device 1645. Various embodiment designs configured to operate on such a device with reduced processor power may work in conjunction with a more powerful server system.

Figure 20:
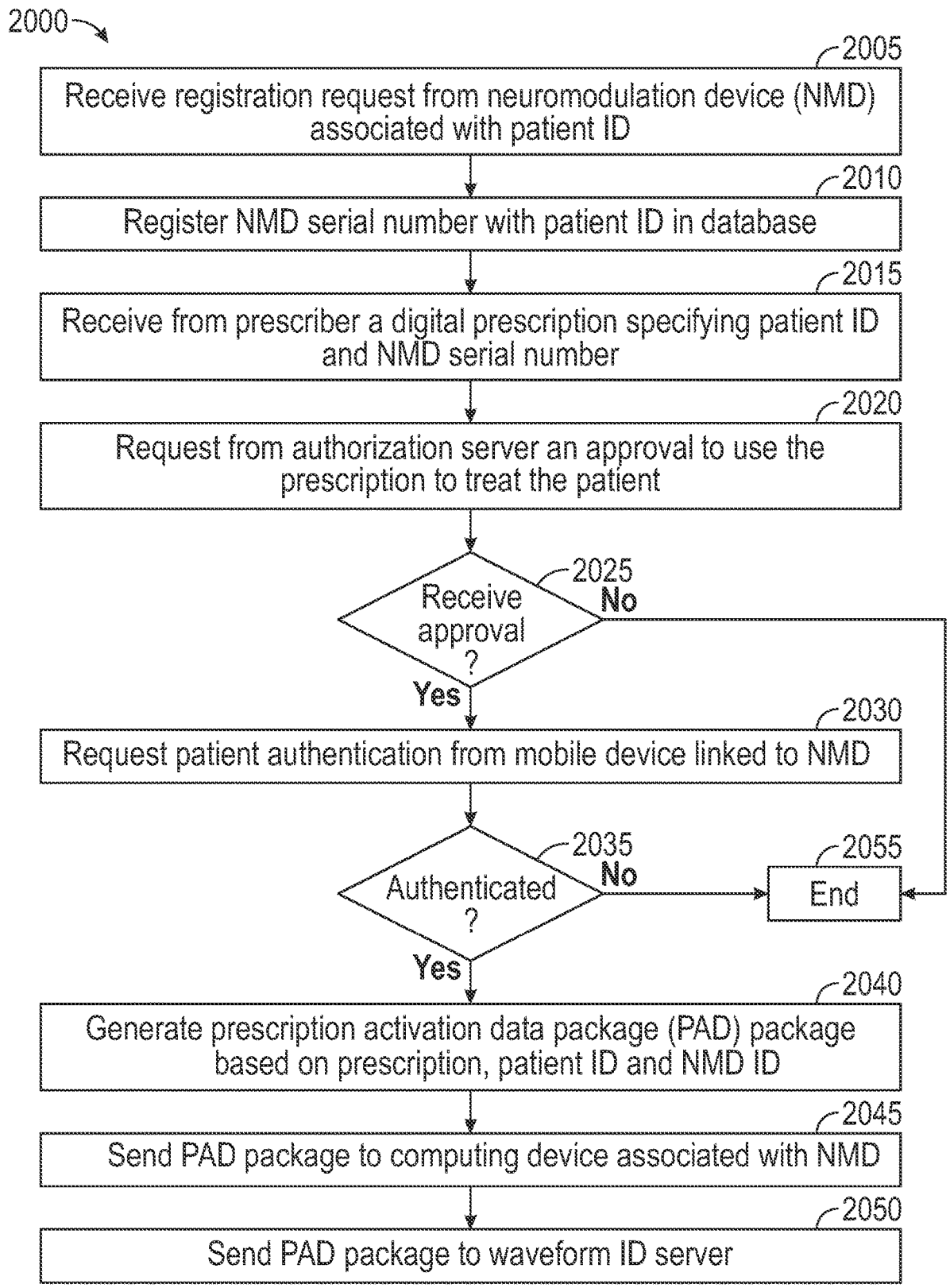

FIG. 20 depicts a process flow of an exemplary waveform prescription deployment process to receive a digital prescription for a neuromodulation device to apply a prescribed neuromodulation waveform to a patient, request biometric patient authentication by a computing device associated with the neuromodulation device and in response to receiving an indication of successful patient authentication, activating the neuromodulation device to apply the prescribed neuromodulation waveform to the patient, based on sending to the neuromodulation device a time-based one-time-password generated from a shared secret distributed during a registration phase.

The method 2000 depicted in FIG. 20 is given from the perspective of the waveform prescription deployment engine (WPDE) 1720 implemented via processor-executable program instructions executing on the waveform prescription deployment server 1625 processor 1700, depicted in FIG. 17. In the illustrated implementation, the WPDE 1720 executes as processor executable program instructions on the processor 1700 configured in the WPDE 1720 host waveform prescription deployment server 1625, depicted in at least FIG. 16. The WPDE 1720 may be configured to execute as a cloud service communicatively and operatively coupled via one or more communication network with system services, hardware resources, or software elements local to and/or external to the waveform prescription deployment server 1625.

The depicted method 2000 begins at step 2005 with the processor 1700 receiving a registration request from a neuromodulation device (NMD). The NMD may be an implantable pulse generator (IPG) 106, depicted in at least FIGS. 1A, 1B, 2, 11 and 16. The NMD may be a wearable pulse generator (WPG) 1610, depicted in at least FIG. 16. The NMD may be associated with a patient identification (patient ID). The patient ID may uniquely identify the patient. The patient ID may be provided with the registration request. The registration request may be received from the NMD or a computing device associated with the NMD. The registration request may include an NMD ID. The NMD ID may uniquely identify the NMD. The NMD ID may be an NMD serial number. With the registration request, the NMD or the computing device associated with the NMD may provide a trusted public key. The processor 1700 may generate a shared secret key based on the time when the registration request is received. The processor 1700 may generate a shared secret key based on the time when the registration request is received and the trusted public key.

The method continues at step 2010 with the processor 1700 registering the NMD ID with the patient ID. The NMD ID and the patient ID may be stored and associated together in a database with the shared secret key. The processor 1700 may distribute the shared secret key to the NMD. The processor 1700 may distribute the shared secret key to the computing device associated with the NMD.

The method continues at step 2015 with the processor 1700 receiving a digital prescription specifying the patient ID and the NMD ID. The prescription may be received from a prescriber system. The prescription may include the NMD ID. The NMD ID may be the NMD serial number. The prescription may comprise one or more neuromodulation waveforms to be applied to the patient using the NMD.

The method continues at step 2020 with the processor 1700 requesting an approval from a waveform prescription authorization server 1660 to use the prescription to treat the patient.

The method continues at step 2025 with the processor 1700 performing a test to determine if the requested approval was received. Upon a determination by the processor 1700 at step 2025 that the requested approval was not received the method continues to step 2055 where the method ends. Upon a determination by the processor 1700 at step 2025 that the requested approval was received the method continues at step 2030.

At step 2030 the processor 1700 requests patient authentication from a computing device 118 associated with the NMD, depicted at least in FIG. 16. The processor 1700 may request the computing device associated with the NMD to authenticate the patient based on patient biometric or security credential input. The computing device associated with the NMD may be a mobile device. The computing device associated with the NMD may be communicatively paired with or linked to the NMD. The processor 1700 may receive a security token generated by the computing device associated with the NMD upon successful patient authentication.

The method continues at step 2035 with the processor 1700 performing a test to determine if an indication of successful patient authentication was received from the computing device associated with the NMD. Upon a determination by the processor 1700 at step 2035 that the indication of successful patient authentication was not received, the method continues to step 2055 where the method ends. Upon a determination by the processor 1700 at step 2035 that the indication of successful patient authentication was received, the method continues at step 2040.

The method continues at step 2040 with the processor 1700 generating a prescription activation data package based on the prescription and the patient ID. The processor 1700 may generate the shared secret key based on the time when the prescription activation data package is generated. The processor 1700 generates a time-based one-time-password (TOTP) based on the security token and the shared secret.

The method continues at step 2045 with the processor 1700 sending the prescription activation data package and the TOTP to the NMD associated with the patient. The processor 1700 may send the prescription activation data package and the TOTP to the computing device associated with the NMD. The computing device associated with the NMD is configured to send the prescription activation data package and the TOTP to the NMD. The NMD is configured to be activated by the TOTP to apply or continue applying the prescribed neuromodulation waveform to the patient.

The method continues at step 2050 with the processor 1700 sending the prescription activation data package to a waveform identification server 1640, depicted at least in FIG. 16. The waveform identification server 1640 is configured to determine if signal characteristics of the prescribed neuromodulation waveform match signal characteristics of one or more waveform protocols applied to the patient by the NMD.

An exemplary waveform prescription deployment server 1625 method 2000 implementation has been disclosed with reference to FIG. 20, however other method 2000 implementations are contemplated. For example, an exemplary method 2000 implementation may comprise: receiving a registration request from the NMD or the computing device associated with the NMD, the registration request comprising a trusted public key associated with the NMD; registering the NMD; generating a shared secret based on the registration time and the trusted public key received from the NMD; distributing the shared secret to the NMD and/or to the computing device associated with the NMD; receiving a digital prescription; sending a request to a waveform prescription authorization server 1660 for approval to use the prescription; if approval is received from the waveform prescription authorization server 1660, requesting the computing device associated with NMD to authenticate the patient; if the patient is successfully authenticated by the computing device associated with the NMD, receiving a security token from the computing device associated with the NMD; in response to receiving the security token from the computing device associated with the NMD, generating a prescription activation data package and a time-based one-time password (TOTP) based on the security token and the shared secret generated at registration time; sending the prescription activation data package and the TOTP to the NMD and/or the computing device associated with the NMD, activating the NMD to use a prescribed waveform from the prescription activation data package; and sending the prescription activation data package to the waveform identification server 1640, to monitor for and detect usage of the prescribed waveforms identified in the prescription activation data package.

An exemplary method 2000 implementation may comprise: receiving an indication from waveform identification server 1640 that a known predetermined waveform is in use by an NMD associated with a patient, the indication comprising a patient ID and NMD ID; and in response to receiving the indication from waveform identification server 1640 that the known predetermined waveform is in use, sending a request for patient authentication to the computing device associated with the NMD.

An exemplary method 2000 implementation may comprise: receiving a request from the NMD or the computing device associated with the NMD for approval to use a particular known predetermined waveform identified in the request; forwarding the request for approval to the waveform prescription authorization server 1660; receiving a decision from the waveform prescription authorization server 1660 concerning the request for approval to use the particular known predetermined waveform to treat the patient; and upon determining the waveform prescription authorization server 1660 approved the request to use the particular known predetermined waveform, forwarding the approval to the NMD or the computing device associated with the NMD, with a prescription activation data package and a time-based one-time password based on a security token derived from successful patient authentication and the shared secret generated at registration time, activating the NMD to use or continue using the known predetermined waveform.

In some implementations, the method may repeat.

Figure 21:
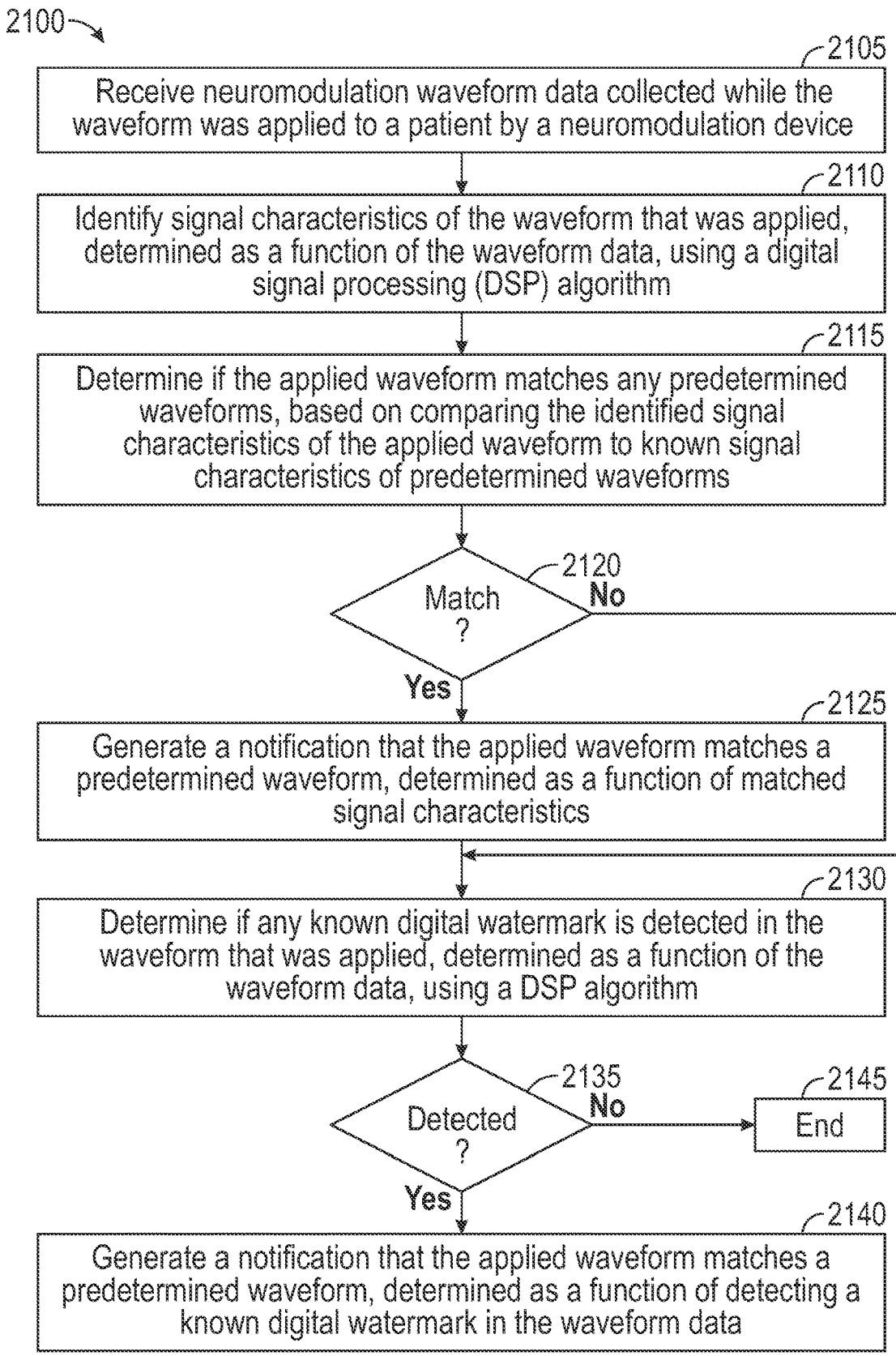

FIG. 21 depicts a process flow of an exemplary waveform identification process to receive collected signal data, identify signal characteristics or an embedded watermark in an applied neuromodulation waveform determined as a function of the collected signal data, and generate a notification if the applied neuromodulation waveform or watermark matches any known predetermined neuromodulation waveform or watermark, based on the identified signal characteristics.

The method 2100 depicted in FIG. 21 is given from the perspective of the waveform identification engine (WIE) 1820 implemented via processor-executable program instructions executing on the waveform identification server 1640 processor 1800, depicted in FIG. 18. In the illustrated implementation, the WIE 1820 executes as processor executable program instructions on the processor 1800 configured in the WIE 1820 host waveform identification server 1640, depicted in at least FIG. 16. The WIE 1820 may be configured to execute as a cloud service communicatively and operatively coupled via one or more communication network with system services, hardware resources, or software elements local to and/or external to the waveform identification server 1640.

The method begins at step 2105 with the processor 1800 receiving neuromodulation waveform data collected while the waveform was applied to a patient by a neuromodulation device. The collected neuromodulation waveform data may be waveform samples or measured signal characteristics or signal parameters. The collected neuromodulation waveform data may be received from the NMD, a computing device associated with the NMD or a discrete collection device.

The method continues at step 2110 with the processor 1800 identifying signal characteristics of the waveform that was applied, determined as a function of the collected waveform data, using a digital signal processing (DSP) algorithm.

The method continues at step 2115 with the processor 1800 determining if the applied waveform matches any known predetermined waveforms, based on comparing the identified signal characteristics of the applied waveform to known signal characteristics of known predetermined waveforms.

The method continues at step 2120 with the processor 1800 performing a test to determine if the applied waveform matches any known predetermined waveform. Upon a determination by the processor 1800 at step 2120 that the applied waveform matches at least one known predetermined waveform, the method continues at step 2125. Upon a determination by the processor 1800 at step 2120 that the applied waveform does not match any known predetermined waveform, the method continues at step 2130.

At step 2125, the processor 1800 generates a notification that the applied waveform matches a predetermined waveform, determined as a function of matched signal characteristics. The processor 1800 may send the notification to an authorization server configured to enforce treatment protocol conformance. The authorization server may forward the notification to a distributed ledger to trigger a smart contract configured to update waveform usage records associated with the patient.

At step 2130, the processor 1800 determines if any known digital watermark is detected in the waveform that was applied, determined as a function of the collected waveform data, using a DSP algorithm.

The method continues at step 2135 with the processor 1800 performing a test to determine if any known digital watermark was detected in the waveform that was applied. Upon a determination by the processor 1800 at step 2135 no known digital watermark was detected, the method continues to step 2145 where the method ends. Upon a determination by the processor 1800 at step 2135 at least one known digital watermark was detected, the method continues to step 2140.

At step 2140 the processor 1800 generates a notification that the applied waveform matches a predetermined waveform, determined as a function of detecting a known digital watermark in the waveform data. The processor 1800 may send the notification to an authorization server configured to enforce waveform usage restrictions using smart contracts. For example, the authorization server may forward the notification to a distributed ledger to trigger a smart contract configured to update waveform usage records associated with the patient.

An exemplary waveform identification server 1640 method 2100 implementation has been disclosed with reference to FIG. 21, however other method 2100 implementations are contemplated. For example, an exemplary method 2100 implementation may further comprise: receiving a prescription activation data package from a waveform prescription deployment server 1625, and monitor for and detecting usage of the prescribed waveforms identified in the prescription activation data package, based on processing collected waveform data; and sending a notification that a known predetermined waveform is in use, to the waveform prescription deployment server 1625 and the NMD or the computing device associated with the NMD.

In some implementations the method may repeat.

Figure 22:
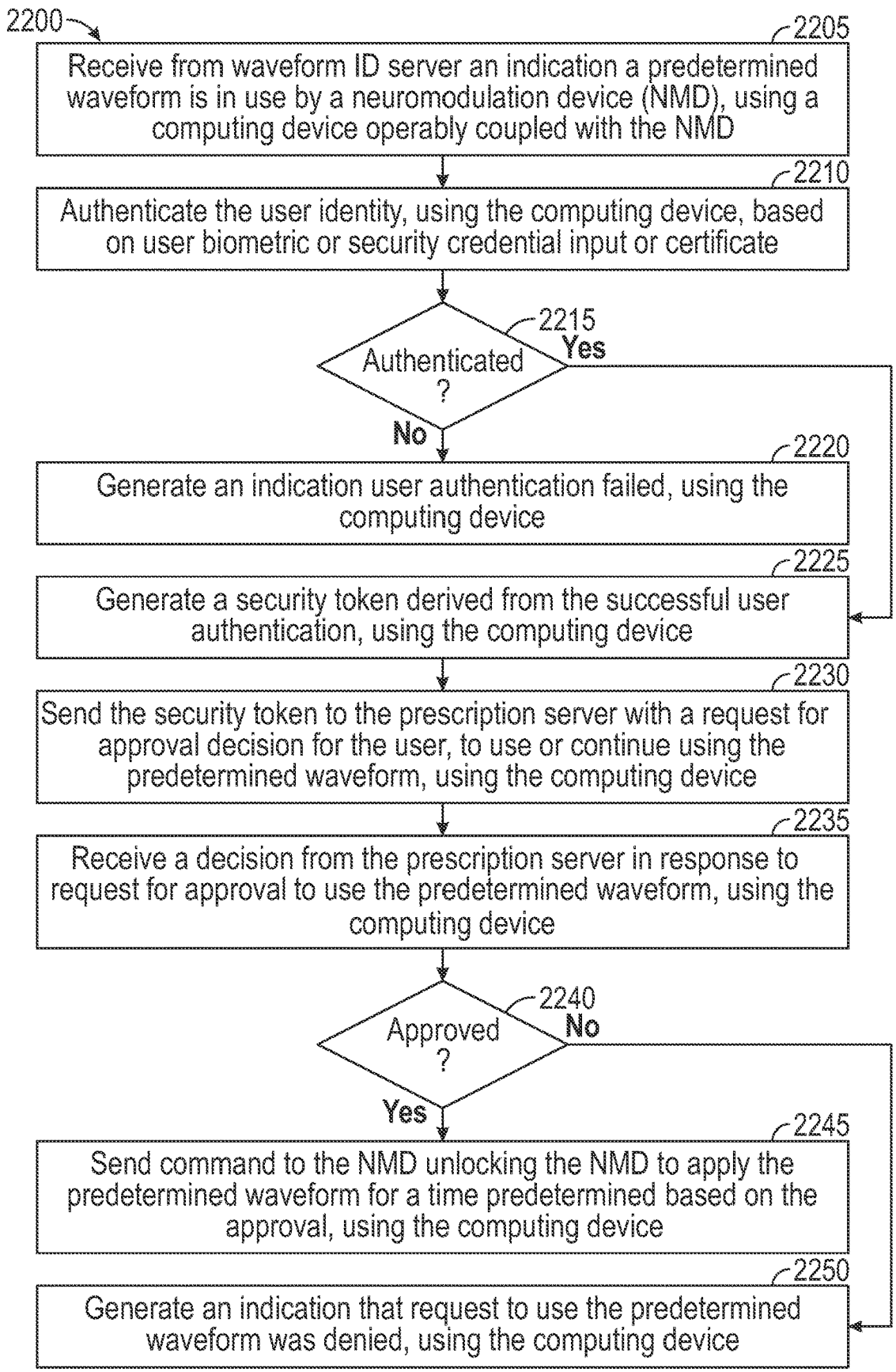

FIG. 22 depicts a process flow of an exemplary neuromodulation treatment management process to receive from a waveform identification server an indication that a known predetermined neuromodulation waveform is in use by a neuromodulation device treating a patient, authenticate the patient based on biometric input, generate a security token derived from the successful patient authentication and a shared secret, send the security token to a waveform prescription deployment server with a request for approval to continue treating the patient using the known predetermined neuromodulation waveform and in response to receiving the approval from the waveform prescription deployment server, activating the neuromodulation device to continue applying the prescribed neuromodulation waveform to the patient, based on sending to the neuromodulation device a time-based one-time-password generated from the shared secret distributed during a registration phase.

The method 2200 depicted in FIG. 22 is given from the perspective of a waveform treatment engine implemented via processor-executable program instructions executing as a mobile app 1620 on a computing device associated with an NMD. The computing device associated with the NMD may be the mobile device 118, depicted in at least FIG. 16. The mobile device 118 includes a processor, a network communication interface and a memory retaining processor executable program instructions configured that when executed by the processor, the program instructions cause the mobile device to perform operations implementing the mobile app 1620, depicted in FIG. 16. The mobile device 118 may be operably coupled via one or more network communication link with the SCS IPG 106 and/or the WPG 1610, depicted in at least FIG. 16. The mobile device 118 may be operably coupled via a communication link with the discrete collection device 1645, depicted in FIGS. 16 and 19. In the illustrated implementation, the mobile app 1620 executes as processor executable program instructions on the mobile device 118 processor. The mobile app 1620 may be configured to execute as a cloud service communicatively and operatively coupled via one or more communication network with system services, hardware resources, or software elements local to and/or external to the mobile app 118.

The method begins at step 2205 with the mobile device 118 processor receiving from a waveform ID server an indication a predetermined waveform is in use by the NMD.

The method continues at step 2210 with the mobile device 118 processor authenticating the user identity, using the computing device, based on user biometric or security credential input or a security certificate. The mobile device 118 processor may verify the user biometric input against a stored biometric template. The user may be a patient receiving treatment from the NMD. The user may be a clinical expert programming the NMD.

The method continues at step 2215 with the mobile device 118 processor performing a test to determine if the user was successfully authenticated. Upon a determination by the mobile device 118 processor at step 2215 that the user was not successfully authenticated, the method continues at step 2220. Upon a determination by the mobile device 118 processor at step 2215 that the user was successfully authenticated, the method continues at step 2225.

At step 2220, the mobile device 118 processor generates an indication user authentication failed and the method ends.

At step 2225, the mobile device 118 processor generates a security token derived from the successful user authentication and a shared secret key generated and distributed by the waveform prescription deployment server 1625 during a registration phase. The security token may be any data digitally signed with a trusted encryption key by the mobile device 118 processor.

The method continues at step 2230 with the mobile device 118 processor sending the security token to the prescription server with a request for approval decision for the user, to use or continue using the predetermined waveform.

The method continues at step 2235 with the mobile device 118 processor receiving a decision from the prescription server in response to request for approval to use the predetermined waveform. The approval may include a prescription activation data package comprising an indication of a prescribed neuromodulation waveform and a time-based one-time-password (TOTP) generated by the prescription server from the shared secret key distributed during a registration phase.

The method continues at step 2240 with the mobile device 118 performing a test to determine if the request for approval to use the predetermined waveform was approved. Upon a determination by the mobile device 118 processor at step 2240 that the request was not approved, the method continues at step 2250. Upon a determination by the mobile device 118 processor at step 2240 that the request was approved, the method continues at step 2245.

At step 2245 the mobile device 118 processor sends a command to the NMD unlocking the NMD to apply the predetermined waveform for a time predetermined based on the approval. The command may comprise the prescription activation data package and the TOTP. The NMD is configured to be activated by the TOTP to apply or continue applying the prescribed neuromodulation waveform to the patient.

At step 2250 the mobile device 118 processor generates an indication that request to use the predetermined waveform was denied, and the method ends.

An exemplary neuromodulation treatment management method 2200 implementation executing on the computing device associated with the NMD has been disclosed with reference to FIG. 22, however other method 2200 implementations are contemplated. For example, an exemplary method 2200 implementation may comprise: sending a registration request to the waveform prescription deployment server 1625, with a trusted public key associated with the NMD; receiving a shared secret generated by the waveform prescription deployment server 1625 based on the registration time and the trusted public key; receiving a request from the waveform prescription deployment server 1625 to authenticate the patient; upon determining patient authentication was successful, generating a security token derived from the successful patient authentication and the shared secret; sending the security token to the waveform prescription deployment server 1625; in response to sending the security token to the waveform prescription deployment server 1625, receiving from the waveform prescription deployment server 1625 a prescription activation data package and a time-based one-time password (TOTP) based on the security token and the shared secret; validating the TOTP using the shared secret; upon determining the TOTP is valid, sending the prescription activation data package and the TOTP to the NMD, activating the NMD to use or continue using a predetermined waveform identified by the prescription activation data package.

An exemplary method 2200 implementation may comprise: sending a registration request to the waveform prescription deployment server 1625, with a trusted public key associated with the NMD; receiving a shared secret generated by the waveform prescription deployment server 1625 based on the registration time and the trusted public key; receiving from a waveform identification server 1640, an indication that a known predetermined waveform is in use; receiving request from the waveform prescription deployment server 1625 to authenticate the patient; upon determining patient authentication was successful, generating a security token derived from the successful patient authentication and the shared secret, wherein the security token may be any data digitally signed with a trusted encryption key; sending the security token to the waveform prescription deployment server 1625 with a request for approval to use the waveform that was detected in use; receiving a decision from the waveform prescription deployment server 1625 concerning the request for approval; upon determining the request was approved, receiving with the decision from the waveform prescription deployment server 1625 a prescription activation data package and a time-based one-time password (TOTP) based on the security token and the shared secret; validating the TOTP using the shared secret; upon determining the TOTP is valid, sending the prescription activation data package and the TOTP to the NMD, activating the NMD to use or continue using a predetermined waveform identified by the prescription activation data package.

In some implementations the method may repeat.

Figure 23:
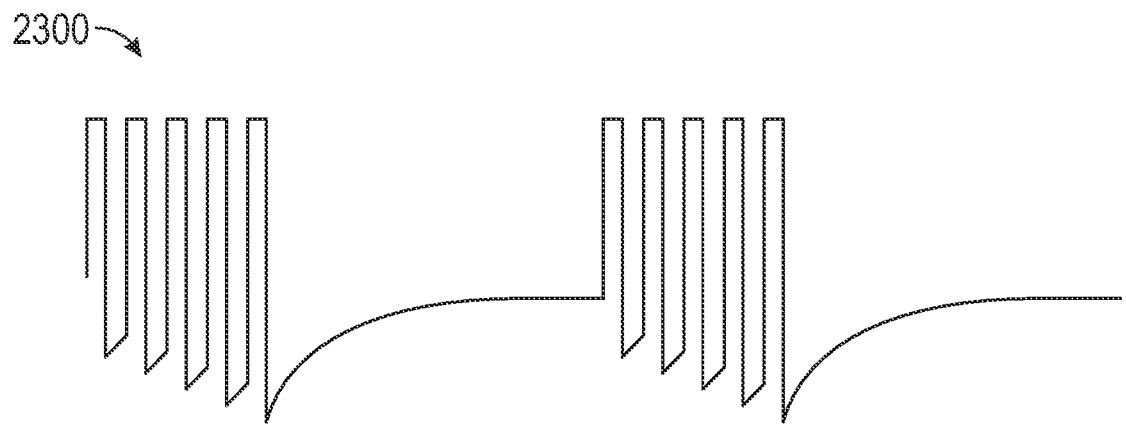

FIG. 23 depicts the exemplary burst neuromodulation waveform 2300.

Figure 24:
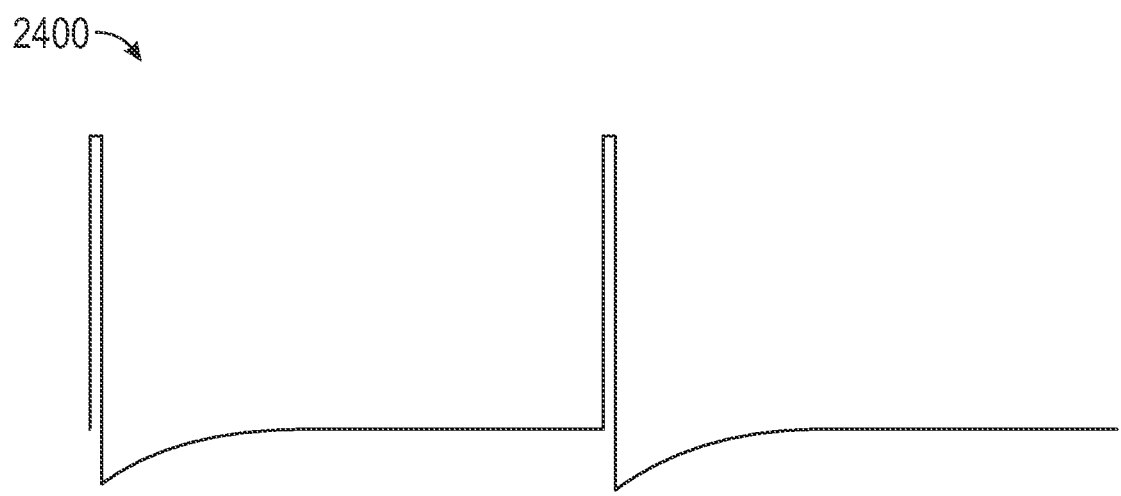

FIG. 24 depicts the exemplary tonic neuromodulation waveform 2400.

Figure 25:
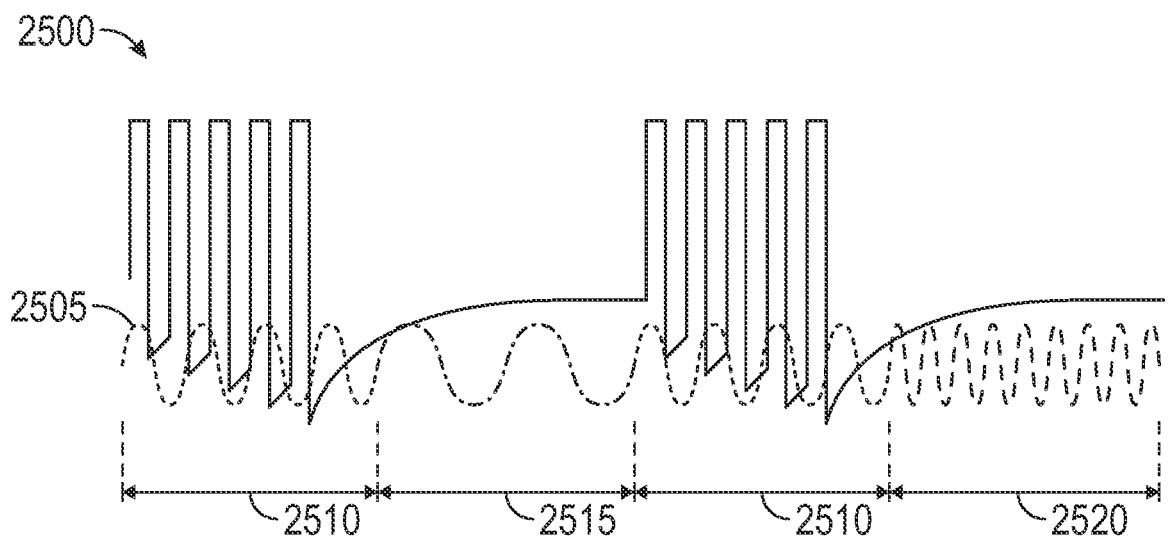

FIG. 25 depicts an exemplary watermarked burst neuromodulation waveform with watermark data encoded by frequency modulation (FM). In FIG. 25, the exemplary watermarked burst neuromodulation waveform 2500 is illustrated with the modulated carrier wave 2505. In the depicted implementation, the carrier wave 2505 encodes watermark data in the burst neuromodulation waveform 2500 by frequency modulation (FM). In the depicted example, the burst neuromodulation waveform 2500 is divided in the time domain into sections to aid description. In a first section, the "one" bit 2510 is frequency modulated in the burst neuromodulation waveform 2500 using a first predetermined frequency to encode a digital "one." In a second section, the "zero" bit 2515 is frequency modulated in the burst neuromodulation waveform 2500 using a second predetermined frequency to encode a digital "zero." In the depicted implementation, the second predetermined frequency is lower than the first frequency, permitting a receiver configured to track the carrier frequency to identify the change in frequency. In a third section, another "one" bit 2510 is frequency modulated in the burst neuromodulation waveform 2500 using the first predetermined frequency. The depicted implementation is an example of encoding the binary sequence "one zero one" in the burst neuromodulation waveform 2500. The binary sequence may be extended for any useful length to encode arbitrary data in the burst neuromodulation waveform 2500. The encoded arbitrary data may be a digital watermark identifying the waveform for tracking, identification, licensing enforcement, or automatic invoicing. The watermark may be identified by a watermark detection algorithm. In a fourth section, the carrier wave 2505 is illustrated as a third predetermined frequency. The third predetermined frequency is the carrier wave 2505 center frequency 2520. The binary sequence may be decoded by a receiver configured to track deviation of the carrier wave 2505 frequency from the carrier wave 2505 center frequency 2520. The carrier wave 2505 center frequency 2520 may be used as an idle period when no data is added to a neuromodulation waveform. An implementation may use a carrier wave 2505 having an amplitude of 10% or less of paresthesia (0.1-0.2 mA) to avoid effects on neural or cellular activity, while being strong enough for collection and measurement. The depicted carrier wave 2505 is sinusoidal. The carrier wave 2505 may be any type of waveform. Waveform types other than sinusoidal waveforms may be used to implement the carrier wave 2505.

Figure 26:
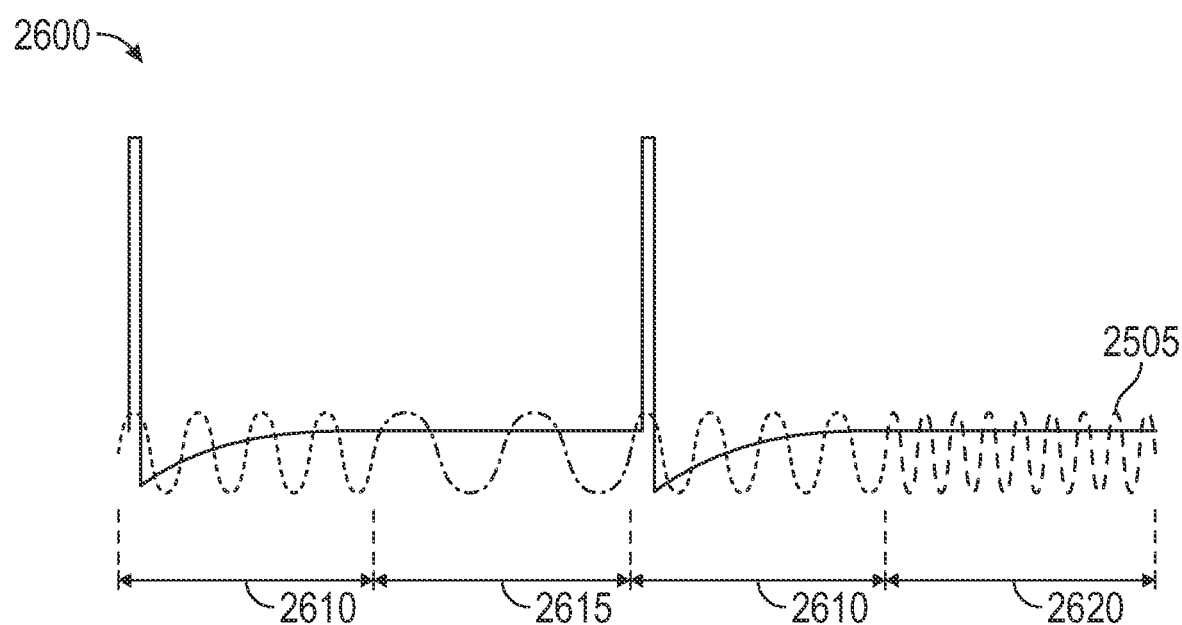

FIG. 26 depicts an exemplary watermarked tonic neuromodulation waveform with watermark data encoded by frequency modulation (FM). In FIG. 26, the exemplary watermarked tonic neuromodulation waveform 2600 is illustrated with the modulated carrier wave 2505. In the depicted implementation, the carrier wave 2505 encodes watermark data in the tonic neuromodulation waveform 2600 by frequency modulation (FM). In the depicted example, the tonic neuromodulation waveform 2600 is divided in the time domain into sections to aid description. In a first section, the "one" bit 2610 is frequency modulated in the tonic neuromodulation waveform 2600 using a first predetermined frequency to encode a digital "one." In a second section, the "zero" bit 2615 is frequency modulated in the tonic neuromodulation waveform 2600 using a second predetermined frequency to encode a digital "zero." In the depicted implementation, the second predetermined frequency is lower than the first frequency, permitting a receiver configured to track the carrier frequency to identify the change in frequency. In a third section, another "one" bit 2610 is frequency modulated in the tonic neuromodulation waveform 2600 using the first predetermined frequency. The depicted implementation is an example of encoding the binary sequence "one zero one" in the tonic neuromodulation waveform 2600. The binary sequence may be extended for any useful length to encode arbitrary data in the tonic neuromodulation waveform 2600. The encoded arbitrary data may be a digital watermark identifying the waveform for tracking, identification, licensing enforcement, or automatic invoicing. The watermark may be identified by a watermark detection algorithm. In a fourth section, the carrier wave 2505 is illustrated as a third predetermined frequency. The third predetermined frequency is the carrier wave 2505 center frequency 2620. The binary sequence may be decoded by a receiver configured to track deviation of the carrier wave 2505 frequency from the carrier wave 2505 center frequency 2620. The carrier wave 2505 center frequency 2620 may be used as an idle period when no data is added to a neuromodulation waveform. An implementation may use a carrier wave 2505 having an amplitude of 10% or less of paresthesia (0.1-0.2 mA) to avoid effects on neural or cellular activity, while being strong enough for collection and measurement. The depicted carrier wave 2505 is sinusoidal. The carrier wave 2605 may be any type of waveform. Waveform types other than sinusoidal waveforms may be used to implement the carrier wave 2505.

Figure 27:
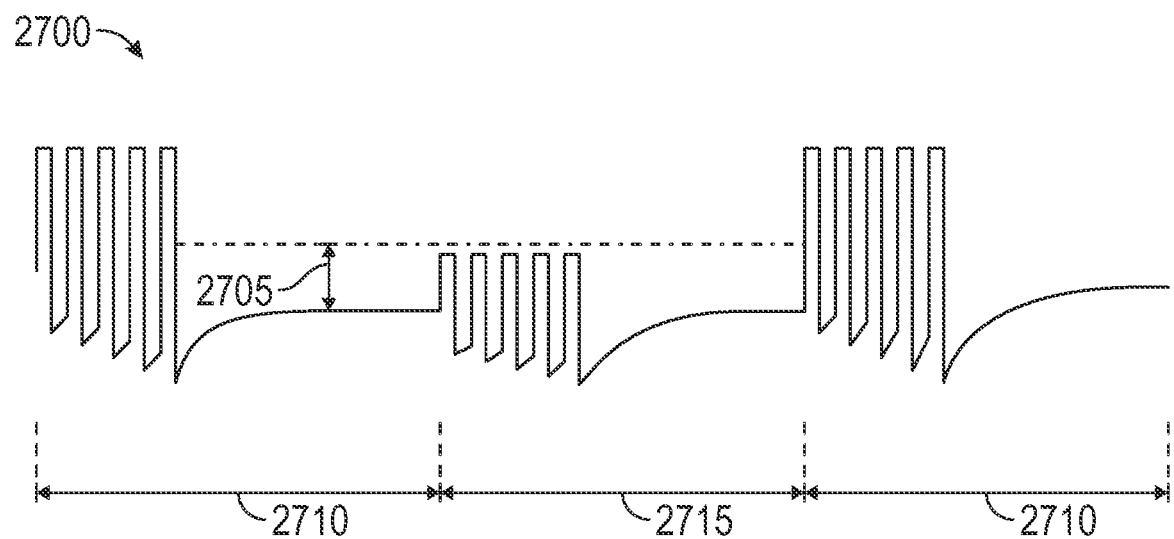

FIG. 27 depicts an exemplary watermarked burst neuromodulation waveform with watermark data encoded by amplitude modulation (AM). In FIG. 27, the exemplary watermarked burst neuromodulation waveform 2700 is amplitude-modulated. In the depicted implementation the burst neuromodulation waveform 2700 amplitude is varied up or down by the amplitude delta 2705 to modulate watermark data in the waveform. In a first section the "one" bit 2710 is amplitude-modulated in the burst neuromodulation waveform 2700 using a first predetermined amplitude to encode a digital "one." In a second section the "zero" bit 2715 is amplitude-modulated in the burst neuromodulation waveform 2700 using a using a second predetermined amplitude to encode a digital "zero." In a third section, another "one" bit 2710 is amplitude-modulated in the burst neuromodulation waveform 2700. In the depicted implementation the second predetermined amplitude is less than the first predetermined amplitude, permitting a receiver configured to detect the varying amplitude to identify the change in amplitude.

The depicted implementation is an example of encoding the binary sequence "one zero one" in the burst neuromodulation waveform 2700. The binary sequence may be extended for any useful length to encode arbitrary data in the burst neuromodulation waveform 2700. The encoded arbitrary data may be a digital watermark identifying the waveform for tracking, identification, licensing enforcement, or automatic invoicing. The watermark may be identified by a watermark detection algorithm. Transmitting identifying watermark data through an amplitude-modulated neuromodulation waveform may permit encoding arbitrary data without changing any waveform parameters other than amplitude. Changing a neuromodulation waveform using techniques other than amplitude modulation may result in a substantially new waveform with unpredictable and possibly adverse effects on patients. Such a new neuromodulation waveform may require time-consuming testing and/or regulatory approval.

Figure 28:
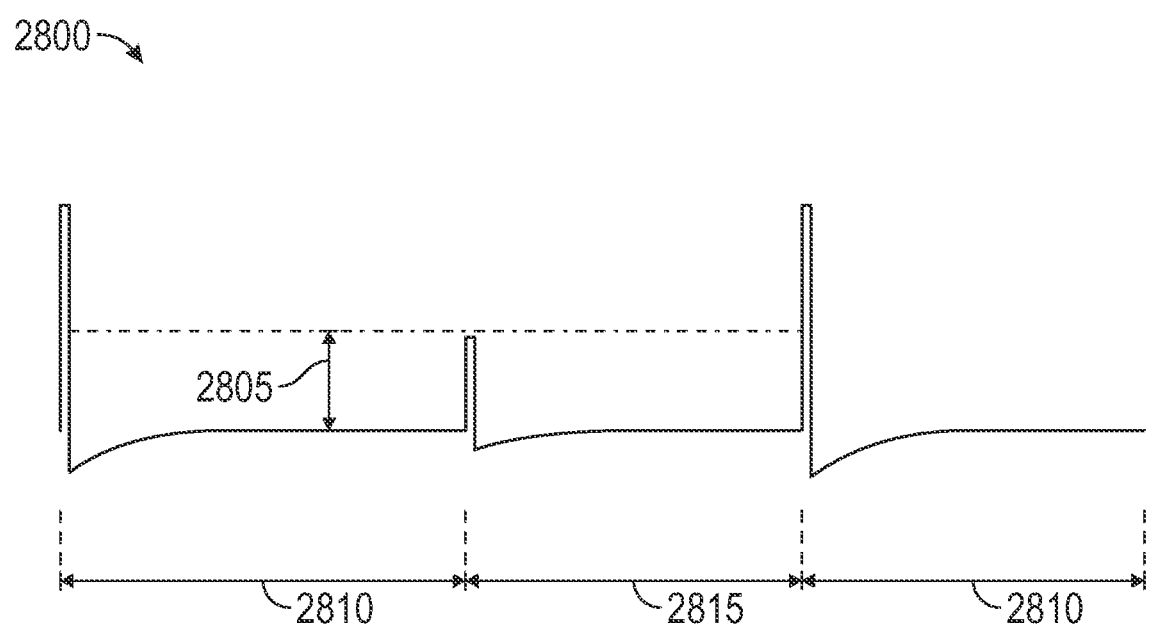

FIG. 28 depicts an exemplary watermarked tonic neuromodulation waveform with watermark data encoded by amplitude modulation (AM). In FIG. 28, the exemplary watermarked tonic neuromodulation waveform 2800 is amplitude-modulated. In the depicted implementation the tonic neuromodulation waveform 2800 amplitude is varied up or down by the amplitude delta 2805 to modulate watermark data in the waveform. In a first section the "one" bit 2810 is amplitude-modulated in the tonic neuromodulation waveform 2800 using a first predetermined amplitude to encode a digital "one." In a second section the "zero" bit 2815 is amplitude-modulated in the tonic neuromodulation waveform 2800 using a using a second predetermined amplitude to encode a digital "zero." In a third section, another "one" bit 2810 is amplitude-modulated in the tonic neuromodulation waveform 2800. In the depicted implementation the second predetermined amplitude is less than the first predetermined amplitude, permitting a receiver configured to detect the varying amplitude to identify the change in amplitude. The depicted implementation is an example of encoding the binary sequence "one zero one" in the tonic neuromodulation waveform 2800. The binary sequence may be extended for any useful length to encode arbitrary data in the tonic neuromodulation waveform 2800. The encoded arbitrary data may be a digital watermark identifying the waveform for tracking, identification, licensing enforcement, or automatic invoicing. The watermark may be identified by a watermark detection algorithm.

An implementation configured to add a digital watermark to a known predetermined neuromodulation waveform using amplitude modulation techniques may preserve efficacy, reduce or eliminate adverse effects and avoid regulatory approval testing while permitting independent waveform usage detection. An implementation transmitting identifying watermark data through an amplitude-modulated neuromodulation waveform may transmit watermark data only periodically during an active watermark period. For example an implementation may amplitude-modulate a waveform to transmit watermark data once per hour for five minutes at a time, with the waveform unmodified for the balance of each hour. Transmitting amplitude-modulated watermark data in a neuromodulation waveform only periodically may ensure patients have the exact treatment their doctor prescribed for a significant fraction of each day, while avoiding substantial changes to the waveform when transmitting watermark data.

Figure 29A:
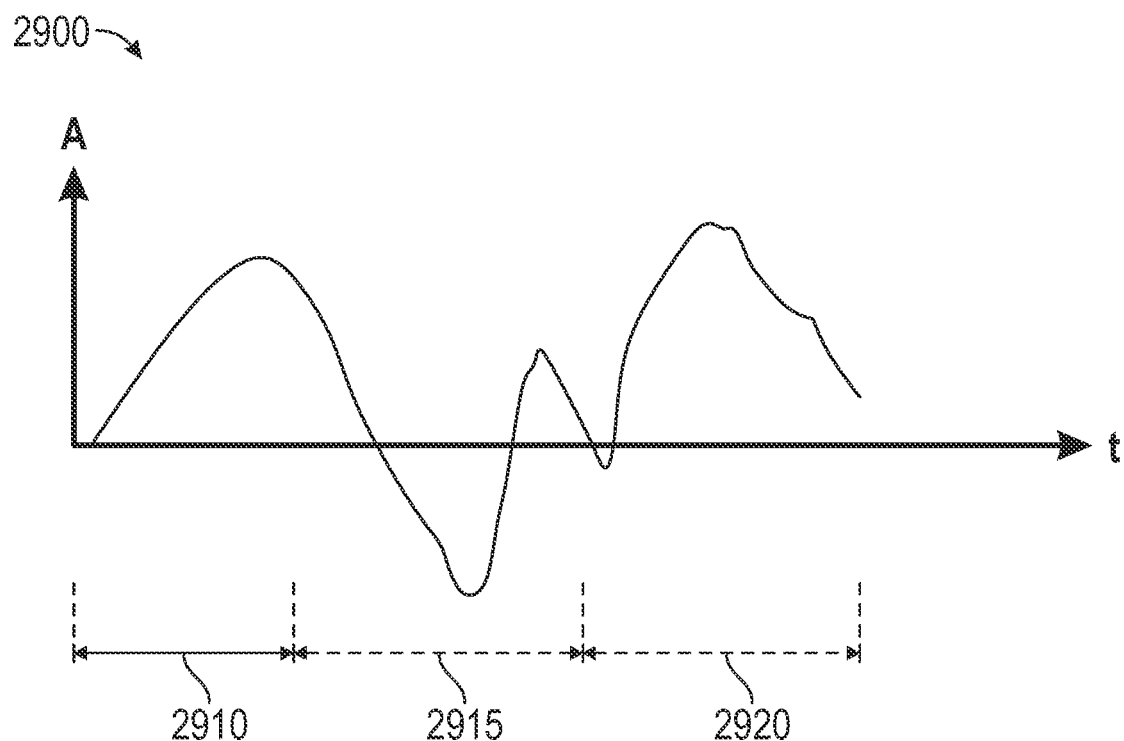
FIGS. 29A-29B together depict a graph view of processing an applied waveform signal and a known predetermined waveform signal in the time domain to determine if the applied waveform matched the known predetermined waveform signal.
Figure 29B:
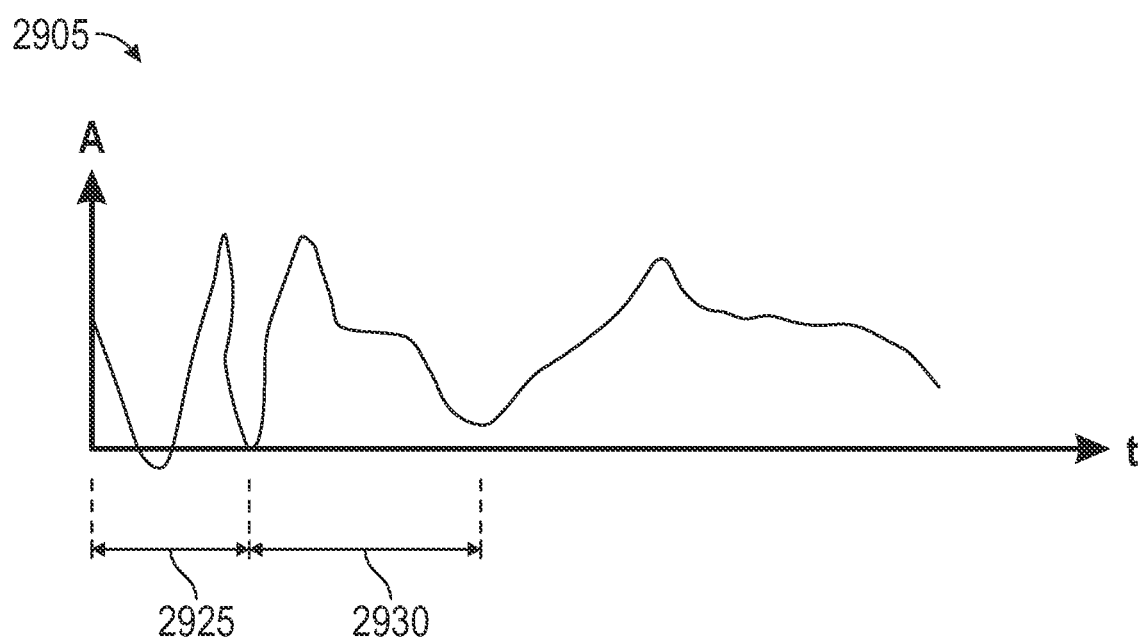

FIGS. 29A-29B together depict a graph view of processing an applied waveform signal and a known predetermined waveform signal in the time domain to determine if the applied waveform matched the known predetermined waveform signal. The processing described with reference to FIGS. 29A-29B is given from the perspective of the waveform identification server 1640 processor 1800, depicted in FIG. 18. The processing may be performed by an NMD, or a computing device associated with the NMD. In the depicted implementation the applied waveform signal 2900 is compared to the known predetermined waveform 2905. The depicted applied waveform signal 2900 represents samples of applied waveform energy. In the depicted example samples of the applied waveform signal 2900 are collected by the processor 1800 using an input electrode contacting a patient while a neuromodulation device (NMD) applies a neuromodulation waveform using an output electrode contacting the patient. The depicted known predetermined waveform signal 2905 is a time domain template or model of the known predetermined waveform. The processor 1800 may compare the applied waveform signal 2900 to multiple known predetermined waveform signals 2905, to determine if the applied waveform matches any of the multiple known predetermined waveform signals 2905.

The processor may normalize the amplitudes of the applied waveform signal 2900 and the known predetermined waveform signal 2905 to a common scale, to reduce adverse impact to signal amplitudes from impedance mismatch with the patient's body. The applied waveform signal 2900 may be smoothed by the processor 1800 using a low pass filter to remove spikes, noise and artifacts resulting from the collection processing. The processor 1800 may apply a bandpass filter to the applied waveform signal 2900 samples to remove noise and isolate a frequency range of interest, depending on the frequency spectrum of the known predetermined waveform signal 2905. The processor 1800 may remove one or more ECAP signal from the applied waveform samples as described herein. In the depicted example the processor 1800 segments the collected signal samples of the applied waveform signal 2900 into three windows 2910, 2915 and 2920. The processor 1800 compares the initial window 2925 of the known predetermined waveform to the first window 2910 of the applied waveform signal. The processor 1800 may compute cross-correlation values between the windows being compared. The cross-correlation may be computed in the frequency domain to reduce computation effort.

The processor 1800 may iteratively shift the initial window 2925 of the known predetermined waveform in time as each cross-correlation iteration is computed. An increasing cross-correlation value may indicate features such as peaks or troughs of the waveforms being compared have been aligned. When the processor 1800 detects a cross-correlation value satisfying a predetermined threshold the processor may stop iterative time-shifting and cross-correlation, and proceed to compare the waveform windows sample-by-sample. The predetermined threshold may be specified in a prescription activation data package. The processor 1800 may use features of the known predetermined waveform signal 2905 such as number, time offset and amplitude of peaks and troughs to align the initial window 2925 of the known predetermined waveform to the first window 2910 of the applied waveform signal. In the depicted implementation, the processor 1800 computes a low cross-correlation value between the initial window 2925 of the known predetermined waveform and the first window 2910 of the applied waveform signal. The processor 1800 determines the first window 2910 of the applied waveform signal does not match the initial window 2925 of the known predetermined waveform 2905, based on the low cross-correlation value.

The processor 1800 continues to compare the waveforms, advancing to compare the second window 2930 of the known predetermined waveform 2905 to the second window 2915 of the applied waveform. The processor 1800 may continue comparing all windows of the applied waveform 2900 to the known predetermined waveform 2905. Upon determination by the processor 1800 that the applied waveform 2900 matches the known predetermined waveform 2905, based on a cross-correlation value satisfying a predetermined minimum, the processor 1800 may send a notification that the known predetermined waveform 2905 is in use.

Figure 30A:
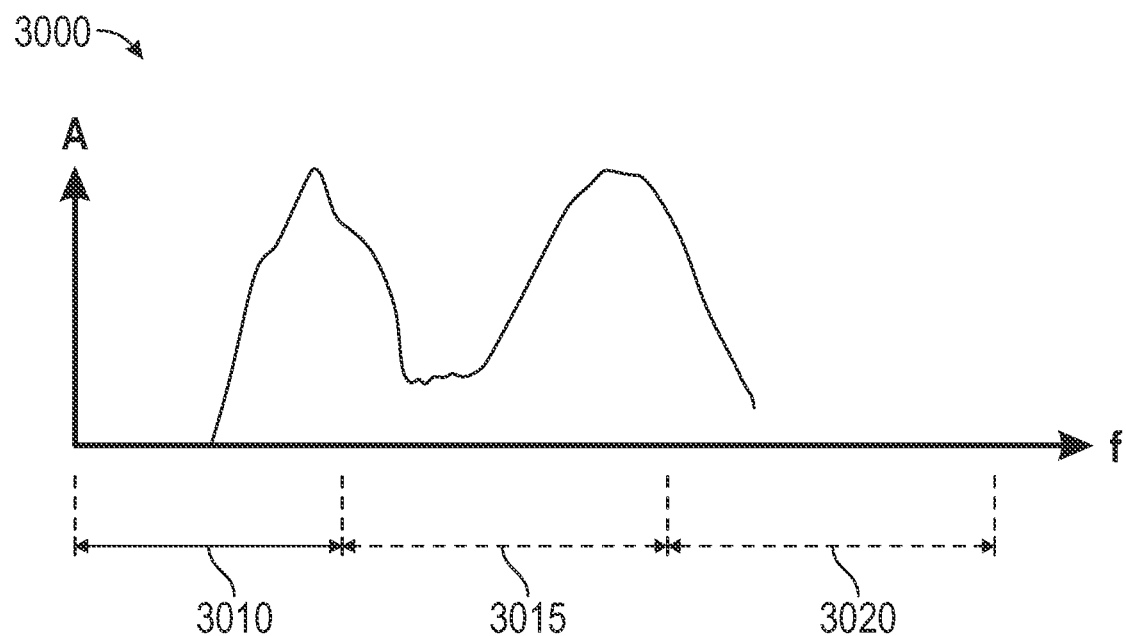
FIGS. 30A-30B together depict a graph view of processing an applied waveform signal and a known predetermined waveform signal in the frequency domain to determine if the applied waveform matched the known predetermined waveform signal.
Figure 30B:
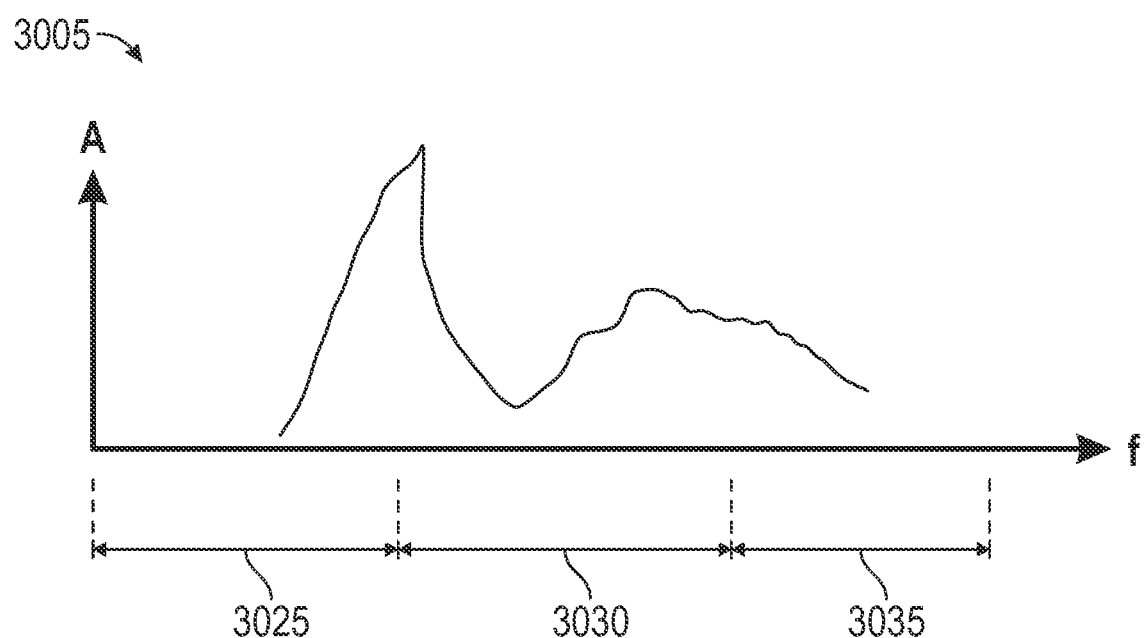

FIGS. 30A-30B together depict a graph view of processing an applied waveform signal and a known predetermined waveform signal in the frequency domain to determine if the applied waveform matched the known predetermined waveform signal. The processing described with reference to FIGS. 30A-30B is given from the perspective of the waveform identification server 1640 processor 1800, depicted in FIG. 18. The processing may be performed by an NMD, or a computing device associated with the NMD. In the depicted implementation the applied waveform signal 3000 is compared to the known predetermined waveform 3005. The depicted applied waveform signal 3000 represents frequency domain samples of applied waveform energy. In the depicted example samples of the applied waveform signal 3000 are collected by the processor 1800 using an input electrode contacting a patient while a neuromodulation device (NMD) applies a neuromodulation waveform using an output electrode contacting the patient. The samples of the applied waveform signal 3000 are transformed by the processor 1800 into the frequency domain using a discrete Fourier transform (DFT). The depicted known predetermined waveform signal 3005 is a frequency domain template or model of the known predetermined waveform. The processor 1800 may compare the applied waveform signal 3000 to multiple known predetermined waveform signals 3005, to determine if the applied waveform matches any of the multiple known predetermined waveform signals 3005.

In the depicted example the processor 1800 segments the frequency domain representation of the applied waveform signal 3000 into three windows 3010, 3015 and 3020 and segments the frequency domain representation of the known predetermined waveform signal 3005 into windows 3025, 3030 and 3035. The processor 1800 may compare power spectra or power spectral densities of the applied waveform signal 3000 and the known predetermined waveform signal 3005. The power spectra or power spectral densities' comparisons may be frequency bin by frequency bin comparisons. The processor 1800 may smooth the power spectra of the applied waveform signal 3000 and the known predetermined waveform signal 3005 using a low pass filter, to reduce the number of data points to be computed by cross-correlation and reduce processing load. The processor 1800 proceeds to compare the applied waveform signal 3000 and the known predetermined waveform signal 3005 in the frequency domain and generate a notification if the known predetermined waveform signal 3005 is in use, in line with what has been described above for the time domain case.

Although various embodiments have been described with reference to the Drawings, other embodiments are possible.

An exemplary method may comprise: receiving, by a waveform prescription deployment server (1625), a digital prescription for a neuromodulation device (NMD) to apply one or more prescription waveform protocols (1605) to a patient (115); sending, by the waveform prescription deployment server (1625), to a computing device associated with the NMD, a request for patient (115) authentication by the computing device associated with the NMD; in response to receiving, by the waveform prescription deployment server (1625), an indication of successful patient (115) authentication, generating and sending, by the waveform prescription deployment server (1625) to the computing device associated with the NMD, a prescription activation data package activating the NMD to apply the one or more prescription waveform protocols (1605) to the patient (115); and sending, by the waveform prescription deployment server (1625) to a waveform identification server (1640), an electronic message configured to cause the waveform identification server (1640) to determine if signal characteristics of the one or more prescription waveform protocols (1605) match signal characteristics of one or more waveform protocols applied to the patient (115) by the NMD.

The NMD may be an implantable pulse generator (IPG) 106 or a wearable pulse generator (WPG) 1610.

The method may further comprise receiving, by the waveform prescription deployment server (1625), a registration request uniquely identifying the patient (115) and the NMD, wherein the registration request may further comprise a trusted public key associated with the NMD.

The method may further comprise receiving the registration request from the NMD, with a trusted public key associated with the NMD.

The method may further comprise receiving the registration request from the computing device associated with the NMD.

The method may further comprise: receiving, by the waveform prescription deployment server (1625), a unique ID number for the patient (115) and a unique NMD serial number; and associating the NMD with the patient (115) based on storing the unique ID number for the patient (115) and the unique NMD serial number in a data store (1615) operably coupled with the waveform prescription deployment server (1625).

The computing device associated with the NMD may be a mobile device (118) configured to be operably coupled with the NMD.

The computing device associated with the NMD may be operably coupled with the NMD.

The computing device associated with the NMD may be a mobile device (118) hosting an application (1620) configured to permit a clinical expert to program the NMD.

The computing device associated with the NMD may be a mobile device hosting an application (1620) configured to permit a patient to operate the NMD.

The method may further comprise sending, by the waveform prescription deployment server (1625), to a waveform prescription authorization server (1660), a request for an approval to treat the patient (115) using the one or more prescription waveform protocols (1605) for a predetermined time.

The request for the approval to treat the patient (115) may further comprise a request to use the one or more prescription waveform protocols (1605) within a radius of a location determined based on location sensor data captured by the NMD or the computing device associated with the NMD.

The method may further comprise receiving, by the waveform prescription deployment server (1625), from the waveform prescription authorization server (1660), the approval to treat the patient (115) using the one or more prescription waveform protocols (1605).

The prescription activation data package may comprise an indication of the one or more prescription waveform protocols (1605) and a prescription expiration time.

The prescription activation data package may further comprise an indication of a default waveform protocol and the NMD is configured to cease applying the one or more prescription waveform protocols (1605) and begin applying the default waveform protocol when: a prescription expiration time is reached; or when the NMD moves outside a radius of an NMD location configured in the NMD, wherein when the NMD moves outside the configured radius is determined as a function of location sensor data captured by the NMD or the computing device associated with the NMD.

The prescription activation data package may further comprise a radius of an NMD location, within which radius the NMD may apply the one or more prescription waveform protocols (1605) to the patient (115).

The NMD may be configured to apply the one or more prescription waveform protocols (1605) to the patient (115) until a predetermined expiration time.

The NMD may be configured to cease applying the one or more prescription waveform protocols (1605) to the patient (115) when a predetermined expiration time is reached.

The NMD may be configured to apply the one or more prescription waveform protocols (1605) to the patient (115) when the NMD is within a radius of an NMD location specified by the prescription activation data package, based on location sensor data captured by the NMD or the computing device associated with the NMD.

The NMD may be configured to cease applying the one or more prescription waveform protocols (1605) to the patient (115) when the NMD moves outside a radius of an NMD location specified by the prescription activation data package, based on location sensor data captured by the NMD or the computing device associated with the NMD.

The method may further comprise downloading the one or more prescription waveform protocols (1605) to the NMD using an application deployed to the computing device associated with the NMD.

Patient (115) authentication may further comprise receiving and verifying patient (115) security credential input, using the computing device associated with the NMD.

Patient (115) authentication may further comprise the computing device associated with the NMD receiving and verifying patient (115) gesture or pattern input.

Patient (115) authentication may further comprise the computing device associated with the NMD receiving and verifying patient (115) time-based one-time-password (TOTP) input against a TOTP configured to change at least once per hour.

Activating the NMD to apply the one or more prescription waveform protocols (1605) to the patient (115) may further comprise receiving and verifying patient (115) time-based one-time-password (TOTP) input against a TOTP configured to change at least once per hour, using the NMD.

The method may further comprise receiving, by the NMD, from the computing device associated with the NMD, the TOTP.

A correct TOTP may be determined as a function of time and a shared secret generated by the waveform prescription deployment server (1625).

The method may further comprise the waveform prescription deployment server (1625) generating the shared secret based on a trusted public key received from the computing device associated with the NMD during registration and a time when the prescription activation data package is generated.

The method may further comprise receiving, by the waveform prescription deployment server (1625), a registration request uniquely identifying the patient (115) and the NMD, the registration request further comprising a trusted public key associated with the NMD; and generating, by the waveform prescription deployment server (1625), the shared secret based on the trusted public key and a time when the registration request is received.

The may further comprise sending, by the waveform prescription deployment server (1625), to the NMD, the shared secret.

The method may further comprise sending, by the waveform prescription deployment server (1625), to the computing device associated with the NMD, the shared secret.

The method may further comprise sending, by the computing device associated with the NMD, to the NMD, the shared secret.

The prescription activation data package may further comprise the shared secret.

The method may further comprise the NMD refraining from applying the one or more prescription waveform protocols (1605) to the patient (115) unless a correct TOTP is received from the computing device associated with the NMD, using the NMD.

The method may further comprise the NMD activating to apply the one or more prescription waveform protocols (1605) to the patient (115) when a correct TOTP is received from the computing device associated with the NMD, using the NMD.

The method may further comprise generating the TOTP based on RFC 4226.

The method may further comprise generating the TOTP based on RFC 6238.

Patient (115) authentication may further comprise receiving patient (115) biometric input and verifying the patient (115) biometric input against a stored biometric template, using the computing device associated with the NMD.

The patient (115) biometric input and the stored biometric template may further comprise data captured from at least one of: a fingerprint for fingerprint identification, a voice for speaker identification, a face for facial recognition, a retina for eye identification or a gesture.

Receiving the indication of successful patient (115) authentication may further comprise receiving an authentication token or cryptographic key generated by the computing device associated with the NMD in response to user biometric input verified against a stored biometric template.

The method may further comprise receiving, by a waveform identification server (1640), collected neuromodulation waveform data comprising sampled waveform signal data or measured waveform signal characteristics, the neuromodulation waveform data collected while one or more waveforms were applied to the patient (115).

The collected neuromodulation waveform data may be collected using at least one input electrode in contact with the patient (115) while the one or more waveforms is applied to the patient (115) using at least one output electrode in contact with the patient (115).

The collected neuromodulation waveform data may further comprise data representing energy from the one or more waveforms that were applied to the patient (115).

The collected neuromodulation waveform data may further comprise data representing an electrically evoked compound action potential (ECAP) resulting from the one or more waveforms that were applied to the patient (115).

The method may further comprise applying a high-pass filter to remove low-frequency components of the ECAP.

The method may further comprise subtracting or attenuating, from the collected neuromodulation waveform data, at least one ECAP signal resulting from the one or more waveforms that were applied to the patient (115).

The method may further comprise subtracting or attenuating the at least one ECAP signal, using the NMD.

The method may further comprise subtracting or attenuating the at least one ECAP signal, using the waveform identification server (1640).

The method may further comprise subtracting or attenuating the at least one ECAP signal, using the computing device associated with the NMD.

Subtracting or attenuating the at least one ECAP signal may further comprise digitally subtracting an artifact model representing the at least one ECAP signal.

The artifact model may be a frequency domain artifact model.

The artifact model may be a time domain artifact model.

The method may further comprise generating the artifact model during a calibration phase.

The method may further comprise receiving the collected neuromodulation waveform data, using the computing device associated with the NMD.

The one or more waveforms may be the one or more prescription waveform protocols (1605).

The method may further comprise collecting the neuromodulation waveform data while the one or more waveforms are applied, using the NMD.

The method may further comprise collecting the neuromodulation waveform data while the one or more waveforms are applied, using a discrete collection device (1645).

The method may further comprise identifying, in the one or more waveforms applied to the patient (115), waveform signal characteristics (1630) determined as a function of the collected neuromodulation waveform data, using at least one digital signal processing (DSP) algorithm (1635).

The method may further comprise identifying the waveform signal characteristics (1630), using the waveform identification server (1640).

The method may further comprise identifying the waveform signal characteristics (1630), using the NMD.

The method may further comprise identifying the waveform signal characteristics (1630), using a discrete collection device (1645).

The method may further comprise identifying waveform signal characteristics (1630) comprising: frequency, pulse width, amplitude, charge density, interburst interval, intraburst frequency, interburst frequency and charge balance.

The method may further comprise determining if the one or more waveforms applied to the patient (115) match any known predetermined waveforms, based on comparing the identified waveform signal characteristics (1630) of the one or more waveforms applied to the patient (115) to waveform signal characteristics (1630) of any known predetermined waveforms.

The method may further comprise determining if the one or more waveforms applied to the patient (115) match any known predetermined waveforms, using the waveform identification server (1640).

The method may further comprise determining if the one or more waveforms applied to the patient (115) match any known predetermined waveforms, using the NMD.

The method may further comprise determining if the one or more waveforms applied to the patient (115) match any known predetermined waveforms, using a discrete collection device (1645).

The method may further comprise: in response to determining the one or more waveforms applied to the patient (115) matched any known predetermined waveform based on comparing the identified waveform signal characteristics (1630), generating a notification indicating the one or more waveforms applied to the patient (115) matched at least one known predetermined waveform, determined as a function of matched signal characteristics.

The method may further comprise generating the notification, using the waveform identification server (1640).

The method may further comprise generating the notification, using the NMD.

The method may further comprise generating the notification, using a discrete collection device (1645).

The method may further comprise sending the notification to the waveform prescription deployment server (1625), the NMD or the computing device associated with the NMD.

The method may further comprise determining if any known digital watermark is detected in the one or more waveforms applied to the patient (115), determined as a function of the collected neuromodulation waveform data, using at least one watermark detection algorithm (1655).

The method may further comprise determining if any known digital watermark is detected, using the waveform identification server (1640).

The method may further comprise determining if any known digital watermark is detected, using the NMD.

The method may further comprise determining if any known digital watermark is detected, using a discrete collection device (1645).

Determining if any known digital watermark is detected may further comprise demodulating a binary sequence from the collected neuromodulation waveform data and comparing the demodulated binary sequence to at least one known digital watermark.

Demodulating the binary sequence may further comprise decoding information encoded with amplitude modulation (AM) in the one or more waveforms applied to the patient (115).

Demodulating the binary sequence may further comprise decoding information encoded with pulse position modulation (PPM) in the one or more waveforms applied to the patient (115), the PPM comprising varied timing between peaks or troughs in the one or more waveforms.

Demodulating the binary sequence may further comprise detecting a carrier wave (2505) added to the one or more waveforms applied to the patient (115).

Demodulating the binary sequence may further comprise decoding information encoded with frequency modulation (FM) in the carrier wave (2505).

Demodulating the binary sequence may further comprise decoding information encoded with phase modulation (PM) in the carrier wave (2505).

Demodulating the binary sequence may further comprise decoding information encoded with amplitude modulation (AM) in the one or more waveforms applied to the patient (115).

Demodulating the binary sequence may further comprise decoding a checksum and using the checksum to verify integrity of the binary sequence.

Demodulating the binary sequence may further comprise decoding a forward error correction (FEC) code and using the FEC code to verify and/or restore integrity of the binary sequence.

The FEC code may be selected from the group consisting of Reed-Solomon, Golay, Hamming and Bose-Chaudhuri-Hocquenghem (BCH).

In response to determining if any known digital watermark is detected in the one or more waveforms applied to the patient (115), the method may further comprise generating a notification that at least one known digital watermark was detected in the one or more waveforms applied to the patient (115).

The method may further comprise generating the notification, using the waveform identification server (1640).

The method may further comprise generating the notification, using the NMD.

The method may further comprise generating the notification, using a discrete collection device (1645).

The method may further comprise: receiving, from the waveform identification server (1640), an indication that a known predetermined waveform is in use to treat a patient (115) by the NMD, using the computing device associated with the NMD; authenticating the patient (115), comprising receiving and verifying patient (115) biometric or security credential input, using the computing device associated with the NMD; in response to determining patient (115) authentication was successful, generating a security token derived from the successful patient (115) authentication and a shared secret distributed by the waveform prescription deployment server (1625), using the computing device associated with the NMD; sending, to the waveform prescription deployment server (1625), the security token with a request for approval for the patient (115) to continue using the known predetermined waveform, using the computing device associated with the NMD; receiving, from the waveform prescription deployment server (1625), an approval for the patient (115) to continue using the known predetermined waveform, using the computing device associated with the NMD, the approval comprising an activation expiration time and a time-based one-time-password (TOTP) generated by the prescription deployment server (1625) based on the security token and the shared secret, wherein the shared secret is retained by the waveform prescription deployment server (1625) and the computing device associated with the NMD; and sending the TOTP to the NMD, wherein the NMD is configured to be activated by the TOTP to continue applying the known predetermined waveform to the patient (115) until the activation expiration time.

The method may further comprise: applying a first neuromodulation waveform to a patient (115), using an NMD; collecting waveform signal data sampled while the first neuromodulation waveform is applied to the patient (115), using the NMD; applying a digital signal processing (DSP) algorithm (1635) to the collected waveform signal data to identify waveform signal characteristics (1630) of the first waveform, using the NMD; determining that the first neuromodulation waveform, based on the identified waveform signal characteristics (1630), matches a second neuromodulation waveform, the second neuromodulation waveform being a known predetermined neuromodulation waveform, using the NMD; and generating a notification that the first neuromodulation waveform being applied to the patient (115) is a known predetermined waveform, using the NMD.

The first neuromodulation waveform may further comprise a digital watermark previously applied to the first neuromodulation waveform, and wherein applying the DSP algorithm (1635) may further comprise identifying the digital watermark in the first neuromodulation waveform, using the NMD.

The method may further comprise applying the digital watermark to the first neuromodulation waveform.

Applying the digital watermark may further comprise encoding digital watermark data as a binary sequence modulated in the first neuromodulation waveform.

Modulating the binary sequence may further comprise encoding the binary sequence with amplitude modulation (AM) in the first neuromodulation waveform.

Modulating the binary sequence may further comprise encoding the binary sequence with pulse position modulation (PPM) in the first neuromodulation waveform, the PPM comprising varying timing between peaks in the first neuromodulation waveform.

Modulating the binary sequence may further comprise adding a carrier wave (2505) to the first neuromodulation waveform.

Modulating the binary sequence may further comprise encoding using frequency modulation (FM) in the carrier wave (2505).

Modulating the binary sequence may further comprise encoding using phase modulation (PM) in the carrier wave (2505).

Modulating the binary sequence may further comprise encoding a checksum determined as a function of the binary sequence and modulating, in sequence, the binary sequence and the checksum.

Modulating the binary sequence may further comprise encoding a forward error correction (FEC) code and modulating, in sequence, the binary sequence and the FEC code.

The FEC code may be selected from the group consisting of Reed-Solomon, Golay, Hamming and Bose-Chaudhuri-Hocquenghem (BCH).

The digital watermark may further comprise identifying data embedded in the first neuromodulation waveform using a low-energy carrier wave (2505) modulated with data comprising an electronic signature or digital watermark, using the NMD.

The low-energy carrier wave (2505) may further comprise a waveform having an amplitude of 10% or less of paresthesia (0.1-0.2 mA).

The NMD may be an implantable pulse generator IPG (106) implanted in the patient (115).

The first neuromodulation waveform may be applied to the patient (115) to relieve pain.

The NMD may be a WPG (1610) in contact with the patient (115) exterior.

The first neuromodulation waveform may be applied to the patient (115) to relieve pain.

The NMD may be a WPG (1610) in contact with the patient (115) exterior.

The first neuromodulation waveform may be applied to the patient (115) by the WPG (1610) to create a current directly over a targeted nerve to move a limb or digits.

Determining that the first neuromodulation waveform matches the second neuromodulation waveform may further comprise matching the identified waveform signal characteristics (1630) of the first neuromodulation waveform to known waveform signal characteristics (1630) of the second neuromodulation waveform within a predetermined variance threshold, using the NMD.

The method may further comprise the NMD registering with the waveform prescription deployment server (1625) that receives a digital prescription from a physician to treat a patient by applying the first neuromodulation waveform using the NMD.

In response to the waveform prescription deployment server (1625) receiving the digital prescription, the method may further comprise the waveform prescription deployment server (1625) generating and sending a waveform prescription activation data package to the NMD, the waveform prescription activation data package comprising identification of a particular prescribed waveform and prescription parameters including an authorized waveform application time period.

The method may further comprise the NMD receiving the prescription activation data package from the waveform prescription deployment server (1625), wherein the NMD applies the prescribed waveform to the patient (115) until the authorized application time period expires.

The method may further comprise sampling the waveform signal data using the NMD.

The method may further comprise sampling the waveform signal data using a discrete collection device (1645).

The method may further comprise forwarding, by the NMD, to the computing device associated with the NMD, the waveform signal data, and wherein the computing device associated with the NMD is configured to apply the DSP algorithm (1635) to the waveform signal data.

An application deployed to the computing device associated with the NMD may retain one or more digital prescriptions configured to unlock the NMD to apply a prescribed waveform to the patient (115).

A prescribed waveform may be downloaded to the NMD from an application deployed to a patient (115) mobile device (118).

A prescribed waveform may be downloaded to the NMD from an application deployed to a mobile device (118) used by a clinical expert who is responsible for programming the NMD.

The patient (115) may use a mobile device (118) configured to unlock the NMD to apply a prescribed waveform, based on authenticating the patient (115) to the waveform prescription deployment server (1625) using predetermined security credentials.

A clinical expert may use a mobile device (118) configured to unlock the NMD to apply a prescribed waveform, based on authenticating the clinical expert to the waveform prescription deployment server (1625) using predetermined security credentials.

An exemplary method may comprise applying a predetermined waveform protocol (133) to a patient (115) to treat a pain syndrome, while measuring at least one current patient physiological parameter (146) determined as a function of sensor data (145) captured in a feedback loop (143), using a Spinal Cord Stimulation (SCS) Implantable Pulse Generator (IPG) (106) processor (200); determining if a physiologic tolerance of the pain syndrome to the predetermined waveform protocol (133) changed as a function of the at least one current patient physiological parameter (146) measured in the feedback loop (142) and at least one historical patient physiological parameter, using the SCS IPG (106) processor (200); and in response to determining the physiologic tolerance of the pain syndrome to the predetermined waveform protocol (133) changed, triggering a modification of the predetermined waveform protocol (133) to an adapted waveform protocol (157), using the SCS IPG (106) processor (200).

The method may further comprise determining during the feedback loop (143) if the physiologic tolerance of the pain syndrome to the predetermined waveform protocol (133) changed, using the SCS IPG (106) processor (200).

The method may further comprise determining if the physiologic tolerance of the pain syndrome to the predetermined waveform protocol (133) changed based on comparing the at least one current patient physiological parameter (146) measured in the feedback loop (143) with the at least one historical patient physiological parameter, using the SCS IPG (106) processor (200).

The at least one historical patient physiological parameter may be a physiological parameter measured during a previous iteration of the feedback loop (143), using the SCS IPG (106) processor (200).

The at least one historical patient physiological parameter may be a physiological parameter (146) measured during a pre-implant trial phase (148), using the SCS IPG (106) processor (200).

The method may further comprise applying the adapted waveform protocol (157) to the patient (115), using the SCS IPG (106) processor (200).

The at least one current patient physiological parameter (146) may further comprise at least one of: heart rate (HR), heart rate variability (HRV), RR interval (RR), blood pressure (BP), body temperature (TEMP) or oxygen tension ($PaO_2$).

The at least one historical patient physiological parameter (146) may further comprise at least one of: heart rate (HR), heart rate variability (HRV), RR interval (RR), blood pressure (BP), body temperature (TEMP) or oxygen tension ($PaO_2$).

The predetermined waveform protocol (133) may further comprise at least one waveform.

The predetermined waveform protocol (133) may be at least one waveform.

The predetermined waveform protocol (133) may be a plurality of waveforms.

The predetermined waveform protocol (133) may be a plurality of distinct waveforms.

Applying the predetermined waveform protocol (133) may further comprise applying the at least one waveform in a pattern, using the SCS IPG (106) processor (200).

The pattern may further comprise an on-off pattern.

The on-off pattern may further comprise applying the at least one waveform during at least a first time period and not applying the at least one waveform during at least a second time period.

The predetermined waveform protocol (133) may further comprise a plurality of distinct waveforms.

Each waveform of the plurality of distinct waveforms may have at least one signal characteristic.

The at least one signal characteristic may further comprise amplitude, frequency or duty cycle.

Applying the predetermined waveform protocol (133) may further comprise applying the plurality of distinct waveforms in a pattern, using the SCS IPG (106) processor (200).

The pattern may further comprise a cycling pattern.

The cycling pattern may further comprise individually applying each waveform of the plurality of distinct waveforms during a respective time period of a plurality of time periods.

The pattern may further comprise an alternating pattern.

The alternating pattern may further comprise applying a first set of at least one waveform sequentially during a first time period, applying a second set of at least one waveform sequentially during a second time period, wherein the second set of at least one waveform comprises at least one waveform distinct from the first set of at least one waveform.

Applying the plurality of distinct waveforms may further comprise configuring a pulse generator (224) to apply at least one waveform of the plurality of distinct waveforms, using the SCS IPG (106) processor (200).

The method may further comprise configuring a pulse generator (224) to apply a plurality of waveforms using a plurality of electrodes (136), using the SCS IPG (106) processor (200).

The method may further comprise configuring a pulse generator (224) to apply a plurality of waveforms in series, using the SCS IPG (106) processor (200).

Apply the plurality of waveforms in series may further comprise: apply a first waveform using at least one electrode (136) during a first time period; and apply another waveform distinct from the first waveform using the at least one electrode (136) during at least a second time period after the first time period.

The method may further comprise configuring a pulse generator (224) to apply a plurality of waveforms in parallel, using the SCS IPG (106) processor (200).

Apply the plurality of waveforms in parallel may further comprise: apply at least a first waveform during a time period using at least a first electrode (136) set comprising at least one electrode (136) and apply at least another waveform during the time period using at least another electrode (136) set comprising at least one electrode (136) not in the at least the first electrode (136) set, wherein the at least another waveform is distinct from the at least the first waveform.

The method may further comprise receiving a digital indication comprising a selection of at least one predetermined waveform protocol (133), using the SCS IPG (106) processor (200).

The selected at least one predetermined waveform protocol (133) may further comprise a plurality of distinct waveforms.

The received digital indication may further comprise a run time for at least one waveform of the plurality of distinct waveforms.

The method may further comprise applying the at least one waveform for the run time before applying at least another waveform, using the SCS IPG (106) processor (200).

The method may further comprise configuring a pulse generator (224) to apply the selected at least one predetermined waveform protocol (133), using the SCS IPG (106) processor (200).

The received digital indication may further comprise an indication to apply the plurality of distinct waveforms using a respective plurality of electrode (136) sets configured to apply the plurality of distinct waveforms in parallel.

The digital indication may further comprise an indication to apply the plurality of distinct waveforms in series.

The method may further comprise receiving the selection of the at least one predetermined waveform protocol (133) from a user interface.

The digital indication may further comprise an indication to apply the plurality of distinct waveforms in a pattern.

The pattern may further comprise an alternating pattern.

The alternating pattern may further comprise applying the plurality of distinct waveforms one waveform at a time in sequence.

The received digital indication may further comprise an indication of an ordinal position of each waveform of the plurality of distinct waveforms in the sequence.

The pattern may further comprise a cycling pattern.

The cycling pattern may further comprise individually applying each waveform of the plurality of distinct waveforms during a single time period of a respective plurality of time periods. The user interface may be configured in a computing device remote from the SCS IPG (106).

The received digital indication may further comprise at least one parameter of at least one waveform of the plurality of distinct waveforms.

The at least one parameter may further comprise one or more of amplitude, frequency, or duty cycle.

The at least one parameter of the at least one predetermined waveform protocol (133) may further comprise a limitation on one or more of electric current, voltage, or power.

The method may further comprise capturing sensor data measuring patient physiological response to pain, using the SCS IPG (106) processor (200).

The method may further comprise capturing the sensor data during a neuromodulation trial procedure (148).

The sensor data may be pre-implant sensor data.

The method may further comprise: configuring at least one sensor to capture at least one patient (115) physiological parameter (146), using the SCS IPG (106) processor (200); measuring patient (115) cognitive or physical performance in a task during a neuromodulation session in a trial phase (148), using the SCS IPG (106) processor (200); testing multiple waveforms to be applied in series in the trial phase (148) while capturing the at least one patient (115) physiological parameter (146), using the SCS IPG (106) processor (200); determining patient (115) physiological response to pain and the cognitive or physical performance measured while capturing the at least one patient (115) physiological parameter (146) in the trial phase (148), for each tested waveform, using the SCS IPG (106) processor (200); establishing a reference pain syndrome tolerance to each tested waveform based on patient (115) physiological response to pain and the measured performance for each tested waveform in the trial phase (148), using the SCS IPG (106) processor (200); and prescribing an initial predetermined waveform protocol (133) to relieve pain for the patient (115) based on the reference pain syndrome tolerance established in the trial phase (148) for each tested waveform, using the SCS IPG (106) processor (200).

The trial phase (148) may further comprise establishing the reference pain syndrome tolerance to each tested waveform for a plurality of different output electrode configurations for each tested waveform, using the SCS IPG (106) processor (200).

The task may further comprise an algorithmically scripted interactive task comprising a game or test presented to the patient (115) via a mobile device (166) operably coupled with the SCS IPG (106).

Establishing the reference pain syndrome tolerance may further comprise: sampling the captured at least one patient (115) physiological parameter (146) while the patient (115) performs the task and storing the samples as a physiological parameter (146) time series, using the SCS IPG (106) processor (200); and storing the measured cognitive or physical performance with the physiological parameter (146) time series, using the SCS IPG (106) processor (200).

The neuromodulation session may further comprise: applying each tested waveform for an active application time period and not applying each tested waveform for an inactive application time period; wherein the method further comprises: storing the physiological parameter (146) time series sampled during the active application time period as an active application physiological parameter (146) time series with the cognitive or physical performance measured during the active application time period; storing the physiological parameter (146) time series sampled during the inactive application time period as an inactive application physiological parameter (146) time series with the cognitive or physical performance measured during the inactive application time period; and establishing the reference pain syndrome tolerance to the tested waveform as a reference pain syndrome tolerance time series determined as a function of the active application physiological parameter (146) time series and the inactive application physiological parameter (146) time series.

Establishing the reference pain syndrome tolerance may further comprise: sending an indication to a mobile device (166) to request measured cognitive or physical performance data in response to determining a waveform under test has been applied for a predetermined individual waveform test time period, using the SCS IPG (106) processor (200); and receiving the requested measured cognitive or physical performance data related to the waveform under test from the mobile device (166), using the SCS IPG (106) processor (200).

Prescribing may further comprise prescribing, using the SCS IPG (106) processor (200), the initial predetermined waveform protocol (133) predicted by a machine learning model to optimize a pain syndrome treatment goal selected from the group consisting of maximum relief from pain and highest resistance to pain syndrome tolerance, wherein the machine learning model is configured to determine the prediction as a function of the active application physiological parameter (146) time series and the inactive application physiological parameter (146) time series.

The method may further comprise: configuring at least one sensor to capture at least one patient (115) physiological parameter (146), using the SCS IPG (106) processor (200); applying a prescribed predetermined waveform protocol (133) while measuring the patient (115) current physiological response to pain based on at least one physiological parameter (146) captured by the at least one sensor, using the SCS IPG (106) processor (200); measure a current tolerance of the pain syndrome to the prescribed predetermined waveform protocol (133) determined as a function of a patient (115) reference physiological response to pain established in the trial phase (148) and the patient (115) current physiological response to pain, using the SCS IPG (106) processor (200); and in response to determining the tolerance of the pain syndrome to the prescribed predetermined waveform protocol (133) changed by at least a predetermined minimum tolerance threshold difference, trigger change of the prescribed predetermined waveform protocol (133) to an adapted waveform protocol (157), using the SCS IPG (106) processor (200).

Measure the current tolerance of the pain syndrome to the prescribed predetermined waveform protocol (133) may further comprise: sampling the captured at least one patient (115) physiological parameter (146) and storing the samples as a treatment phase physiological parameter (146) time series, using the SCS IPG (106) processor (200).

The method may further comprise determining the current tolerance of the pain syndrome to the prescribed predetermined waveform protocol (133) as a function of the treatment phase physiological parameter (146) time series and an active application physiological parameter (146) time series captured in the trial phase (148).

Measure the current tolerance of the pain syndrome to the prescribed predetermined waveform protocol (133) may further comprise determine a sample-by-sample difference time series based on comparing at least a portion of the treatment phase physiological parameter (146) time series and the active application physiological parameter (146) time series captured in the trial phase (148) for the prescribed predetermined waveform protocol (133).

The method may further comprise determining at least one statistical measure of the sample-by-sample difference time series.

The method may further comprise determining if the tolerance of the pain syndrome to the prescribed predetermined waveform protocol (133) changed by at least the predetermined minimum tolerance threshold difference, based on the at least one statistical measure.

The change of the prescribed predetermined waveform protocol (133) to the adapted waveform protocol (157) may further comprise modifying at least one signal characteristic of at least one waveform of the prescribed predetermined waveform protocol (133).

The modified at least one signal characteristic of the at least one waveform of the prescribed predetermined waveform protocol (133) may further comprise one or more of: amplitude, power, frequency, waveshape, duty cycle, start time in a sequence or end time in a sequence.

The change of the prescribed predetermined waveform protocol (133) to the adapted waveform protocol (157) may further comprise reassigning at least one waveform or waveform protocol to a different set of electrodes.

The trial phase (148) may further comprise establishing the reference pain syndrome tolerance to each tested waveform for a plurality of different output electrode configurations for each tested waveform, using the SCS IPG (106) processor (200).

The method may further comprise: requesting authorization to apply a prescribed predetermined waveform protocol (133) identified by a cryptographically secure digital signature, using the SCS IPG (106) processor (200); receiving a digital indication comprising authorization to provision the SCS IPG (106) to apply the authorized digitally signed prescribed predetermined waveform protocol (133) until a predetermined prescription expiration time, using the SCS IPG (106) processor (200); and configuring the SCS IPG (106) to apply the authorized digitally signed prescribed predetermined waveform protocol (133) until the predetermined prescription expiration time, using the SCS IPG (106) processor (200).

The method may further comprise receiving a digital indication comprising a selection of a prescribed predetermined waveform protocol (133) to be applied by the SCS IPG (106).

The method may further comprise receiving the digital indication comprising the selection of the prescribed predetermined waveform protocol (133) via a communication network.

The method may further comprise receiving the digital indication comprising the selection of the prescribed predetermined waveform protocol (133) from a user interface.

The method may further comprise receiving the digital indication comprising the selection of the prescribed predetermined waveform protocol (133) from a mobile app.

The digital indication comprising the selection of the prescribed predetermined waveform protocol (133) may further comprise a configuration mapping of individual waveforms of the prescribed predetermined waveform protocol (133) to individual electrodes.

The digital indication comprising the selection of the prescribed predetermined waveform protocol (133) may further comprise a plurality of configuration mappings of individual waveforms of the prescribed predetermined waveform protocol (133) to individual electrodes.

The method may further comprise activating the SCS IPG (106) to apply the authorized digitally signed prescribed predetermined waveform protocol (133), using the SCS IPG (106) processor (200).

The method may further comprise activating the SCS IPG (106) to apply the authorized digitally signed prescribed predetermined waveform protocol (133), using the SCS IPG (106) processor (200) to energize at least one individual electrode with a particular waveform of the authorized digitally signed prescribed predetermined waveform protocol (133), wherein the particular waveform was assigned to the at least one individual electrode by a digital prescription received by the SCS IPG (106).

The method may further comprise activating the SCS IPG (106) to apply the authorized digitally signed prescribed predetermined waveform protocol (133), using the SCS IPG (106) processor (200) to energize each electrode of a plurality of electrodes with a different particular waveform of the authorized digitally signed prescribed predetermined waveform protocol (133), wherein each different particular waveform was assigned to each electrode of the plurality of electrodes by a digital prescription received by the SCS IPG (106).

The method may further comprise: determining if the predetermined prescription expiration time is satisfied, using the SCS IPG (106) processor (200); and in response to determining the predetermined prescription expiration time is satisfied, deactivate the authorized digitally signed prescribed predetermined waveform protocol (133) from the SCS IPG (106), using the SCS IPG (106) processor (200).

The method may further comprise configuring the SCS IPG (106) to apply a default predetermined waveform protocol (133) after the predetermined prescription expiration time, using the SCS IPG (106) processor (200).

The default predetermined waveform protocol (133) may be a prescribed predetermined waveform protocol (133) distinct from the authorized digitally signed prescribed predetermined waveform protocol (133).

The method may further comprise: determining if the authorized digitally signed prescribed predetermined waveform protocol (133) is stored on the SCS IPG (106); in response to determining the authorized digitally signed prescribed predetermined waveform protocol (133) is stored on the SCS IPG (106), activating the SCS IPG (106) to apply the authorized digitally signed prescribed predetermined waveform protocol (133), using the SCS IPG (106) processor (200); and in response to determining the authorized digitally signed prescribed predetermined waveform protocol (133) is not stored on the SCS IPG (106), downloading the authorized digitally signed prescribed predetermined waveform protocol (133) to the SCS IPG (106), using the SCS IPG (106) processor (200).

The method may further comprise: configuring the SCS IPG (106) to measure at least one signal characteristic of at least one waveform, using the SCS IPG (106) processor (200); measuring the at least one signal characteristic of the at least one waveform while the waveform is applied, using the SCS IPG (106) processor (200); comparing the measured at least one signal characteristic with at least one signal characteristic of at least one predetermined waveform to determine if the currently applied at least one waveform matches the at least one predetermined waveform, based on the comparison; and in response to determining the currently applied at least one waveform matches the at least one predetermined waveform, sending an indication the predetermined waveform is in use by the SCS IPG (106), using the SCS IPG (106) processor (200).

The at least one applied waveform may be a plurality of distinct waveforms comprising a predetermined waveform protocol (133).

Measuring the at least one signal characteristic may further comprise sampling in the time domain, using the SCS IPG (106) processor (200).

Measuring the at least one signal characteristic may further comprise sampling in the frequency domain, using the SCS IPG (106) processor (200).

The at least one signal characteristic of the at least one applied waveform may further comprise at least one of amplitude, frequency or duty cycle.

The at least one predetermined waveform may be hosted by an authorization server.

Sending the indication the predetermined waveform is in use may further comprise sending the indication to an authorization server, using the SCS IPG (106) processor (200).

Comparing the measured at least one signal characteristic may further comprise determining a correlation of a measured waveform power spectrum with a predetermined waveform power spectrum, using the SCS IPG (106) processor (200).

Comparing may further comprise a frequency-bin by frequency bin comparison of amplitudes in the measured waveform power spectrum with the predetermined waveform power spectrum, using the SCS IPG (106) processor (200).

The method may further comprise determining the correlation in the frequency domain, using the SCS IPG (106) processor (200).

The method may further comprise determining a correlation coefficient value of at least 0.75 indicates the currently applied at least one waveform matches the at least one predetermined waveform, using the SCS IPG (106) processor (200).

The method may further comprise configuring a minimum correlation coefficient threshold value that must be reached to determine the currently applied at least one waveform matches the at least one predetermined waveform.

The method may further comprise determining the correlation in a predetermined passband width, using the SCS IPG (106) processor (200).

The predetermined passband width may be a configurable passband width, using the SCS IPG (106) processor (200).

The method may further comprise configuring the passband width to a passband width received with a digital indication from a user interface, using the SCS IPG (106) processor (200).

The method may further comprise: receiving sensor information (145) comprising the physiological response of the patient (115) to pain from at least one sensor, using the SCS IPG (106) processor (200); comparing the received sensor information (145) from the at least one sensor to reference sensor information (145) comprising the physiological response of the patient (115) captured when the patient (115) was not experiencing a pain crisis, to determine if the patient is experiencing a pain crisis based on the comparison, using the SCS IPG (106) processor (200); in response to determining the patient (115) is experiencing a pain crisis, activating at least one effector (139) configured to change spinal cord (112) activity based on providing external stimulation to the patient (115), using the SCS IPG (106) processor (200); and adjusting the external stimulation to the patient (115) to mitigate the pain crisis, using the SCS IPG (106) processor (200).

The at least one sensor may be configured to measure at least one of: blood pressure, heart rate or oxygen tension.

The at least one sensor may further comprise at least one wearable sensor.

The at least one wearable sensor may further comprise a hat configured to capture brain waves (EEG).

The at least one wearable sensor may further comprise a wrist band.

The at least one wearable sensor may further comprise an effector (139) configured to provide external stimulation to the patient (115).

The effector may be a hat configured to provide extracranial stimulation.

The effector may be a wrist band configured to provide acupressure.

The at least one wearable sensor may be in physical contact with the patient (115).

The at least one wearable sensor may further comprise at least one effector (139).

The at least one effector (139) may be a vagal nerve stimulator, an acupressure stimulator or an extracranial stimulator.

Adjusting the external stimulation to the patient (115) may further comprise adjusting intensity of the external stimulation to the patient (115), using the SCS IPG (106) processor (200).

Adjusting the external stimulation to the patient (115) may further comprise adjusting frequency of the external stimulation to the patient (115), using the SCS IPG (106) processor (200).

Adjusting the external stimulation to the patient (115) may further comprise modulating the external stimulation to the patient (115) in an on/off pattern, using the SCS IPG (106) processor (200).

Adjusting the external stimulation to the patient (115) may further comprise activating more than one effector (139) to provide the external stimulation to the patient (115), using the SCS IPG (106) processor (200).

The method may further comprise communicatively pairing the at least one sensor with the SCS IPG (106) processor (200).

The method may further comprise communicatively pairing the at least one effector with the SCS IPG (106) processor (200).

The method may further comprise communicatively pairing the at least one sensor with a mobile device (166) operably coupled with the SCS IPG (106).

The method may further comprise communicatively pairing the at least one effector with a mobile device (166) operably coupled with the SCS IPG (106).

The method may further comprise: in response to determining the patient (115) is experiencing the pain crisis, triggering an application configured in a mobile device (166) of the patient to display heart rate or blood pressure to the patient while interacting with the patient (115) in an algorithmically scripted biofeedback scenario designed to help the patient (115) calm themselves by reducing their heart rate or blood pressure.

The method may further comprise triggering an application configured in the mobile device (166) of the patient to play music or other content that has been determined to calm the patient.

An exemplary method may comprise: conducting a pre-implant trial phase (148) using a universal spinal cord stimulator implantable pulse generator ("SCS IPG") (106), comprising a processor (200) and sensors (139), wherein the SCS IPG (106) is configured to run a plurality of waveform protocols (133) to treat a patient (115) with a pain syndrome (134), further wherein the pre-implant trial phase (148) comprises individually applying each of the plurality of waveform protocols (133) to the patient (115) in series to measure at least one physiological parameter (146) consisting of heart rate, heart rate variability and oxygen tension; storing the plurality of waveform protocols (133) and the at least one corresponding physiological parameter (146) in the SCS IPG (106) using the processor (200); selecting a first waveform protocol from the pre-implant trial phase (148) plurality of waveform protocols (133); implanting the SCS IPG (106) into the patient (115); applying the first waveform protocol to the patient (115) during a treatment phase (151) to treat the pain syndrome (134), using the SCS IPG (106) processor (200); determining if a physiologic tolerance of the pain syndrome (134) to the first waveform protocol changed as a function of comparing the at least one patient physiological parameter (146) measured during the treatment phase (151) to the same at least one physiological parameter measured in the pre-implant trial phase (148) for the first waveform protocol, using the SCS IPG (106) processor (200); and in response to determining the physiologic tolerance of the pain syndrome (134) changed, initiating a modification of the first waveform protocol to an adapted waveform protocol (157), using the SCS IPG (106) processor (200).

The method may further comprise in response to determining the physiologic tolerance of the pain syndrome (134) to the adapted waveform protocol (157) changed during a feedback loop (143), initiating a modification of the adapted waveform protocol (157) using the SCS IPG (106) processor (200).

The method may further comprise determining if the physiologic tolerance of the pain syndrome (134) to the adapted waveform protocol (157) changed as a function of comparing the at least one patient physiological parameter (146) measured in a feedback loop (143) to the same at least one patient physiological parameter (146) measured in previous iteration of the feedback loop (143) for the same adapted waveform protocol (157), using the SCS IPG (106) processor (200).

The at least one patient physiological parameter (146) may further consist of RR interval (RR), and body temperature (TEMP).

The waveform protocol (133) may comprise at least one waveform, more than one waveform or a plurality of waveforms.

Applying the waveform protocol (133) may further comprise applying the at least one waveform in a pattern, using the SCS IPG (106) processor (200).

The method may further comprise: measuring patient (115) cognitive or physical performance in a task comprising a game or test presented to the patient (115) via a mobile device (166) operably coupled with the SCS IPG (106) during a neuromodulation session in the pre-implant trial phase (148), using the SCS IPG (106) processor (200); determining the patient (115) physiological response to pain and the cognitive or physical performance measured while capturing the at least one patient (115) physiological parameter (146) in the pre-implant trial phase (148), for each tested waveform protocol (133), using the SCS IPG (106) processor (200); establishing a reference pain syndrome tolerance to each tested waveform protocol (133) based on the patient (115) physiological response to pain and the measured performance for each tested waveform protocol (133) in the pre-implant trial phase (148), using the SCS IPG (106) processor (200); and prescribing an initial waveform protocol (133) to relieve pain for the patient (115) based on the reference pain syndrome tolerance established in the pre-implant trial phase (148) for each tested waveform protocol (133), using the SCS IPG (106) processor (200).

The task may further comprise an algorithmically scripted interactive task comprising a game or test presented to the patient (115) via the mobile device (166) operably coupled with the SCS IPG (106).

Establishing the reference pain syndrome tolerance may further comprise: sampling the captured at least one patient (115) physiological parameter (146) while the patient (115) performs the task and storing the samples in a time series, using the SCS IPG (106) processor (200); and storing the measured cognitive or physical performance with the time series samples of the physiological parameters (146), using the SCS IPG (106) processor (200).

The neuromodulation session in the pre-implant trial phase (148) may further comprise: applying each tested waveform protocol (133) for an active application time period and ceasing the application of each tested waveform protocol (133) for an inactive application time period; storing a time series of samples of the physiological parameters (146), sampled during the active application time period; storing a time series of samples of the physiological parameters (146), sampled during the inactive application time period; and establishing the reference pain syndrome tolerance to the tested waveform protocol (133) as a function of a comparison between the active application time series samples and the inactive application time series samples.

Establishing the reference pain syndrome tolerance may further comprise: sending an indication to the mobile device (166) to request measured cognitive or physical performance data using the SCS IPG (106) processor (200); and receiving the requested measured cognitive or physical performance data related to each tested waveform protocol (133) from the mobile device (166), using the SCS IPG (106) processor (200).

The method may further comprise prescribing a waveform protocol (133) predicted by a machine learning model to optimize a pain syndrome treatment goal selected from the group consisting of maximum relief from pain and highest resistance to pain syndrome tolerance, wherein the machine learning model is configured to determine the prediction as a function of the comparison between the active time series samples of the physiological parameters (146) and the inactive time series samples of the physiological parameters (146) using the SCS IPG (106) processor (200).

The method may further comprise: activating at least one effector sensor (139) configured to change spinal cord (112) activity based on providing external stimulation to the patient (115), using the SCS IPG (106) processor (200); and adjusting the external stimulation to the patient (115) to mitigate a pain crisis, using the SCS IPG (106) processor (200).

Adjusting the external stimulation to the patient (115) may further comprise adjusting intensity or frequency of the external stimulation to the patient (115), using the SCS IPG (106) processor (200).

The method may further comprise: in response to determining the patient (115) is experiencing the pain crisis, triggering an application configured in a mobile device (166) of the patient to display heart rate or blood pressure to the patient while interacting with the patient (115) in an algorithmically scripted biofeedback scenario designed to help the patient (115) calm themselves by reducing their heart rate or blood pressure.

An exemplary method may comprise: configuring a universal spinal cord stimulator implantable pulse generator ("SCS IPG") (106) to measure at least one signal characteristic of at least one waveform protocol while the at least one waveform protocol is applied to a patient (115), using a SPS IPG processor (200); conducting a neuromodulation session in a pre-implant trial phase (148) using the SCS IPG (106), comprising the processor (200) and sensors (139), wherein the SCS IPG (106) is configured to run a plurality of waveform protocols (133) to treat the patient (115) with a pain syndrome (134), further wherein the pre-implant trial phase (148) comprises individually applying each of the plurality of waveform protocols (133) to the patient (115) in series to measure at least one corresponding physiological parameter (146) consisting of heart rate, heart rate variability and oxygen tension; storing the plurality of waveform protocols (133) and the at least one corresponding physiological parameter (146) in the SCS IPG (106) using the SCS IPG (106) processor (200); selecting a first waveform protocol (133) from the pre-implant trial phase (148) plurality of waveform protocols (133); implanting the SCS IPG (106) into the patient (115); applying the selected first waveform protocol (133) to the patient (115) during a treatment phase (151) to treat the pain syndrome (134) while measuring the at least one signal characteristic, using the SCS IPG processor (200); comparing the at least one signal characteristic measurement with known waveform protocols to determine if the selected first waveform protocol (133) matches any of the known waveform protocols, based on the comparison; and in response to determining the selected first waveform protocol (133) matches any known waveform protocol, sending to an authorization server (127) an indication the known waveform protocol is in use by the SCS IPG (106), using the SCS IPG (106) processor (200).

The method may further comprise determining if a physiologic tolerance of the pain syndrome (134) to the selected first waveform protocol changed as a function of comparing the at least one patient physiological parameter (146) measured during the treatment phase (151) to the same at least one patient physiological parameter (146) measured in the pre-implant trial phase (148) for the selected first waveform protocol, using the SCS IPG (106) processor (200).

The method may further comprise in response to determining the physiologic tolerance of the pain syndrome (134) changed during a feedback loop (143), initiating a modification of the first waveform protocol to an adapted waveform protocol (157), using the SCS IPG (106) processor (200).

The method may further comprise determining if the physiologic tolerance of the pain syndrome (134) to the adapted waveform protocol (157) changed as a function of comparing the at least one patient physiological parameter (146) measured in the feedback loop (143) to the same at least one patient physiological parameter (146) measured in a previous iteration of the feedback loop (143) for the same adapted waveform protocol (157), using the SCS IPG (106) processor (200).

The method may further comprise in response to determining the physiologic tolerance of the pain syndrome (134) to the adapted waveform protocol (157) changed during the feedback loop (143), initiating a modification of the adapted waveform protocol (157) using the SCS IPG (106) processor (200).

The method may further comprise: comparing the measured at least one signal characteristic of the adapted waveform protocol (157) with at least one signal characteristic of any known waveform protocols to determine if the adapted waveform protocol (157) matches at least one known waveform protocol, based on the comparison; and in response to determining the adapted waveform protocol (157) matches any known waveform protocols, sending to an authorization server (127) an indication the known waveform protocol is in use by the SCS IPG (106), using the SCS IPG (106) processor (200).

The at least one patient physiological parameter (146) may further consist of RR interval (RR), and body temperature (TEMP).

The at least one signal characteristic may be one or more of: amplitude, frequency or duty cycle, wherein the signal characteristics are measured using the SCS IPG (106) processor (200).

The neuromodulation session in the pre-implant trial phase (148) may further comprise: applying each tested waveform protocol (133) for an active application time period and ceasing the application of each tested waveform protocol (133) for an inactive application time period; storing a time series of samples of the physiological parameters (146), sampled during the active application time period; storing a time series of samples of the physiological parameters (146), sampled during the inactive application time period; and establishing a reference pain syndrome tolerance to the tested waveform protocol (133) as a function of a comparison between the active application time series samples and the inactive application time series samples.

The first waveform protocol or adapted waveform protocol may comprise a licensed waveform.

In response to sending the indication to the authorization server (127) that the known waveform protocol is in use by the SCS IPG (106), the method may further comprise receiving a digital indication authorizing the SCS IPG (106) to use the licensed waveform, using the SCS IPG (106) processor (200).

Determining if the selected first waveform protocol applied to the patient (115) matches any known waveform protocols may further comprise determining a power spectrum correlation between the selected first waveform protocol and any known waveform protocol, using the SCS IPG (106) processor (200).

The method may further comprise determining the selected first waveform protocol matches a known waveform protocol upon determining the power spectrum correlation has a correlation coefficient value of at least 0.75.

Measuring the at least one signal characteristic may comprise frequency domain sampling, using the SCS IPG (106) processor (200).

Configuring the SCS IPG (106) to measure at least one signal characteristic of at least one waveform protocol while the at least one waveform protocol is applied to the patient (115) may further comprise configuring one or more energy output connection and one or more energy input connection with one or more electrodes, using the SCS IPG (106) processor (200).

An exemplary method may comprise: configuring a universal spinal cord stimulator implantable pulse generator ("SCS IPG") (106) to measure at least one signal characteristic of at least one waveform protocol while the at least one waveform protocol is applied to a patient (115) having a pain syndrome (134), using an SPS IPG processor (200); applying a first selected waveform protocol (133) to the patient (115) during a treatment phase (151) using the SCS IPG implanted in the patient (115) to treat the pain syndrome (134) while measuring the at least one signal characteristic, using the SCS IPG processor (200); comparing the at least one signal characteristic measurement of the first selected waveform protocol (133) with known waveform protocols to determine if the selected first waveform protocol matches any of the known waveform protocols, based on the comparison; and in response to determining the selected first waveform protocol (133) matches any known waveform protocols, sending to an authorization server (127) an indication the known waveform protocol is in use by the SCS IPG (106), using the SCS IPG processor (200).

An exemplary method may comprise: receiving a digital indication to apply a prescribed waveform protocol (133) to a patient (115) having a pain syndrome (134) for a predetermined time, using a spinal cord stimulator implantable pulse generator ("SCS IPG") (106) processor (200); applying the prescribed waveform protocol (133) to the patient (115) while measuring at least one signal characteristic comprising amplitude, frequency or duty cycle, using the SCS IPG (106) processor (200); comparing the measured at least one signal characteristic with at least one signal characteristic of any known waveform protocols to determine if the prescribed waveform protocol (133) matches any known waveform protocols, based on the comparison; and in response to determining the prescribed waveform protocol (133) matches a known waveform protocol, sending to an authorization server (127) an indication the known waveform protocol is in use, using the SCS IPG processor (200).

The method may further comprise configuring the SCS IPG (106) to apply the prescribed waveform protocol (133) for the predetermined time, using the SCS IPG (106) processor (200).

The method may further comprise configuring the SCS IPG (106) to measure the at least one signal characteristic while the SCS IPG (106) applies the prescribed waveform protocol (133) to the patient (115), using the SCS IPG processor (200).

Configuring the SCS IPG (106) to measure the at least one signal characteristic may further comprise configuring one or more energy output connections to apply the prescribed waveform protocol (133) to the patient (115) with one or more electrodes and configuring one or more energy input connections to measure the at least one signal characteristic with the one or more electrodes, using the SCS IPG processor (200).

The digital indication to apply the prescribed waveform protocol (133) may further comprise a digital prescription received from a mobile device.

The digital prescription may further comprise: a selection of known waveform protocols (133) from a library of individually available known waveforms (121); and a prescription expiration time.

The prescribed waveform protocol (133) may be customized by a doctor (103) using a waveform protocol customization, configuration and prescribing user interface (227) operably coupled with the SCS IPG processor (200), using the SCS IPG processor (200).

The method may further comprise: performing a test to determine if the predetermined time has been satisfied, using the SCS IPG processor (200); upon determining the predetermined time has been satisfied, stopping application of the prescribed waveform protocol (133) to the patient, using the SCS IPG processor (200); and upon determining the predetermined time has not been satisfied, continuing application of the prescribed waveform protocol (133) to the patient (115), using the SCS IPG processor (200).

The method may further comprise configuring the SCS IPG (106) to apply a default waveform protocol (133) to the patient (115) when the predetermined time is satisfied.

The method may further comprise conducting a neuromodulation session in a pre-implant trial phase (148) using an SCS IPG (106) comprising a processor (200) and sensors (139), wherein the SCS IPG (106) is configured to run a plurality of waveform protocols (133) including the prescribed waveform protocol (133) to treat a patient (115) having the pain syndrome (134), further wherein the pre-implant trial phase (148) comprises individually applying each of the plurality of waveform protocols (133) to the patient (115) in series to measure at least one corresponding physiological parameter (146) consisting of heart rate, heart rate variability and oxygen tension; and storing the plurality of waveform protocols (133) and the at least one corresponding physiological parameter (146) in the SCS IPG (106) using the SCS IPG (106) processor (200).

The at least one patient physiological parameter (146) may further consist of RR interval (RR), and body temperature (TEMP).

The method may further comprise determining if a physiologic tolerance of the pain syndrome (134) to the prescribed waveform protocol (133) changed as a function of comparing the at least one patient physiological parameter (146) measured during a treatment phase (151) to the same at least one patient physiological parameter (146) measured in the pre-implant trial phase (148) for the prescribed waveform protocol (133), using the SCS IPG (106) processor (200).

The method may further comprise in response to determining the physiologic tolerance of the pain syndrome (134) changed during a feedback loop (143), initiating a modification of the prescribed waveform protocol (133) to an adapted waveform protocol (157), using the SCS IPG (106) processor (200).

The method may further comprise determining if the physiologic tolerance of the pain syndrome (134) to the adapted waveform protocol (157) changed as a function of comparing the at least one patient physiological parameter (146) measured in the feedback loop (143) to the same at least one patient physiological parameter (146) measured in a previous iteration of the feedback loop (143) for the same adapted waveform protocol (157), using the SCS IPG (106) processor (200).

The method may further comprise in response to determining the physiologic tolerance of the pain syndrome (134) to the adapted waveform protocol (157) changed during the feedback loop (143), initiating a modification of the adapted waveform protocol (157) using the SCS IPG (106) processor (200).

The adapted waveform protocol may be a prescribed waveform protocol (133).

Spinal Cord Stimulation (SCS) devices may be used to improve chronic pain syndromes. An SCS device may be a peripheral stimulation device. Some SCS devices may comprise an Implantable Pulse Generator (IPG). An SCS IPG may be configured with leads designed to stimulate a patient's spinal cord with electrical energy. The electrical energy may be delivered to the spinal cord in the form of an electrical waveform generated by the SCS IPG.

An SCS IPG may be implanted in a patient. Some patients may develop tolerance for a particular waveform. A waveform that a patient has developed tolerance for may not be effective to reduce pain for that patient. A patient that has developed tolerance for a particular waveform may need to have an implanted SCS IPG explanted, or surgically removed, and replaced with another SCS IPG that can use another more effective waveform.

Disclosed herein is an Open Label SCS IPG device which is capable of downloading and/or uploading and running multiple existing waveforms and using the waveforms to improve chronic pain syndromes. An exemplary Open Label SCS IPG may be capable of downloading and/or uploading patented waveforms from different companies after the appropriate permission is granted to do so. There may need to be an agreement in place to download patented waveforms on this device, after which the waveforms can be run in individualized frequencies to maximize patient benefit.

The invention relates to receiving a digital indication comprising authorization to use at least two predetermined waveforms as input to an Open Label implantable pulse generator (IPG) configured for multiple waveform spinal cord stimulation (SCS), using a computing device operably coupled with the IPG; downloading and storing the at least two waveforms to the computing device and unlocking the IPG using code executing on the computing device to run the at least two waveforms on the IPG using an individualized alternating or cycling waveform protocol customized using the computing device; and using the individualized protocol with the IPG to limit physiologic tolerance to individual waveforms while stimulating a spinal cord.

Waveform signals may be customized or edited using the computing device. The Open Label SCS IPG may be configured to self-adjust individualized protocols with different waveforms and stimulation patterns based on closed loop techniques using patient feedback, advantageously discovering effective protocols and preventing tolerance.

The user may be enabled to edit or splice the waveforms. Various implementations may permit waveforms to be edited/created and automatic cycling of patented (downloadable) waveforms may be edited. Once waveforms are uploaded into the Open Label SCS IPG they can be modified or remain unchanged. However, the Open Label SCS IPG can run the uploaded waveforms in series or parallel, customized to the needs of the patient. An Open Label SCS IPG implementation may be configured to autonomously adjust waveforms using closed loop waveform adjustment algorithms that may be enabled by a programmer/patient/healthcare personnel. The closed loop algorithms may be turned off by a programmer/patient/healthcare personnel. In some examples the closed loop algorithm implementation may be a software application downloadable to the Open Label SCS IPG to run on the Open Label SCS IPG.

One possible IPG closed loop algorithm implementation may run a test pattern of unmodified waveforms 1, 2, 3, 2, 1, 2, . . . and then obtain evaluation criteria for example asking the patient to indicate how well that treatment worked or determine over time if the patient developed tolerance, and then change future repetition patterns based on whether or how well that test pattern worked. However, closed loop is a different technology that self-adjusts waveform energy depending on patient position (breathing, sitting, standing, walking). The running of waveforms 1,2,3, 2,1,2 should be pre-set by a healthcare worker to determine patient safety, then once it is determined that the patient can benefit from/tolerate that waveform sequence it will be introduced into the IPG memory as a profile that can be turned on/off by the patient or programmer. An exemplary IPG implementation may be configured to run different licensed waveforms, that are currently not able to be run on any currently existing IPG.

In one embodiment, the Open Label SCS IPG is configured to download and run a plurality of waveforms licensed from a respective plurality of IPG manufacturers. The plurality of waveforms is configured to run on the Open Label SCS IPG in an alternating or cycling pattern customized to a patient to prevent the patient from developing tolerance for individual waveforms.

In another embodiment, the Open Label SCS IPG is configured to download pre-existing waveforms and run the pre-existing waveforms in series or parallel to apply the waveforms using an algorithmically determined waveform protocol. The waveform protocol may be algorithmically determined to cycle, alternate, or vary the waveforms to reduce pain syndrome tolerance to the waveform. A feedback function assessing pain, sleep, and Heart Rate (HR) determined using sensor data may be configured to trigger a pre-programmed change in the waveform(s) protocol.

The Open Label SCS IPG may be configured with a BLUETOOTH connection to a tablet computer for waveform analysis and programming.

Any of the foregoing implementations can be employed individually or in conjunction. An SCS IPG implementation in accordance with the present disclosure may achieve one or more technical effects. For example, some implementations may improve accuracy measuring the tolerance of a patient's pain syndrome to a predetermined waveform. Such improved accuracy measuring the pain syndrome tolerance to a predetermined waveform may be a result of measuring patient physiological parameters in a feedback loop using sensors to determine the patient's current physiological response to pain. For example, using sensor data to determine the patient's current physiological response to pain may provide more accurate automatic measurements of a waveform's effectiveness over time. Such automatic measurements of a patient's current physiological response to pain based on sensor data may improve the usefulness of measuring the patient's level of pain. Such improved usefulness of measuring the patient's level of pain may be a result of replacing or supplementing subjective, patient-reported pain levels with captured sensor data representing the patient's current physiological response to pain. For example, measured pain levels based on captured sensor data representing the patient's current physiological response to pain may provide a pain measurement that is more accurate than subjective, patient-reported pain levels provided by a patient over time for a particular pain syndrome. Measuring the patient's current physiological response to pain determined as a function of sensor data captured during a treatment phase and comparing the current physiological response to pain with the patient's reference physiological response to pain determined as a function of sensor data captured during a trial phase may improve the usefulness and responsiveness of neuromodulation therapy. For example, based on comparing the current physiological response over time with the historical physiological response, an SCS IPG implementation in accordance with the present disclosure may detect a change in the tolerance of the patient's pain syndrome more quickly than a patient could self-report. Such an SCS IPG may be able to trigger a change of the predetermined waveform protocol to an adapted waveform protocol more quickly than a patient could self-report increased pain. For example, the SCS IPG may trigger a change of the predetermined waveform protocol to an adapted waveform protocol before the patient would be aware of increased pain. This facilitation may be a result of replacing or supplementing subjective, patient-reported pain levels with captured sensor data representing the patient's physiological response to pain in the feedback loop, permitting the SCS IPG to detect and react to trends in the patient physiological response to pain.

An exemplary Open Label Spinal Cord Stimulator (SCS) Implantable Pulse Generator (IPG) implementation may be configured to run all waveforms in a customizable format. An SCS IPG implementation may be configured to download pre-existing waveforms and run the pre-existing waveforms in series or parallel to apply the waveforms using an algorithmically determined waveform protocol. The waveform protocol may be algorithmically determined to cycle, alternate, or vary the waveforms to reduce pain syndrome tolerance to the waveform. A feedback function assessing pain, sleep, and Heart Rate (HR) determined using sensor data would trigger a pre-programmed change in the waveform(s) protocol.

Reference is made herein to particular features of various implementations. It is to be understood that the disclosure of particular features of various implementations in this specification is to be interpreted as including all possible combinations of such particular features. For example, where a particular feature is disclosed in the context of a particular aspect or implementation, or a particular claim, that feature can also be used—to the extent possible—in combination with and/or in the context of other particular aspects and implementations, and in an implementation generally.

Suitable methods and corresponding materials to make each of the individual parts of implementation apparatus are known in the art. One or more implementation part may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and clastomers as may be described herein-above may be used. Many suitable materials are known and available and can be selected and mixed depending on desired strength and flexibility, preferred manufacturing method and particular use, as will be apparent to a person of ordinary skill in the art.

The phrases "connected to," "coupled to" and "in communication with" refer to any form of interaction between two or more entities, including mechanical, electrical, magnetic, electromagnetic, fluid, chemical and thermal interaction. Two components may be functionally coupled to each other even though they are not in direct contact with each other. The terms "abutting" or "in mechanical union" refer to items that are in direct physical contact with each other, although the items may not necessarily be attached together. A first computing device configured to send an electronic message to a second computing device may send the electronic message through one or more other intervening systems. A first computing device configured to receive an electronic message from a second computing device may receive the electronic message through one or more other intervening systems.

One of ordinary skill in the art would appreciate that an exemplary system appropriate for use with implementation in accordance with the present application may generally include one or more of a Central processing Unit (CPU), Random Access Memory (RAM), a storage medium (e.g., hard disk drive, solid state drive, flash memory, cloud storage), an operating system (OS), one or more application software, a display element, one or more communications means, or one or more input/output devices/means. Examples of computing devices usable with implementations of the present disclosure include, but are not limited to, proprietary computing devices, personal computers, mobile computing devices, tablet PCs, mini-PCs, servers, or any combination thereof. The term computing device may also describe two or more computing devices communicatively linked in a manner as to distribute and share one or more resources, such as clustered computing devices and server banks/farms. One of ordinary skill in the art would understand that any number of computing devices could be used, and implementation of the present disclosure are contemplated for use with any computing device.

An exemplary Open Label SCS IPG may include hardware comprising an IPG configured to run various licensed waveforms in individualized format. An exemplary SCS IPG may comprise software configured to download licensed waveforms. An agreement or contract may be implemented digitally using the device to obtain the required permission to download and use a licensed waveform. An exemplary Open Label SCS IPG may advantageously limit physiologic tolerance in many patients with chronic pain, as a result of the expansion of available waveforms.

An exemplary Open Label SCS IPG may be configured to receive data comprising information captured by at least one sensor. The at least one sensor may comprise one or more of: a Digital wristband, a Digital vagal sleep sensor, and Digital Hat with EEG sensors. The depicted Open Label SCS IPG comprises software configured to download pre-existing SCS waveforms as well as vagal stimulators and extracranial stimulation. An agreement or contract may be implemented digitally using the device to download and use a licensed waveform. The depicted exemplary Open Label SCS IPG may advantageously limit pain syndrome physiologic tolerance in many patients with a chronic pain syndrome, based on decreasing pain by direct electric communication with the spinal cord through adapting differential waveforms. Various Open Label SCS IPG implementations may be configured to download pre-existing waveforms and run the pre-existing waveforms singularly, in parallel, or in series. The device may be configured to autonomously change waveforms or sequences of waveforms based on measuring specific changes in patient physiology (HR, RR, REM sleep, body position, and temperature). In an illustrative example HR, RR, REM sleep may be captured by a digital wristband, vagal sleep sensor, and hat with EEG sensors and the information will be relayed to the Open Label SCS IPG. An Open Label SCS IPG system may be configured to create bidirectional information transfer. For example, the Open Label SCS IPG may be configured to receive information from the sensors to change spinal cord activity and also deliver information to the EEG and sleep sensors to alter sleep and provide extracranial therapy. The Open Label SCS IPG may autonomously change waveforms or waveform frequency depending on physiologic parameters that suggest increased pain.

An exemplary Open Label SCS IPG may be configured to self-adjust different waveforms based on closed loop technology. The Open Label SCS IPG may be designed to enable downloading of the waveforms over a protected Wi-Fi connection. The Open Label SCS IPG may be configured to permit waveform configurations and programming easy enough for a clinician to perform, instead of the practice based on current technology requiring skilled representatives from neuromodulation companies to perform complex programming). Various implementations may be configured to run waveforms in a protocol designed to use less energy, by running waveforms less often or only when needed as determined based on sensor data, thereby permitting an increase in the Open Label SCS IPG battery life. Some designs may comprise software configured to permit a clinician to create and evaluate new waveforms and export the new waveforms to a database or another IPG, to expand any current IPG's capability to improve chronic pain syndromes.

An exemplary Open Label SCS IPG may be configured to customize a protocol designed to apply multiple waveforms in combination to work in together in a cycling or customizable manner. The multiple waveforms may be applied in series or in parallel. Multiple waveforms may be applied in parallel to energize multiple respective lead sets wherein each lead set delivers energy from one of the waveforms at a time to a portion of a spinal cord. The portion of the spinal cord that the energy from each waveform is delivered to may be different for each lead set.

An Open Label SCS IPG may be configured to use wearable body technology to assess physiologic change. An Open Label SCS IPG may be configured to deliver information to the wearable technology to enact change in physiology. An Open Label SCS IPG may be configured to unlock a device to run multiple pre-existing or predetermined waveforms that reduce cost and increase effectiveness by comparison with current designs.

An Open Label SCS IPG may be configured to use patient physiology from wearable sensors to enact changes in SCS outflow to minimize tolerance. An Open Label SCS IPG may be configured to effect physiologic parameters known to influence chronic pain such as sleep and headache. An Open Label SCS IPG may be configured to allow downloading of the new waveform(s) via BLUETOOTH/internet or other protected connection, permitting a patient to obtain the benefit from the new waveforms without reoperation or explantation of their existing IPG. An Open Label SCS IPG implementation may be configured with an electronic wristband and the bidirectional vagal and cranial stimulators. An Open Label SCS IPG may be configured to self-adjust different waveforms based on closed loop technology from wearable technology sensors. An Open Label SCS IPG may be configured to allow downloading of the waveforms over a protected Wi-Fi connection. Various Open Label SCS IPG implementations may be configured to increase battery life, increase charging capability, increase power of IPG, sense other physiologic parameters such as glucose, CBC, BMP, and triglycerides, and may be configured with an external battery which can be used when high power functions are needed such as vagal and extracranial stimulation.

An Open Label SCS IPG may be configured to permit customizing waveforms to work in together in a cycling or customizable manner. The disclosed Open Label SCS IPG design, implementation and usage techniques may be generalized to any medically implanted device which may benefit from electronic upgrading. Some Open Label SCS IPG implementations may be configured to monitor general body blood chemistry and heartrate. An Open Label SCS IPG may be configured to improve sleep by vagal stimulating effects or improve headache by transcranial application.

Although some exiting IPG designs have body position sensing ability, the IPG senses this information apriori; there is no wearable tech that provides information to the IPG or from the IPG to the wearables. Extracranial and vagal stimulators exist, but none connect with an SCS IPG to alter SCS function or are modified by an SCS IPG to minimize pain and mitigate tolerance.

In exemplary scenarios illustrative of prior art IPG design and usage, if a new waveform is suggested by a physician a patient has to undergo an explantation of a current IPG and re-implantation with a new device capable of running the recommended new waveform. Furthermore, implantation of the new device subjects the patient with the inability to run their older waveforms. Although current SCS IPG devices may be unlocked to allow for other waveforms to be uploaded to the devices, an exemplary Open Label SCS IPG may be configured to permit downloading/uploading waveforms from different companies onto other companies' currently implanted IPGs, or an implementation of the Open Label SCS IPG disclosed herein.

An exemplary SCS IPG method may comprise: receiving a digital indication comprising authorization to use at least two predetermined waveforms as input to an implantable pulse generator (IPG) configured for multiple waveform spinal cord stimulation (SCS), using a computing device operably coupled with the IPG; downloading and storing the at least two waveforms to the computing device and unlocking the IPG using code executing on the computing device to run the at least two waveforms on the IPG using an individualized alternating or cycling waveform protocol customized using the computing device; and using the individualized protocol with the IPG to limit physiologic tolerance to individual waveforms while stimulating a spinal cord. The method may further comprise customizing or editing SCS waveform signals to run on the IPG, using the computing device. The method may further comprise self-adjusting individualized protocols with different waveforms and stimulation patterns based on closed loop techniques using patient feedback, using the IPG.

An exemplary Open Label SCS IPG device may be configured for downloading and running multiple existing waveforms and using the waveforms to improve chronic pain syndromes. An exemplary Open Label SCS IPG may be capable of downloading predetermined waveforms. The waveforms may be run in individualized frequencies to maximize patient benefit. Various implementations may permit waveforms to be edited/created. An Open Label SCS IPG implementation may be configured to autonomously adjust waveforms using closed loop waveform adjustment algorithms. The Open Label SCS IPG may be configured to download pre-existing waveforms and run pre-existing waveforms in series or parallel to apply the waveforms using algorithmically determined waveform protocols. The waveform protocols may be algorithmically determined to cycle, alternate, or vary the waveforms to reduce pain syndrome tolerance to individual waveforms or waveform protocols. A feedback function assessing pain, sleep, and Heart Rate (HR) determined using sensor data may trigger a pre-programmed change in the waveform(s) protocol.

An exemplary Open Label Spinal Cord Stimulation (SCS) Implantable Pulse Generator (IPG) may be configured to treat a pain syndrome based on applying a predetermined waveform protocol to a patient, while measuring patient physiological parameters in a feedback loop using sensors and triggering a change of the predetermined waveform protocol to an adapted waveform protocol, in response to detecting a change in the tolerance of the pain syndrome to the predetermined waveform protocol. The waveform protocol may be one or multiple waveforms cycling or alternating in patterns to prevent a pain syndrome from developing tolerance to individual waveforms. Pain syndrome tolerance may be determined based on preset, pre-implantation data. Pain syndrome tolerance to the predetermined waveform protocol may be based on the patient's pain level determined from the physiological or patient self-reported parameters. The IPG may be provisioned to apply a digitally authenticated waveform protocol during a time period governed by a digitally signed prescription.

An exemplary neuromodulation device may be configured to treat a pain syndrome based on applying a predetermined waveform to a patient, while measuring patient physiological parameters in a feedback loop using sensors and triggering a change of the predetermined waveform to an adapted waveform, in response to detecting a change in the tolerance of the pain syndrome to the predetermined waveform. The neuromodulation device may be, for example, a Spinal Cord Stimulation Implantable Pulse Generator (SCS IPG). The SCS IPG may be configured to measure signal characteristics of an applied waveform using input electrodes while the same waveform is applied to a patient using output electrodes. The SCS IPG may compare the measured signal characteristics to signal characteristics of a predetermined waveform to determine if the applied waveform matches the predetermined waveform. The SCS IPG may send an indication to an authorization server that the predetermined waveform is in use.

An implementation in accordance with the present disclosure may be configured to permit an owner or licensor of a neuromodulation waveform to determine whether their waveform is applied to a patient by the IPG or WPG device. The IPG, WPG or separate measurement device may be implemented and configured to collect the waveform data corresponding to waveforms being applied to a patient. The IPG, WPG or separate measurement device may collect the waveform data using input electrodes in contact with the patient while the waveform is applied to the patient. The separate measurement device may be a patient-wearable device without output electrodes. The IPG or WPG may apply a waveform to the patient using output electrodes while measuring the applied waveform using different input electrodes. The IPG, WPG or separate measurement device may use a wireless network interface such as Bluetooth or Wi-Fi to forward the collected waveform data to a computing device for processing to identify the waveform. The computing device may be a mobile device operated by the patient. The computing device may be a waveform identification server remote from the patient. The waveform identification server may be configured with identification algorithms that have been independently designed by the waveform owners, permitting transparent verification of waveform usage. The mobile device or waveform identification server may receive the collected waveform data and perform further operations to identify the applied waveform. The separate measurement device may be employed by waveform owners as an alternative/independent monitor of applied waveforms.

Apparatus and associated methods disclosed herein relate to analyzing waveforms being applied to a patient by an implantable or wearable pulse generator (IPG or WPG) and determining whether the applied waveform is a previously known waveform. The IPG may be configured to apply one or more neuromodulation waveforms to a patient. The IPG may be implanted in the patient. The WPG may be a wearable pulse generator configured to create a current directly over a targeted nerve. The WPG may be configured to cause sensory or motor stimulation as a result of creating the current directly over the targeted nerve. The WPG may be used to relieve pain or to move a limb or digits (for example to treat patients who have had a stroke or may be paralyzed). The WPG may be used for moving a limb or digits in patients with chronic pain. For example, the WPG may be configured to create a current directly over a targeted nerve to cause motor stimulation while applying one or more neuromodulation waveforms to the patient for pain management. In some cases, one WPG may create a current directly over a targeted nerve to cause motor stimulation while an IPG or another WPG apply one or more neuromodulation waveforms to the patient for pain management. The IPG, WPG or a separate measurement device may be configured to collect waveform data to measure an applied waveform while the waveform is being applied to the patient. The separate measurement device may be a measure-only device implemented without waveform generation capability. The separate measurement device may be a patient-wearable device placed in contact with the patient. A computing device may receive, and process waveform data collected by the IPG, WPG or the separate measurement device. The computing device may be for example, a mobile device, a patient-wearable device, or a waveform identification server remote from the patient location.

The computing device can apply a digital signal processing (DSP) algorithm to the data to identify characteristics of the waveform and/or decode identifying data from a watermark embedded in the applied waveform. A watermark can refer to a type of signal, information or data embedded within the waveform for identification purposes. The watermark should not alter the clinical efficacy or safety of the waveform. For example, identifying data may be embedded in a waveform using a low-energy carrier signal modulated to create an electronic signature. The low-energy carrier signal may be configured to have an amplitude of 10% or less of paresthesia (0.1-0.2 mA) to avoid effects on neural or cellular activity, while being strong enough for collection and measurement. If the computing device determines the applied waveform matches the characteristics of a known waveform, or if identifying watermark data is detected, the computing device can generate and send a notification that the known waveform is in use. For example, the computing device may notify a waveform's owner or licensor that their waveform is in use, facilitating invoicing, prescription usage or treatment protocol conformance. The applied waveform may be any predetermined or arbitrarily customized waveform that can be prescribed and applied to a patient using the IPG or WPG.

A server process may digitally authorize the IPG or WPG to apply the prescribed waveform for a predetermined time. The prescribed waveforms may be downloaded to the IPG or WPG from an application deployed to the patient's mobile device or from a clinical expert's mobile device who is responsible for programming the IPG/WPG. The application deployed to the patient's mobile device may retain one or more digital prescriptions to apply a prescribed waveform to a patient. The application deployed to the patient's mobile device or the clinical expert's mobile device may be configured to authenticate the patient and/or the clinical expert using biometric identifying information or predetermined security credentials, to unlock the IPG or WPG to apply a prescribed waveform.

The IPG or WPG is a device capable of running and applying any arbitrary waveform signal(s) whether licensed predetermined waveforms or custom-designed waveforms. A prescription server process may be configured to receive a digital prescription from a medical professional who has the ability to program a particular waveform to be applied by the IPG or WPG. The prescription server process may be further configured to generate a waveform prescription activation data package comprising identification of a particular prescribed waveform and prescription parameters, such as for example authorized application time period, a default waveform to revert to after the authorized time period and custom parameters that are to be applied to the prescribed waveform, such as duty cycle and/or intensity. In one example implementation, the prescription server process transmits the waveform prescription activation data package to the WPG or IPG. The WPG or IPG receives the waveform prescription activation data package and activates the prescribed waveforms according to the prescription. When the authorized application time period expires, the WPG or IPG ceases application of the prescribed waveform and reverts to applying the default waveform specified by the prescription.

In one embodiment, characteristics of known and/or licensed waveforms used in neuromodulation treatment can be digitally stored. For example, the waveform characteristics can be stored in a database. Upon collecting waveform data from an IPG device, the computing device can identify characteristics of the waveform by applying a digital signal processing (DSP) algorithm to the waveform data. This can include the waveform's amplitude, frequency, phase, and other characteristics. The computing device can then compare the waveform's characteristics to the characteristics of known waveforms to determine whether a match exists. If so, the computing device can notify the owner/licensor of the waveform. The waveform matching or identification stages described above can be performed by a single device or a combination of computing devices. For example, a mobile device can receive waveform data collected by the WPG, IPG or a separate measurement device. The mobile device may forward the waveform data to a waveform identification server configured to apply a DSP algorithm to the waveform data to search for waveform matches or detect an identifying watermark in the waveform data. The mobile device may apply a DSP algorithm to the waveform data, or the mobile device may send the resulting waveform characteristics to the waveform identification server for further analysis.

An implementation in accordance with the present disclosure may comprise a calibration phase configured to obtain a more accurate estimate of neuromodulation waveforms applied to the patient. The calibration phase may be implemented by at least one processor configured with processor executable program instructions and data. The processor executable program instructions and data implementing the calibration phase may be designed to remove or mitigate distortion from received energy of one or more neuromodulation waveform applied to a patient. In an illustrative example an exemplary calibration phase may model the signal path from output electrodes, through the patient's body to the input electrodes as a communications channel. An exemplary implementation may apply communications theory to the channel model, to calculate the channel impulse response and use the impulse response to approximate the signal transmitted through the channel as originally intended, with distortion introduced by the patient's body removed or mitigated. Removing or mitigating distortion introduced by the patient's body may result in a more accurate estimate of the signal that was applied to the patient. Using a more accurate estimate of the signal that was applied to the patient may result in improved accuracy matching known predetermined neuromodulation waveforms in real time as the neuromodulation waveforms are applied to the patient.

For example, an exemplary implementation in accordance with the present disclosure may approximate a signal transmitted through a communication channel having a known impulse response, based on receiving the signal through the communication channel and processing the received signal and the communication channel impulse response to approximate the transmitted signal. The communication channel impulse response may be determined by capturing a training or test signal that has passed through the channel. The training or test signal may comprise a low-energy carrier wave having an amplitude of 10% or less of paresthesia (0.1-0.2 mA) to avoid effects on neural or cellular activity, while being strong enough to characterize the channel by determining the channel's impulse response.

The received signal will be a combination of the transmitted signal and any channel-induced distortions resulting from the patient's body. The channel impulse response may be estimated by correlating the received signal with the known transmitted signal, or by deconvolution (inverse filtering) to estimate the channel impulse response. The expected received signal energy (i.e., the transmitted signal as intended) from an applied neuromodulation waveform may be estimated by deconvolving the actual received signal with the channel impulse response. The applied neuromodulation waveform may be estimated using adaptive equalization to approximate the applied neuromodulation waveform signal through the communication channel and mitigate distortion introduced by the patient's body.

Channel estimation techniques may be employed to remove one or more electrically evoked compound action potential (ECAP) signal from received waveform energy. For example, the channel impulse response may be obtained from a training signal passed through the channel. A neuromodulation waveform may be applied to the patient, while capturing received energy from the patient. The applied waveform may be a known predetermined waveform or any custom configured arbitrary waveform. In this example, the applied waveform is known at least because the waveform is being applied to the patient. The channel impulse response may be used to estimate the signal input to the channel, as disclosed herein. The signal input to the channel may comprise a neuromodulation waveform and an ECAP signal. An implementation may subtract or cancel the known applied waveform from the estimated signal input using DSP techniques available to one of ordinary skill, to obtain an estimate of the ECAP signal resulting from the particular waveform being applied to the patient. The estimate of the ECAP signal resulting from the particular waveform being applied may be used to create an artifact model as discussed herein. An ECAP artifact model may be used to subtract or attenuate the ECAP signal from measurement of the applied waveform, to obtain more accurate waveform matching in accordance with one or more technical effects of the present disclosure.

In an illustrative example, an implementation in accordance with the present disclosure may begin a calibration phase by transmitting a known test signal through the channel. The known test signal may be replicated at the receiver. An adaptive equalizer may be configured to minimize error between the received signal and the transmitted signal. For example, adaptive filtering algorithms such as Least Mean Square (LMS) or Recursive Least Squares (RLS)) may be implemented to calibrate the equalizer to remove distortion from received signals by adjusting adaptive equalizer coefficients. The calibration phase may be repeated periodically, permitting adaptation to changing patient body conditions, electrode placement or waveform adaptation. An exemplary implementation may apply the calibrated adaptive equalizer to received energy from neuromodulation waveforms applied to the patient, to remove distortion resulting from the patient's body and obtain a more accurate estimate of the neuromodulation waveform that was applied to the patient.

Various implementations may achieve one or more advantages. Some implementations may increase patient access to effective neuromodulation waveforms. This increased access to effective neuromodulation waveforms may be a result of detecting the use of proprietary neuromodulation waveforms in real time, by a neuromodulation device that can be configured to apply any arbitrary waveform. Detecting use of proprietary neuromodulation waveforms in real time may result in sending waveform usage notifications to licensors of proprietary neuromodulation waveforms, facilitating automatically invoicing the patient or an insurance provider. Such automatic real time detection and notification of proprietary neuromodulation waveforms may reduce waveform licensors' effort enforcing usage restrictions on their proprietary waveforms. Reducing licensors' enforcement effort may result in wider patient access to licensed waveforms by a neuromodulation device configured to apply any waveform. Such wider patient access to licensed waveforms may be a result of detecting predetermined waveform use based on comparing the waveform being applied to multiple predetermined waveforms including licensed waveforms, and sending a notification to licensors if use of a predetermined waveform is detected.

Some designs may improve proprietary waveform detection accuracy. Such improved proprietary waveform detection accuracy may be a result of identifying a waveform using a digital watermark embedded in the waveform being applied, permitting independent usage verification. This facilitation may be a result of collecting waveform signal data from a patient's body in real time as an arbitrary waveform is applied to the patient and sending the collected waveform signal data to a third party. Some designs may watermark proprietary waveforms without changing the treatment effect or safety of the proprietary waveforms. This facilitation may be a result of modulating watermark data in the waveform based on only varying waveform amplitude to encode digital data. Various implementations may reduce neuromodulation device regulatory approval and safety testing effort. This facilitation may be a result of modulating watermark data with frequency modulation, using a low energy carrier wave. For example, a carrier wave having an amplitude of 10% or less of paresthesia (0.1-0.2 mA) may avoid effects on neural or cellular activity, while being strong enough for collection and measurement. Such a low energy carrier wave added to a proprietary waveform may only need to be tested or approved once for embedding in many different proprietary waveforms, eliminating the need to obtain regulatory approval for each new watermark. Various implementations may achieve more reliable detection of a proprietary waveform applied to a patient. Such increased detection reliability may be a result of more accurate measurements achieved by identifying and subtracting an electrically evoked compound action potential (ECAP) resulting from the waveform applied to the patient.

In the present disclosure "electronic message" should be understood to mean any form of electronic communication including but not limited to data packets, interrupts, button presses, function calls, error messages, visual indications, and the like.

As used herein, a singular term may include multiple objects. As used herein, a single element may include multiple such elements. For example, the term "computer" may include a single computer or multiple computers. The phrase "a computer that stores data and runs software," may include a single computer that both stores data and runs software, a first computer that stores data and a second computer that runs software, or multiple computers that together store data and run software, where at least one of the multiple computers stores data and at least one of the multiple computers runs software. For example, the term "processor" may include a single processor or multiple processors. The phrase "a processor that stores data and runs software," may include a single processor that both stores data and runs software, a first processor that stores data and a second processor that runs software, or multiple processors that together store data and run software, where at least one of the multiple processors stores data and at least one of the multiple processors runs software. An implementation comprising multiple processors may configure each particular processor of the multiple processors to exclusively execute only a particular task assigned to that particular processor. An implementation comprising multiple processors may configure each particular processor of the multiple processors to execute any task of multiple tasks assigned to that particular processor by a scheduler such that a different task may be assigned to different processors at different times. As used herein in an apparatus or a computer-readable medium, "at least one" object rather than or in addition to a single object may perform the claimed operations. For example, "a computer-readable medium" may be construed as "at least one computer-readable medium," and "an apparatus comprising a processor and a memory" may be construed as "a system comprising processing circuitry and a memory subsystem," or "a system comprising processing circuitry and memory" (where memory lacks the article 'a'). It should be noted that a skilled person would understand that "processing circuitry" may include a single processor or multiple processors. Similarly "memory subsystem" or "memory" (lacking an article) may include a single memory unit or multiple memory unit.

In the present disclosure "digital indication" should be understood as synonymous and interchangeable with "electronic message."

In the present disclosure, "signal characteristics" should be understood as synonymous and interchangeable with "signal parameters."

In the Summary above, in this Detailed Description, the Claims below, the content of each of the applications incorporated by reference herein and in the accompanying drawings, reference is made to features of various embodiments of the invention. It is to be understood that the disclosure of embodiments of the invention in this specification includes all possible combinations of such features. For example, where a particular feature is disclosed in the context of a particular aspect or embodiment of the invention, or a particular claim, that feature can also be used—to the extent possible—in combination with and/or in the context of other aspects and embodiments of the invention, and in the invention generally.

In various implementations, elements described herein as coupled or connected may have an effectual relationship realizable by a direct connection or indirectly with one or more other intervening elements. The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The terms "abutting" or "in mechanical union" refer to items that are in direct physical contact with each other, although the items may not necessarily be attached together.

Recitation in a claim of the term "first" with respect to a feature or element does not necessarily imply the existence of a second or additional such feature or element.

The word "exemplary" is used herein to mean "serving as an example, instance, or illustration." Any implementation described herein as "exemplary" is not necessarily to be construed as preferred over other implementations.

While various implementations have been disclosed and described in detail herein, it will be apparent to those skilled in the art that various changes may be made to the disclosed configuration, operation, and form without departing from the spirit and scope thereof. In particular, it is noted that the respective implementation features, even those disclosed solely in combination with other implementation features, may be combined in any configuration excepting those readily apparent to the person skilled in the art as nonsensical. Likewise, use of the singular and plural is solely for the sake of illustration and is not to be interpreted as limiting.

In the present disclosure, various features may be described as being optional, for example, through the use of the verb "may;" or, through the use of any of the phrases: "in some implementations," "in some designs," "in various implementations," "in various designs," "in an illustrative example," or, "for example." For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be implemented in seven different ways, namely with just one of the three possible features, with any two of the three possible features or with all three of the three possible features.

Therefore, it is intended that the invention not be limited to the particular embodiments disclosed as the best mode contemplated for carrying out this invention, but that the invention will include all embodiments falling within the scope of the present application as set forth in the following claims, wherein reference to an element in the singular, such as by use of the article "a" or "an" is not intended to mean "one and only one" unless specifically so stated, but rather "one or more." Moreover, no claim element is to be construed under the provisions of 35 U.S.C. § 112 (f), or 35 U.S.C. § 112, sixth paragraph (pre-AIA), unless the element is expressly recited using the phrase "means for" or "step for." These following claims should be construed to maintain the proper protection for the present invention.

What is claimed is:

1. A method comprising:
    receiving, by a waveform prescription deployment server (1625), a digital prescription for a neuromodulation device (NMD) to apply one or more prescription waveform protocols (1605) to a patient (115);
    sending, by the waveform prescription deployment server (1625), to a computing device associated with the NMD, a request for patient (115) authentication by the computing device associated with the NMD;
    in response to receiving, by the waveform prescription deployment server (1625), an indication of successful patient (115) authentication, generating and sending, by the waveform prescription deployment server (1625) to the computing device associated with the NMD, a prescription activation data package activating the NMD to apply the one or more prescription waveform protocols (1605) to the patient (115), wherein the waveform prescription deployment server (1625) generates a shared secret during registration, based on a trusted public key received from the computing device associated with the NMD, and wherein the NMD activates to apply the one or more prescription waveform protocols (1605) to the patient (115) when a correct TOTP is received from the computing device associated with the NMD; and
    sending, by the waveform prescription deployment server (1625) to a waveform identification server (1640), an electronic message configured to cause the waveform identification server (1640) to determine if signal characteristics of the one or more prescription waveform protocols (1605) applied to the patient (115) match signal characteristics of any of a selection of known waveform protocols (133) from a library of individually available known waveforms (121), using neuromodulation waveform data collected using at least one input electrode in contact with the patient (115) while the one or more prescription waveform protocols are applied to the patient (115) by the NMD using at least one output electrode in contact with the patient (115).

2. The method of claim 1, wherein the NMD is an implantable pulse generator (IPG) 106 or a wearable pulse generator (WPG) 1610.

3. The method of claim 1, wherein the method further comprises receiving, by the waveform prescription deployment server (1625), a registration request uniquely identifying the patient (115) and the NMD, wherein the registration request further comprises a trusted public key associated with the NMD, and wherein the registration request is received from the computing device associated with the NMD.

4. The method of claim 1, wherein the computing device associated with the NMD is a mobile device (118) configured to be operably coupled with the NMD.

5. The method of claim 1, wherein the method further comprises receiving, by the waveform prescription deployment server (1625), from the NMD or the computing device associated with the NMD, a request for an approval to treat the patient (115) using the one or more prescription waveform protocols (1605) for a predetermined time.

6. The method of claim 5, wherein the request for the approval to treat the patient (115) further comprises a request to use the one or more prescription waveform protocols (1605) within a radius of a location determined based on location sensor data captured by the NMD or the computing device associated with the NMD.

7. The method of claim 5, wherein the method further comprises sending, by the waveform prescription deployment server (1625), to the NMD or the computing device associated with the NMD, the approval to treat the patient (115) using the one or more prescription waveform protocols (1605).

8. The method of claim 1, wherein the prescription activation data package further comprises an indication of a default waveform protocol and a prescription expiration time, and the NMD is configured to cease applying the one or more prescription waveform protocols (1605) and begin applying the default waveform protocol when: the prescription expiration time is reached or when the NMD moves outside a radius of an NMD location configured in the NMD, wherein when the NMD moves outside the configured radius is determined as a function of location sensor data captured by the NMD or the computing device associated with the NMD.

9. The method of claim 1, wherein the method further comprises downloading the one or more prescription waveform protocols (1605) to the NMD using an application deployed to the computing device associated with the NMD.

10. The method of claim 1, wherein patient (115) authentication further comprises the computing device associated with the NMD receiving and verifying patient (115) time-based one-time-password (TOTP) input against a TOTP configured to change at least once per hour, wherein a correct TOTP is determined as a function of time and a shared secret generated by the waveform prescription deployment server (1625), and wherein the TOTP is generated based on RFC 4226 or RFC 6238.

11. The method of claim 1, wherein the method further comprises the NMD refraining from applying the one or more prescription waveform protocols (1605) to the patient (115) unless a correct TOTP is received from the computing device associated with the NMD, using the NMD.

12. The method of claim 1, wherein receiving the indication of successful patient (115) authentication further comprises receiving and validating a security token generated by the computing device associated with the NMD in response to user biometric input verified against a stored biometric template, wherein the security token is derived by the computing device associated with the NMD from the successful patient (115) authentication and the shared secret.

13. The method of claim 1, wherein patient (115) authentication further comprises receiving patient (115) biometric input and verifying the patient (115) biometric input against a stored biometric template, using the computing device associated with the NMD.

14. The method of claim 13, wherein the patient (115) biometric input and the stored biometric template further comprises data captured from at least one of: a fingerprint for fingerprint identification, a voice for speaker identification, a face for facial recognition, a retina for eye identification or a gesture.

15. The method of claim 1, wherein the method further comprises receiving, by the waveform identification server (1640), collected neuromodulation waveform data comprising sampled waveform signal data or measured waveform signal characteristics, the neuromodulation waveform data collected while one or more waveforms were applied to the patient (115).

16. The method of claim 15, wherein the collected neuromodulation waveform data was collected using at least one input electrode in contact with the patient (115) while the one or more waveforms were applied to the patient (115) using at least one output electrode in contact with the patient (115).

17. The method of claim 15, wherein the method further comprises subtracting or attenuating, from the collected neuromodulation waveform data, at least one electrically evoked compound action potential (ECAP) signal resulting from the one or more waveforms that were applied to the patient (115).

18. The method of claim 15, wherein the method further comprises identifying, in the one or more waveforms applied to the patient (115), waveform signal characteristics (1630) determined as a function of the collected neuromodulation waveform data, using at least one digital signal processing (DSP) algorithm (1635).

19. The method of claim 18, wherein the method further comprises determining if the one or more waveforms applied to the patient (115) match any known predetermined waveforms, based on comparing the identified waveform signal characteristics (1630) of the one or more waveforms applied to the patient (115) to waveform signal characteristics (1630) of any known predetermined waveforms.

20. The method of claim 19, wherein the method further comprises: in response to determining the one or more waveforms applied to the patient (115) matched any known predetermined waveform based on comparing the identified waveform signal characteristics (1630), generating a notification indicating the one or more waveforms applied to the patient (115) matched at least one known predetermined waveform, determined as a function of matched signal characteristics, and wherein the method further comprises sending the notification to the waveform prescription deployment server (1625), the NMD or the computing device associated with the NMD.

21. The method of claim 15, wherein the method further comprises: determining if any known digital watermark is detected in the one or more waveforms applied to the patient (115), determined as a function of the collected neuromodulation waveform data, using at least one watermark detection algorithm (1655), and wherein in response to determining at least one known digital watermark is detected in the one or more waveforms applied to the patient (115), the method further comprises generating and sending a notification that at least one known digital watermark was detected in the one or more waveforms applied to the patient (115), and wherein determining if any known digital watermark is detected further comprises demodulating a binary sequence from the collected neuromodulation waveform data and comparing the demodulated binary sequence to at least one known digital watermark.

22. The method of claim 21, wherein demodulating the binary sequence further comprises decoding information encoded with amplitude modulation (AM), frequency modulation (FM) or pulse position modulation (PPM) in the one or more waveforms applied to the patient (115).

23. The method of claim 21, wherein demodulating the binary sequence further comprises decoding a forward error correction (FEC) code and using the FEC code to verify and/or restore integrity of the binary sequence, and wherein the FEC code is selected from the group consisting of Reed-Solomon, Golay, Hamming and Bose-Chaudhuri-Hocquenghem (BCH).

24. The method of claim 1, wherein the method further comprises:
receiving, from the waveform identification server (1640), an indication that a known predetermined waveform is in use to treat a patient (115) by the NMD, using the computing device associated with the NMD;

authenticating the patient (115), comprising receiving and verifying patient (115) biometric or security credential input, using the computing device associated with the NMD;

in response to determining patient (115) authentication was successful, generating a security token derived from the successful patient (115) authentication and a shared secret distributed by the waveform prescription deployment server (1625), using the computing device associated with the NMD;

sending, to the waveform prescription deployment server (1625), the security token with a request for approval for the patient (115) to continue using the known predetermined waveform, using the computing device associated with the NMD;

receiving, from the waveform prescription deployment server (1625), an approval for the patient (115) to continue using the known predetermined waveform, using the computing device associated with the NMD, the approval comprising an activation expiration time and a time-based one-time-password (TOTP) generated by the prescription deployment server (1625) based on the security token and the shared secret, wherein the shared secret is retained by the waveform prescription deployment server (1625) and the computing device associated with the NMD; and sending the TOTP to the NMD, wherein the NMD is configured to be activated by the TOTP to continue applying the known predetermined waveform to the patient (115) until the activation expiration time.

25. The method of claim 1, wherein the method further comprises:

applying a first neuromodulation waveform to a patient (115), using an NMD;

collecting waveform signal data sampled while the first neuromodulation waveform is applied to the patient (115), using the NMD;

applying a digital signal processing (DSP) algorithm (1635) to the collected waveform signal data to identify waveform signal characteristics (1630) of the first waveform, using the NMD;

determining that the first neuromodulation waveform, based on the identified waveform signal characteristics (1630), matches a second neuromodulation waveform, the second neuromodulation waveform being a known predetermined neuromodulation waveform, using the NMD; and generating a notification that the first neuromodulation waveform being applied to the patient (115) is a known predetermined waveform, using the NMD.

26. The method of claim 1, the method further comprises applying a digital watermark to the one or more prescription waveform protocols (1605) based on encoding digital watermark data as a binary sequence and modulating the binary sequence in the one or more prescription waveform protocols (1605) using amplitude modulation (AM), frequency modulation (FM), phase modulation (PM) or pulse position modulation (PPM).

27. The method of claim 26, wherein modulating the binary sequence further comprises adding a carrier wave (2505) having an amplitude of 10% or less of paresthesia (0.1-0.2 mA) to at least one waveform of the one or more prescription waveform protocols (1605).

28. The method of claim 1, wherein the NMD is a WPG (1610) in contact with the patient (115) exterior, and wherein the one or more prescription waveform protocols (1605) are applied to the patient (115) to create a current directly over a targeted nerve to move a limb or digits.

* * * * *